US010646515B2

(12) United States Patent
Jarvis et al.

(10) Patent No.: US 10,646,515 B2
(45) Date of Patent: May 12, 2020

(54) CD8+ REGULATORY T-CELLS FOR USE IN THE TREATMENT OF INFLAMMATORY DISORDERS OF THE HUMAN GASTROINTESTINAL TRACT

(71) Applicant: GENOVIE AB, Karlskrona (SE)

(72) Inventors: Reagan Micheal Jarvis, Sydney (AU); Magnus Thörn, Uppsala (SE)

(73) Assignee: GENOVIE AB, Karlskrona (SE)

( * ) Notice: Subject to any disclaimer, the term of this patent is extended or adjusted under 35 U.S.C. 154(b) by 165 days.

(21) Appl. No.: 15/303,867

(22) PCT Filed: Apr. 16, 2015

(86) PCT No.: PCT/EP2015/058320
§ 371 (c)(1),
(2) Date: Oct. 13, 2016

(87) PCT Pub. No.: WO2015/158856
PCT Pub. Date: Oct. 22, 2015

(65) Prior Publication Data
US 2017/0165298 A1    Jun. 15, 2017

(30) Foreign Application Priority Data

Apr. 16, 2014 (DK) .................................. 2014 70224
Jul. 11, 2014 (DK) .................................. 2014 70439

(51) Int. Cl.
*A61K 35/17* (2015.01)
*G01N 33/569* (2006.01)
*C12N 5/0783* (2010.01)
*A61K 9/08* (2006.01)
*A61K 47/02* (2006.01)

(52) U.S. Cl.
CPC ............... *A61K 35/17* (2013.01); *A61K 9/08* (2013.01); *A61K 47/02* (2013.01); *C12N 5/0637* (2013.01); *G01N 33/56972* (2013.01); *G01N 2333/70517* (2013.01)

(58) Field of Classification Search
None
See application file for complete search history.

(56) References Cited

U.S. PATENT DOCUMENTS

| 9,637,527 | B2 | 5/2017 | Loukas et al. | |
| 9,726,666 | B2 | 8/2017 | Winqvist et al. | |
| 9,884,915 | B2 | 2/2018 | Chamorro Perez et al. | |
| 2009/0192434 | A1* | 7/2009 | Thorn | C07K 16/28 604/6.03 |
| 2017/0035808 | A1 | 2/2017 | Jarvis et al. | |
| 2017/0038394 | A1 | 2/2017 | Jarvis et al. | |
| 2017/0038395 | A1 | 2/2017 | Jarvis et al. | |
| 2017/0224732 | A1* | 8/2017 | Cantor | A61K 39/0008 |

FOREIGN PATENT DOCUMENTS

WO    WO-2012/054509    4/2012

OTHER PUBLICATIONS

Loftus (PSC-IBD: a unique form of inflammatory bowel disease associated with primary sclerosing cholangitis, 2005). (Year: 2005).*
Thomas (Targeting leukocyte migration and adhesion in Crohn's disease and ulcerative colitis, 2012). (Year: 2012).*
Brusko et al., "Clinical application of regulatory T cells for treatment of type 1 diabetes and transplantation," Eur. J. Immunol. (2008) vol. 38, pp. 901-937.
Office Action dated Jun. 13, 2018 in U.S. Appl. No. 15/303,866 (US 2017-0035808).
Suzuki et al., "CD8+CD45RA+CCR7+FOXP3+ T Cells with Immunosuppressive Properties: A Novel Subset of Inducible Human Regulatory T Cells," The Journal of Immunology, vol. 189, No. 5, pp. 2118-2130, Jul. 2012.
Gerner et al., "Targting T and B Lymphocytes in Inflammatory Bowel Diseases: Lessons from Clinical Trials," Digestive Diseases, vol. 31, No. 3-4, pp. 328-335, Jan. 2013.
Engelhardt et al., "Homing in on Acute Graft vs. Host Disease: Tissue-Specific T Regulatory and Th17 Cells," Vaccines for Pandemic Influenza, vol. 341, pp. 121-146, Jan. 2010.
Desreumaux et al., "Safety and Efficacy of Antigen-Specific Regulatory T-Cell Therapy for Patients with Refractory Crohn's Disease," Gastroenterolgoy, vol. 143, No. 5, pp. 1207-1217, Nov. 2012.
Thomas et al., "Targeting leukocyte migration and adhesion in Crohn's disease and ulcerative colitis," Inflammopharmacology, vol. 20, No. 1, pp. 1-18, Dec. 2011.
Horwitz et al., "Therapeutic polyclonal human CD8+ CD25+ Fox3+ TNFR2+ PD-L1+ regulatory cells inducedex-vivo," Clinical Immunology, vol. 149, No. 3, pp. 450-463, Aug. 2013.
Levings et al., "Human CD25+CD4+ T regulatory cells suppress naive and memory T cell proliferation and can be expanded in vitro without loss of function," The Journal of Experimental Medicine, vol. 193, No. 11, pp. 1295-1301, Jun. 2001.
International Search Report dated Jul. 20, 2015 in application No. PCT/EP2015/058320.
PCT International-Type Search Report dated Dec. 19, 2014 in Danish application No. 201470224.
Office Action dated Nov. 3, 2017 in U.S. Appl. No. 15/303,871 (2017-0038395).
Beissert et al., "Regulatory T Cells", Journal of Investigative Dermatology (Jan. 2006) vol. 126, pp. 15-24.
Li et al., "Mechanism and Localization of CD8 Regulatory T Cells in a Heart Transplant Model of Tolerance", The Journal of Immunology (Jun. 2010) vol. 185, pp. 823-833.

(Continued)

*Primary Examiner* — Nghi V Nguyen
(74) *Attorney, Agent, or Firm* — Foley & Lardner LLP

(57) ABSTRACT

The present invention relates to composition comprising an isolated CD8+ Treg cell population, wherein the Treg cells have signatures for i) identifying that the T-cells are CD8+ regulatory Tcells, ii) identifying that the Treg cells are tissue type tropic, i.e they can migrate to the diseased tissue, iii) optionally identifying that the Treg cells are tropic with respect to the diseased tissue, i.e. they are homing cells, iv) identifying that the Treg cells are emigrant cells, i.e. they originate from the target tissue, and v) optionally identifying that the Treg cells are capable of being retained in the target tissue and optionally one or more X-signatures and/or one or more Y-signatures.

10 Claims, 21 Drawing Sheets

(56) References Cited

OTHER PUBLICATIONS

Figure 1:
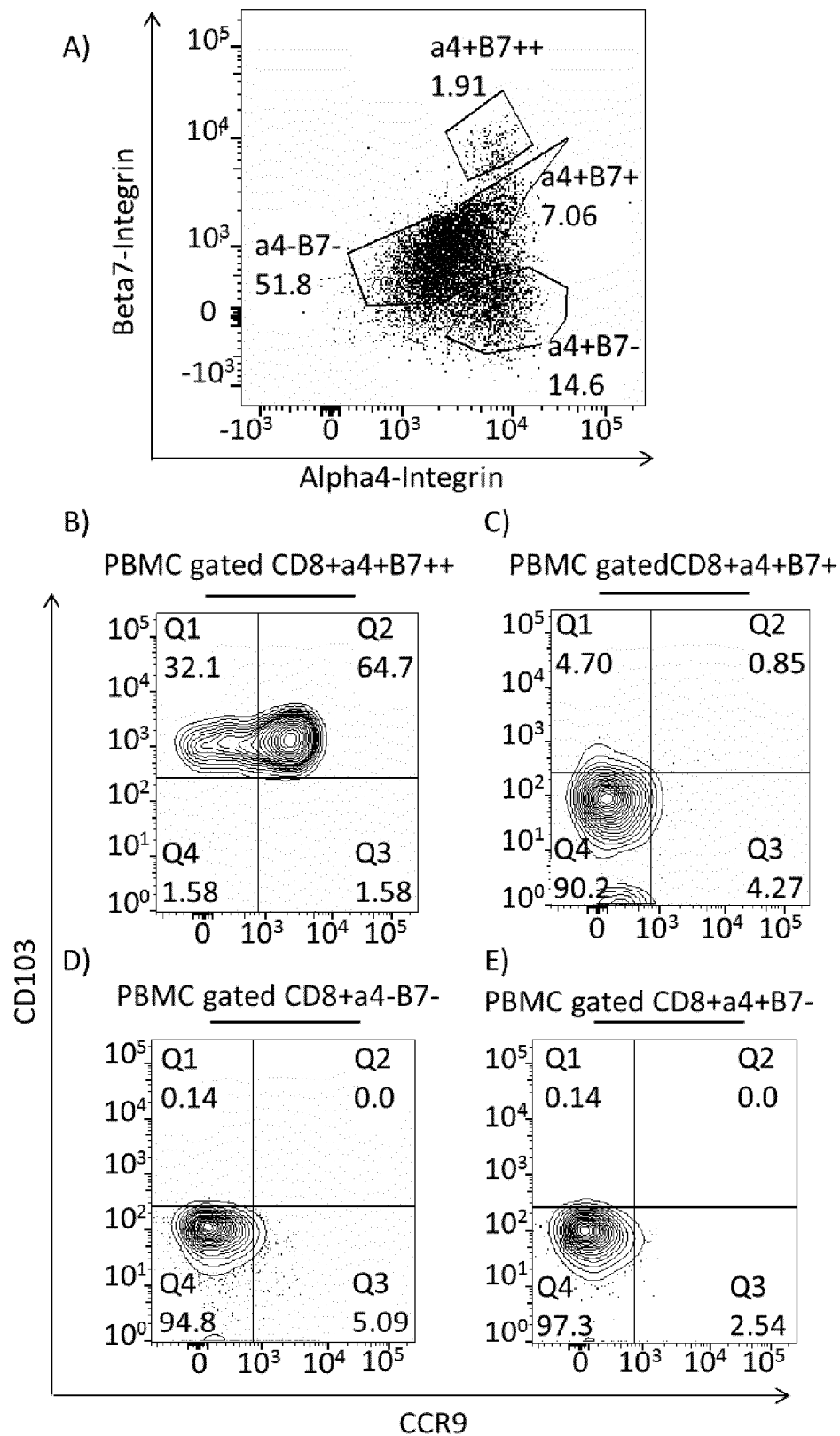

Office Action dated Mar. 13, 2018 in U.S. Appl. No. 15/303,871 (US 2017-0038395).
Brusko, "Human Regulator T cells: role in autoimmune disease and therapeutic opportunities," Immunological Reviews (2008) vol. 112, pp. 371-390.
Nigam et al., "Expansion of FOXP3$^+$ CD 8 T Cells with Suppressive Potential in Colorectal Mucosa Following a Pathogenic Simian Immunodeficiency Virus Infection Correlates with Dimished Antiviral T Cell Response and Viral Control," The Journal of Immunology, vol. 184, No. 4, pp. 1690-1701, Jan. 2010.
Office Action dated Aug. 15, 2018 in U.S. Appl. No. 15/303,869 (US 2017-0038394).
Office Action dated Aug. 27, 2018 in U.S. Appl. No. 15/303,869 (US 2017-0038394).
Office Action dated Oct. 2, 2019 in U.S. Appl. No. 15/303,866 (US 2017-0035808).
Office Action dated Sep. 13, 2019 in U.S. Appl. No. 15/303,869 (US 2017-0038394).
Office Action dated Dec. 20, 2019 in U.S. Appl. No. 15/303,871 (US 2017-0038395).
Office Action dated Mar. 5, 2020 in U.S. Appl. No. 15/303,866 (US 2017-0035808).

\* cited by examiner

Figure 18

| Marker | % pos CD8+CD103- | % pos CD8+CD103+ | Marker Y-/Y+ condition | Marker class |
|---|---|---|---|---|
| CD25 | 3,38 | 60,3 | Y+ | 1 |
| CD31 | 92,1 | 65,2 | Y- | 2 |
| CD35 | 13,8 | 35,4 | Y+ | 2 |
| CD39 | 2,37 | 17,7 | Y+ | 2 |
| CD41a | 11,6 | 33,3 | Y+ | 2 |
| CD58 | 35,2 | 98,5 | Y+ | 1 |
| CD63 | 19 | 36,4 | Y+ | 2 |
| CD66 | 59,4 | 30,4 | Y- | 3 |
| CD73 | 4.46 (hi) | 41,6(hi) | Y+ | 1 |
| CD85 | 16,5 | 1,67 | Y- | 2 |
| CD88 | 20,7 | 47 | Y+ | 2 |
| CD95 | 28,6 | 100 | Y+ | 1 |
| CD97 | 13,8 | 57,1 | Y+ | 2 |
| CD105 | 1,63 | 91,6 | Y+ | 1 |
| CD107a | 16,1 | 78,8 | Y+ | 1 |
| CD107b | 16 | 52,5 | Y+ | 1 |
| CD108 | 30,1 | 51,9 | Y+ | 2 |
| CD120b | 18,9 | 45,1 | Y+ | 2 |
| CD122 | 30,8 | 78,3 | Y+ | 1 |
| CD126 | 63,7 | 40,2 | Y- | 3 |
| CD127 | 36.3(hi) | 82.8(hi) | Y+ | 2 |
| CD130 | 67,7 | 21,5 | Y- | 2 |
| CD132 | 54,9 | 92,9 | Y+ | 2 |
| CD150 | 14,5 | 55,4 | Y+ | 3 |
| CD151 | 17,8 | 53,4 | Y+ | 2 |
| CD161 | 14,5 | 25 | Y+ | 3 |
| CD195 | 28,3 | 60 | Y+ | 3 |
| CD200 | 18 | 1,75 | Y- | 3 |
| CD210 | 21,8 | 69,2 | Y+ | 2 |
| CD221 | 56,1 | 22,7 | Y- | 2 |
| CD226 | 44,6 | 89,5 | Y+ | 2 |
| CD244 | 35,7 | 86 | Y+ | 1 |
| CD268 | 8,9 | 75,7 | Y+ | 1 |
| CD274 | 7,09 | 51,3 | Y+ | 1 |
| CD279 | 23,8 | 46,2 | Y+ | 3 |
| CD335 | 44,4 | 9,68 | Y- | 2 |
| CD336 | 45,6 | 7,02 | Y- | 2 |
| EGF-R | 41,8 | 5,33 | Y- | 2 |

CD8+ REGULATORY T-CELLS FOR USE IN THE TREATMENT OF INFLAMMATORY DISORDERS OF THE HUMAN GASTROINTESTINAL TRACT

FIELD OF THE INVENTION

The present invention relates to cellular immunotherapy, in particular cellular immunotherapy with T-regulatory cells (Treg) for the treatment of inflammatory disorders of the human gastrointestinal tract including Crohn's disease and inflammation of the small bowel. The invention also relates to specific Treg cells and identification of immunosuppressive regulatory T-cells and to a method for expanding such cells.

BACKGROUND OF THE INVENTION

Inflammatory Bowel Disease (IBD) consists of two major types, namely Crohn's Disease (CD) and Ulcerative Colitis (UC). The number of new cases diagnosed per year, denoted annual incidence, of CD is 12-20 per 100,000 persons in Europe and North America. The numbers are 6 and 5 per 100,000 persons, respectively for Asia and the Middle East. New Zealand and Australia have the highest incidence figures, calculated to 27 and 50 per 100 000, respectively.

CD affects any part of the gastrointestinal tract, from mouth to anus, although in the majority of the cases the disease starts in the distal small bowel. CD involves the whole bowel wall (transmural inflammation). UC is restricted to inflammation in the colon and involves only the mucosa. UC has somewhat higher incidence figures than CD. There is a relationship between UC and CD by the fact that for about 15% of patients with colonic inflammation the diagnoses cannot be histopathologically distinguished. These patients are classified as having Indeterminate Colitis.

Common symptoms associated with IBD are abdominal pain, vomiting, diarrhoea, rectal bleeding, weight loss and cramps or spams in the lower abdomen. In severe cases the tendency to develop intra-abdominal fistulas gives rise to deep infections. Longstanding inflammation may lead to intestinal strictures. Surgical treatment usually involves percutaneous drainage of deep abscesses followed by surgery with resection of diseased bowel segments. Diagnosis is generally assessed by inflammatory markers in blood and stool, followed by ileo-colonoscopy with biopsies of pathological lesions.

First hand medical treatment consists of antibiotics and anti-inflammatory medication. There are several anti-inflammatory drugs, of which cortisone, azathioprine and antibodies against TNF are the most frequently used. Even if a positive response is seen both short- and long-term, these medications often lead to adverse reactions and patients often need to reduce the dose to a minimum or taper them out completely.

Both CD and UC as inflammatory disorders have long been considered as a breakdown in immunoregulation in the tissues of the intestinal mucosa, representing the most immunologically active sites of the human body. The interaction between luminal flora and the adaptive immune system is considered critical to disease pathogenesis. T-cells are central to cell-mediated adaptive immunity. Two main subdivisions of T-cells may be defined, were T-effector cells (Teffs) can be generalised to represent proinflammatory activities, and Tregs to represent an anti-inflammatory check. Exuberant Teff activity is observable in both animal models and human disease alike, and has been attributed in recent years to a breakdown in Treg-mediated homoeostatic mechanisms. However, it remains difficult to attribute IBD immunopathogenesis to any specific functional or numerical defect in Tregs themselves. This is in no small part due to the fact that proposed in vivo mechanisms of Treg function in humans remain largely speculative. Regardless, numerous animal models and early clinical experiences have suggested that Treg cells could be harnessed for treatment of a range of inflammatory disorders, and particularly IBD.

T-cells impart control locally; individually influencing control of immune responses over relatively short distances. Consequently, the migration of T-cells between intestinal mucosa and other bodily compartments is a critical determinant of functional responses. Several large-scale clinical trials have focused on blocking Teff migration to intestinal tissues through pharmaceutical blockade of either adhesion molecules or chemoattractants critical of T-cell migration to intestinal mucosa, with mixed success.

A majority of the knowledge around the T-cell pathology of IBD is inferred from mouse models. It is well established that transfer of nave conventional CD4+ T-cells into immune deficient mice results in a reaction against intestinal flora and establishment of intestinal inflammation, which can be rescued by co-transfer of Treg populations. It is also clear that Treg transfer into mice can resolve established intestinal inflammation. In the human setting, early indications of the correlation between intestinal tolerance and the human autoimmune syndrome were linked with FOXP3 mutations, the most common manifestation of which is chronic intestinal inflammation.

An accumulating body of data in patients with active and inactive IBD, and under various treatments, has yielded disparate results. Early studies suggested that the (lamina propria) LP of both CD and ulcerative colitis (UC) patients contained functional Tregs. Some studies have reported increased levels of Tregs in inflamed LP of IBD patients.

Considering the importance of migration of cells between the periphery and mucosal tissues, it is critical to consider the peripheral Treg pool in relation to direct observations of the inflamed mucosa. Several early studies have reported decreased levels of peripheral CD4+ Treg cells in patients with active intestinal inflammation. However, the opposite has also been observed, with an increased frequency of peripheral CD4+ Tregs in IBD patients, though lower frequency is often observed in active when compared to inactive disease.

Studies investigating Treg response in IBD patients undergoing anti-tumour necrosis factor (anti-TNF) therapies have reported increased levels of peripheral Tregs, particularly among clinical responders. However, other studies have reported no change in peripheral Treg frequency, and even a decreased frequency. Similar studies in rheumatoid arthritis have shown that responders to anti-TNF and methotrexate therapies show increased numbers of peripheral Treg cells. Curiously, addition of anti-TNF drugs to activated T-cells from patients resulted in the generation of Treg cells in vitro.

In summary, while it may be generally anticipated that IBD is characterised by a breakdown of immunotolerance in the intestinal mucosa, there is a lack of consistent correlation with an impaired Treg function or diminished abundance in patient tissues. This may be a result of as yet crude analytical methods to identify Treg cells, discriminate Treg subsets, and to assay their functional properties. It is also likely a function of still incomplete understanding of Treg origin and function in intestinal immune homeostasis. Recent insights into T-cell immunity in the intestinal mucosa have come from more detailed studies of T-cell migration and induction in the periphery.

However, there is a need to identify Treg cells that are suitable for use in cellular immunotherapy for the treatment of inflammatory and autoimmune diseases, notably IBD.

DESCRIPTION OF THE INVENTION

The present invention addresses the above-mentioned needs. The present invention aims to identify Treg cells with unique characteristics suitable for the above-mentioned uses, and particularly selected for treatment of inflammatory and autoimmune diseases of defined tissues relating to the gastrointestinal tract.

Different forms of $CD8^+$ Tregs may be considered. One may divide $CD8^+$ Tregs into two main types, natural Tregs (nTregs) and induced Tregs (iTregs). This subdivision considers all Tregs that come from the selection of self-antigens in the thymus followed by emigration from the thymus to peripheral circulation as 'naturally' occurring nTregs. These nTregs are considered to be general drivers of self-tolerance, as they are raised against abundant self-antigens via high avidity interactions in the thymus. In contrast, iTregs are raised against antigens in the periphery from naive conventional T-cells. In the case of the intestinal mucosa, iTregs are likely to be raised primarily against foreign antigens such as those from food, and antigens arising from abundant commensal bacteria residing in the lumen. In this conception, iTregs represent the primary drivers of T-cell tolerance, for instance, towards foodstuffs and symbiotic bacteria. However, this subdivision between iTregs and nTregs in humans is largely conceptual, as they are practically very difficult to distinguish by surface markers, where their existence is ultimately inferred from interventional mouse experiments. To date, it has been difficult to address questions regarding nTreg and iTreg form and function in humans in any reliable and systematic manner due largely to practical limitations.

The primary focus of Treg research in the area of IBD has been on CD4+ Tregs. In recent years it has been appreciated that CD8+ cells also possess regulatory function, however, there is sparse investigation of the participation of CD8+ Tregs in IBD pathophysiology. To date, CD28, CD122 and CD103 have been most commonly used to define Tregs in mouse and man.

$CD8^+$ Tregs may be divided into the two main subsets on thymic-derived nTregs and peripherally induced iTregs, much like $CD4^+$ Tregs. However, few reliable surface markers are available to discriminate $CD8^+$ Tregs from their cytotoxic counterparts.

The current invention relates to leveraging on observed migratory patterns of CD8+ Treg cells in IBD patients, which allows identification of activated mucosal Treg subpopulations that may be purified as starting material for manufacture of cellular immunotherapeutic products.

The present invention provides Treg cells with unique characters suitable for the above-mentioned use.

The present invention is based on the findings that specific homing receptor expression patterns can be used to identify $CD8^+$ regulatory T-cells in peripheral circulation as starting materials for therapeutic composition. The specific homing receptor expression pattern varies from tissue to tissue, but it is contemplated that the nature of the signatures (expression pattern) is the same, irrespective of the diseased tissue in question. Thus, the present invention is based on the surprising findings that e.g. Crohn's disease is not a disease defined by a deficiency of Tregs per se, but a deficiency in their ability to recirculate to the diseased tissue, in this case the small bowel. Significantly fewer recent mucosal emigrants and recirculating T-cells were observed in the peripheral blood and diseased tissues of patients (as defined by CD103 and CCR9 expression). These findings have led to identification of $CD8^+$ Treg subtypes by surface marker signatures, that may be used in order to purify $CD8^+$ Treg cells suitable for therapeutic use.

It was observed that Treg cells obtained from patients suffering from CD have markedly diminished CCR9 marking on Tregs. CCR9 expression is induced within the small bowel lymphoid tissues in parallel with antigen engagement. Export of CCR9-expressing Tcells from the mucosal lymphoid tissues allows recirculation of these cells to regional mucosal tissue. This process is important for establishment of regional and subsequently systemic tolerance. It is anticipated that by targeting varying mucosal tropic and emigrant Treg populations, that the T-cell receptor clonotypes of these populations are restricted to those relevant to tissue-related and disease-related antigens.

These findings suggest that $CD8^+$ Tregs with a specific expression pattern are useful in the treatment of inflammatory diseases of the gastrointestinal tract. The Treg cells should have specific signatures that
i) identify that the cells are $CD8^+$ regulatory T-cells,
ii) identify that the regulatory T-cells are tissue type tropic, i.e. they can migrate to the diseased tissue type,
iii) optionally, identify that the Treg cells are diseased tissue tropic, i.e. they are so-called homing cells that can localize in the diseased region of the gastrointestinal tract,
iv) identify that the regulatory T-cells are emigrant cells, i.e. they originate from the target tissue (educated cells), and
v) optionally, identify that the regulatory T-cells are retained in the target tissue after administration to a subject,
wherein the T-cells have the signatures i), ii) and iv) and optionally iii) and/or v); or the T-cells have the signatures i), ii), iv) and v) and optionally iii), or the T-cells have the signatures i), ii), iv) and v), and optionally iii).

In the present context the term "tissue type" means the specific type of tissue present in the diseased area. As an example the tissue type in relation to Crohn's disease in the small bowel is mucosa and the mucosa is healthy or diseased tissue from the gastrointestinal tract, i.e. the tissue type is not narrowly defined as being exactly from the diseased mucosa, but may be from another part of the gastrointestinal tract. In preferred aspect the tissue type is from the diseased tissue.

In the present context the term "target tissue" means the specific type of tissue present in the diseased area. As an example the target tissue in relation to Crohn's disease in the small bowel is mucosa from the small bowel.

In the present context the terms "tissue type tropic" and "diseased tissue tropic" denotes tropism in relation to the "tissue type" (i.e. tissue in general) and in relation to the "target tissue" (i.e. specific diseased tissue region), respectively. The tropism may be to the diseased tissue as well as to the healthy tissue in the diseased area, tissue region or tissue type. It should be noted that immigration of cells from peripheral blood into the stromal/parenchyma of any tissue is mediated by factors intrinsic to the tissue itself, and by factors presented by the vasculature permeating said the tissue. As such, tissue tropism is an interaction of factors expressed by migratory cells with both tissue-centric and tissue vasculature-centric factors. This duality results in often-significant overlap in the functional elements of migratory cells with tropism towards related yet distinct tissue types and tissue subtypes.

The specific types of Tregs in accordance with the concept of the present invention are described in detail herein. It is contemplated that the Treg cells are suitable for use in the treatment of inflammatory diseases of the gastrointestinal tract and the particular proof of concept relates to inflammation of the small bowel in particular, but through mucosal tropism also for inflammatory diseases located in the whole mucosal gastrointestinal tract.

As mentioned above CD can affect the whole gastrointestinal tract, notably the distal part of the small bowel, the colon, the proximal part of the gastrointestinal tract or the anal canal and perianal area. It is envisaged that the Treg cells suitable for use in the treatment of CD mainly have the same signatures irrespective of which part of the gastrointestinal tract that is affected apart from the signature that identifies that the regulatory T-cells are gastrointestinal tropic. It is believed that the signature in this respect must be specific, i.e. proximal gastrointestinal tract tropic, large bowel tropic, small bowel tropic, anal canal tropic etc. dependent on the localisation of CD.

The present invention has a proof of concept based on specific Treg cells for use in the treatment of CD. The CD8$^+$ Treg cells should have specific signatures that
i) identify that the cells are regulatory T-cells,
ii) identify that the regulatory T-cells are tissue type tropic, in this case mucosal tropic, i.e. they can migrate to the diseased tissue (mucosa),
iii) optionally, identify that the Treg cells are diseased tissue tropic, in case of CD in the small bowel the Treg cells are small bowel tropic, i.e. they are so-called homing cells that can localize in the small bowel,
iv) identify that the regulatory T-cells are emigrant cells, i.e. they originate from the target tissue, i.e. Tregs originate from the mucosa (educated cells), and
v) optionally, identify that the regulatory T-cells are retained in the diseased tissue (the small bowel) after administration to a subject.

As seen from the above the signatures i), ii) and iv) are mandatory when the Tregs are used in the treatment of CD in the small bowel. However, it is contemplated that different treatment strategies, or treatment of inflammatory diseases such as Crohn's disease affecting other parts of the gastrointestinal tract do not require the same signatures; thus, it is contemplated that the Tregs must have the signatures i), ii) and iv) and optionally iii) and/or v); or the T-cells have the signatures i), ii), iv) and v) and optionally iii), or the T-cells have the signatures i), ii), iv) and v) and optionally iii).

In analogous manner when the CD is localized in the colon the Treg cells should have specific signatures that
i) identify that the cells are regulatory T-cells,
ii) identify that the regulatory T-cells are mucosal tropic, i.e. they can migrate to the diseased tissue (mucosa),
iii) optionally, identify that the Treg cells are colon tropic, i.e. they are so-called homing cells that can localize in the colon, or specifically the diseased segment of the colon,
iv) identify that the regulatory T-cells are emigrant cells, i.e. they originate from the target tissue, i.e. from the mucosa, (educated cells), and
v) optionally, identify that the regulatory T-cells are retained in the target tissue, i.e. the colon, after administration to a subject.

Tregs for treatment of CD in other locations of the gastrointestinal tract have the same kind of signatures, but relating to the diseased part of the gastrointestinal tract.

In general CD8$^+$ Treg cells are defined as a type cell that negatively regulates proinflammatory immune responses.

There are currently no ubiquitous markers that define CD8$^+$ Tregs. Indeed, this is likely a reflection of the existence of many functionally and locally distinct CD8$^+$ Treg subsets. CD8$^+$ Tregs can conceptually be divided into two forms. The induced Tregs, which develops from mature T-cells in periphery, and the natural Tregs, which develops from immature T-cells in the thymus.

The present inventors have found that specific homing receptor expression patterns can be used to identify Treg cells in peripheral circulation as starting materials for therapeutic applications. These Treg cells are characterized by the expression of CD8+. There is a fundamental difference between CD4 and CD8 cells. CD4 cells in general engage with MHCII-antigen complexes, while CD8 engage MHCI-antigen complexes. In this sense, CD4 cells can be considered to engage antigens derived extrinsically to the cell, while CD8 engage antigens derived intrinsically.

It was not until recently that CD8 cells were considered to contain regulatory subsets. There have been several markers proposed to partly define CD8 Tregs, or at least subsets of CD8 Tregs. These include FOXP3, similar to that of CD4 Tregs, CD28, CD122 and CD103. Based on experiments, the present inventors identified CD8$^+$ Tregs that were positive for CD103 ($\alpha$E). Thus, it was considered likely that this is simply coincidental to the observation that a large proportion of CD8$^+$ Tregs have a propensity to dominantly recirculate to the small intestine as part of homeostatic self-tolerance mechanisms. Indeed, a significant proportion of CD8$^+$ T-cells expressing mucosal tropic and retention makers are involved with the small intestinal mucosa as indicated by CCR9 and particular integrin expression. These mucosal-tropic and -emigrant CD8+ Tcell populations may be dominated by Treg subsets due to the fact that this is largest site of direct interaction between pathogenic and commensal antigens and the adaptive immune system, and these putatively self-reactive CD8+ Tregs underpin homeostatic immune tolerance in the mucosa.

As described in the examples herein, it was studied whether small-intestinal homing and retention phenotype is indicative of CD8 Treg characteristics in the peripheral blood of healthy donors. FIG. 1 presents an analysis of peripheral CD8 cells and shows high proportion of CD8 cells contained within the $\alpha 4^+\beta 7^{high}$ gate. While approximately 2% of all CD8 cells carry this integrin phenotype, less than 0.02% of CD4 cells carry $\alpha 4^+\beta 7^{high}$. The variance of this value is high for CD4 cells, with as few as 0.002% of CD4 cells observed to carry the $\alpha 4^+\beta 7^{high}$ phenotype in some individuals.

CD8 cells with $\alpha 4^+\beta 7^{high}$ phenotype are highly enriched for both CD103 and CCR9 expression. Strikingly, CD8$^+\alpha 4^+\beta 7^{high}$ cells exclusively express CD103 (FIG. 1b to e). In the reciprocal analysis, we see that around 70% of all CD8$^+$CD103$^+$ cells are positive for $\alpha 4^+\beta 7^{high}$ phenotype (FIG. 2), a striking enrichment compared to the ~14% seen in the same analysis of CD4$^+$CD103$^+$ cells. In the case of the CD4 cells, there is a population that solely expresses $\alpha E\beta 7$ in the absence of $\alpha 4\beta 7$, a population that does not seem to exist among CD8 cells. Furthermore, a very distinct $\beta 7^{high}\alpha E^+$ population may be observed among CD8 cells in the peripheral blood (FIG. 3a), and naturally this population exclusively expresses $\alpha 4$ integrin, and is highly enriched for CCR9.

Figure 4:
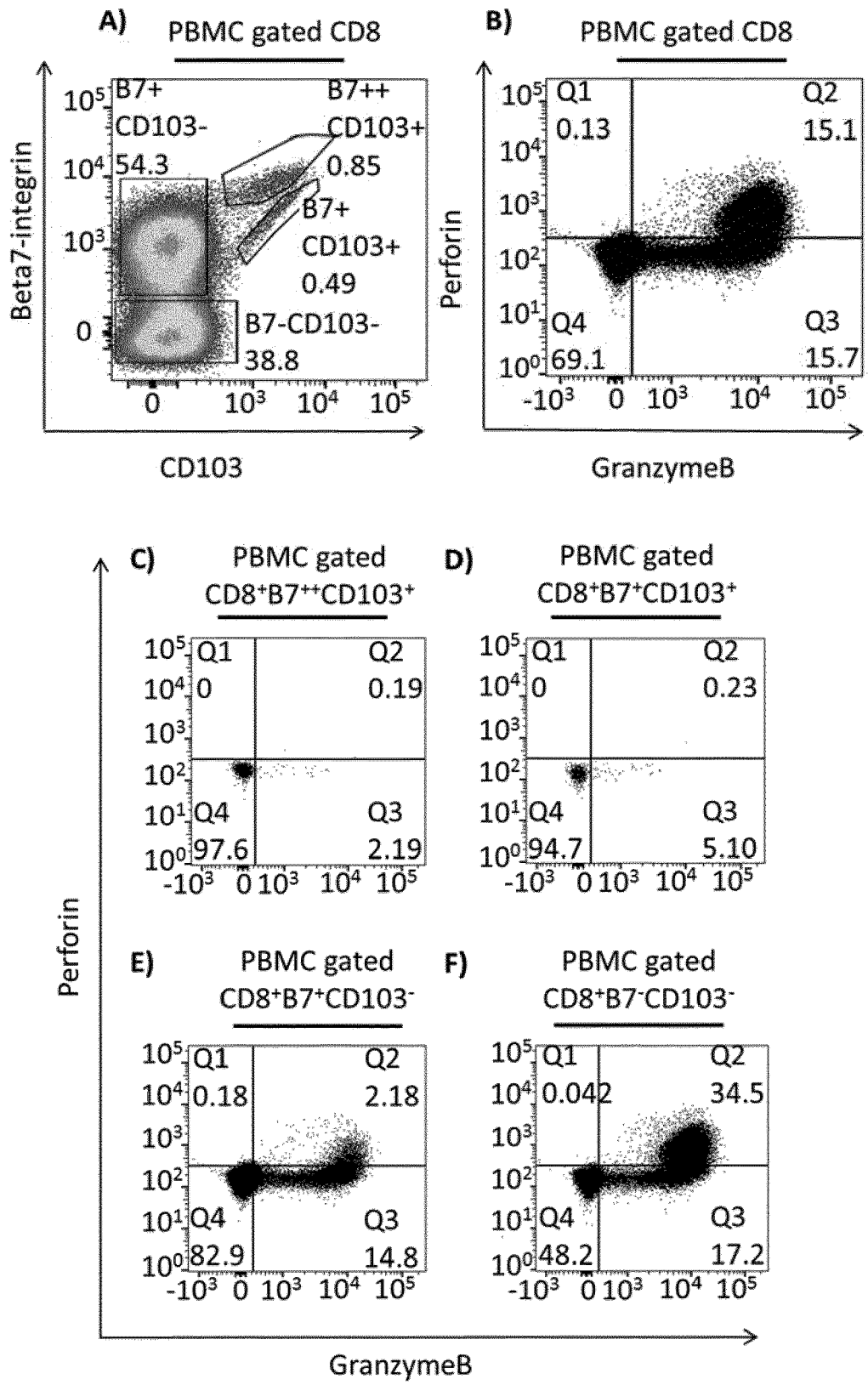

Finally, analysis of both markers of cytotoxic CD8 cells such as granzyme B and perforin show that cells of C8$^+\alpha 4^+\beta 7^{high}\alpha E^+$ character are completely lack a cytotoxic phenotype (FIG. 4). Indeed they show almost 0% cytotoxic marker expression when compared to the general CD8$^+\beta 7^-$CD103$^-$ population that carries over 50% positivity in either or both markers. This indirectly supports the Treg nature of $C8^+\alpha4^+\beta7^{high}\alpha E^+$ cells.

Figure 5:
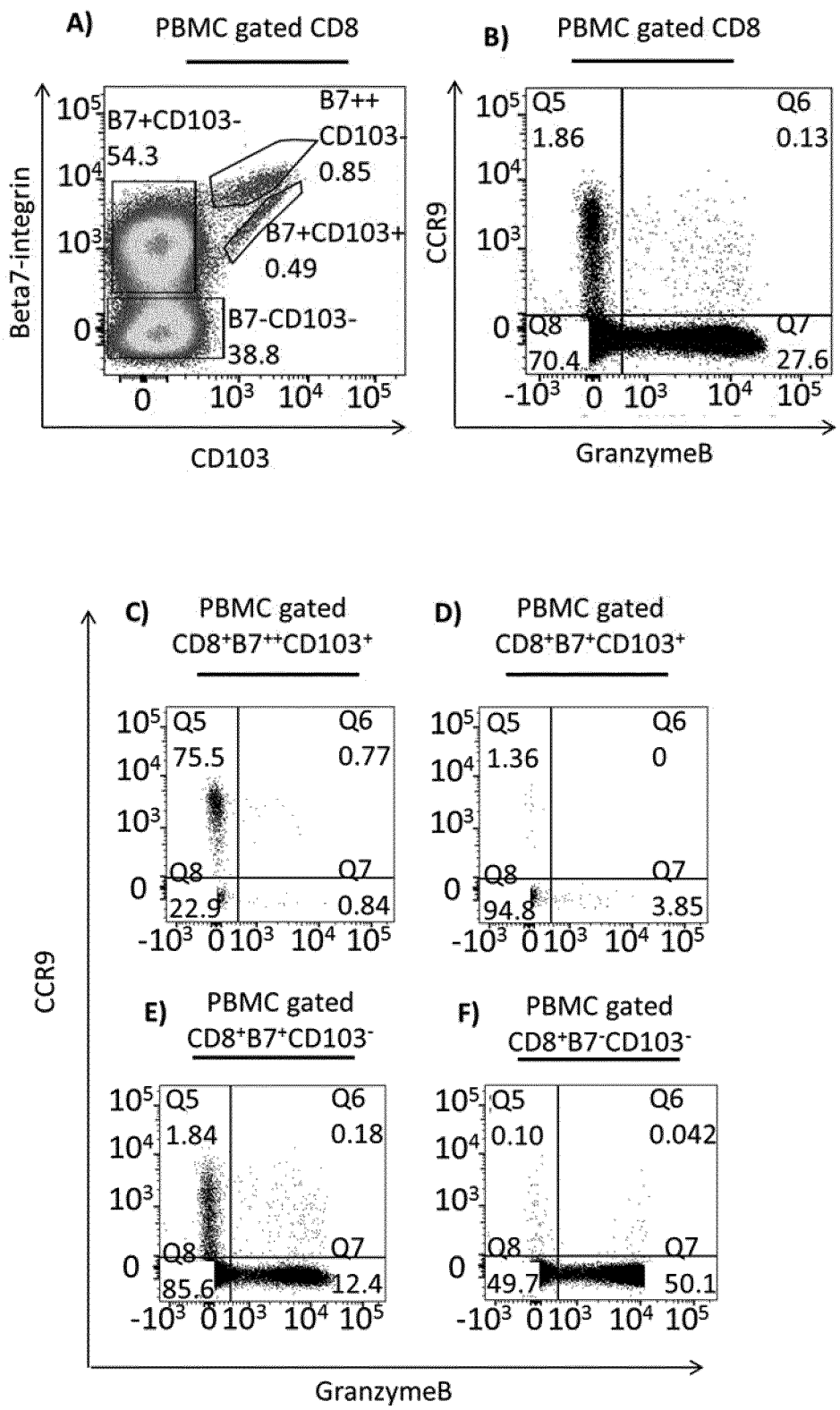

In summary, these cells of $CD8^+\alpha4^+\beta7^{high}\alpha E^+CCR9^+$ are very likely to be highly enriched for $CD8^+$ cells of a Treg nature (FIG. 5). We suggest that these CD8 Tregs represent a strong candidate for Treg cell therapies of CD.

The $CD8^+$ Treg cells should have specific signatures that
i) identify that the cells are regulatory T-cells,
ii) identify that the regulatory T-cells are tissue type tropic, in this case mucosal tropic, i.e. they can migrate to the diseased tissue (mucosa),
iii) optionally, identify that the Treg cells are diseased tissue tropic, i.e. they are so-called homing cells that can localize in the diseased tissue of the gastrointestinal tract,
iv) identify that the regulatory T-cells are emigrant cells, i.e. they originate from the target tissue, i.e. disease affected mucosa, (educated cells), and
v) optionally identify that the regulatory T-cells are retained at the target tissue of the gastrointestinal tract after administration to a subject.

The present inventors have found that a preferred signature for identifying that the Treg-enriched population of cells are mucosal tropic is $\alpha4\beta7^+$, $\alpha4^+\beta7^+$, preferably $\alpha4\beta7^+$.

A preferred signature for identifying that the Treg cells can be retained in mucosal tissue is $\alpha4^+\alpha E^+\beta7^{high}$. $\alpha4^+\alpha E^+\beta7^{high}$ in some instances may also be considered as an identifier of mucosal emigration.

The specific types of Tregs in accordance with the present invention are described in detail herein using CD localized in the small bowel as an example, but without limiting the invention thereto. It is contemplated that the Treg cells are suitable for use in the treatment of inflammatory diseases of the small bowel, especially in the treatment of CD.

If CD is located to the small bowel, the diseased as well as the target tissue is the small bowel.

Thus, the identification of a specific Treg cell population in peripheral blood, which is likely to represent mucosal emigrants with a strong propensity to recirculate to the small bowel, presents a further means to identify Treg cells based on homing receptor patterns for adoptive immunotherapy. Coupled to Treg markers and, optionally a marker set for cells marked for mucosal retention, the present inventors were able to identify four overlapping subsets of Tregs with therapeutic potential in CD located in the small bowel. Analogously, Treg cells with therapeutic potential in CD located in other parts of the gastrointestinal tract can be identified or Tregs with therapeutic potential in other inflammatory diseases of the gastrointestinal tract.

1. $CD8^+$ Treg cells that have signatures for
i) identifying that the T-cells are regulatory T-cells,
ii) identifying that the Treg cells are mucosal tropic, i.e. they can migrate to mucosal tissue,
iv) identifying that the Treg cells are emigrant cells, i.e. they originate from the bowel.

2. $CD8^+$ Treg cells that have signatures for
i) identifying that the T-cells are regulatory Tcells,
ii) identifying that the Treg cells are mucosal tropic, i.e. they can migrate to mucosal tissue,
iii) identifying that the Treg cells are small bowel tropic, i.e. homing cells that can localize in the small bowel, and
iv) identifying that the Treg cells are emigrant cells, i.e. they originate from the bowel.

3. $CD8^+$ Treg cells that have signatures for
i) identifying that the T-cells are regulatory Tcells,
ii) identifying that the Treg cells are mucosal tropic, i.e. they can migrate to mucosal tissue,
iv) identifying that the Treg cells are emigrant cells, i.e. they originate from the bowel. and
v) identifying that the Treg cells are marked for mucosal retention.

4. $CD8^+$ Treg cells that have signatures for
i) identifying that the T-cells are regulatory Tcells,
ii) identifying that the Treg cells are mucosal tropic, i.e. they can migrate into mucosal tissue,
iii) identifying that the Treg cells are small bowel tropic, i.e. homing cells that can localize in the small bowel,
iv) identifying that the Treg cells are emigrant cells, i.e. they originate from the bowel, and
v) identifying that the Treg cells are marked for mucosal retention.

As mentioned herein before, the preferred $CD8^+$ Treg cells are $CD8^+$ Treg cells that have signatures for
i) identifying that the T-cells are regulatory Tcells,
ii) identifying that the Treg cells are mucosal tropic, i.e. they can migrate into mucosal tissue,
iii) optionally, identifying that the Treg cells are small bowel tropic, i.e. homing cells that can localize in the small bowel,
iv) identifying that the Treg cells are emigrant cells, i.e. they originate from the bowel, and
v) optionally identifying that the Treg cells are marked for mucosal retention.

Other alternatives may be derived from the description herein.

As will be explained in detail herein, the preferred signature for identifying that the T-cells are regulatory T-cells is $CD8^+$ and $CD122^+$, or $CD8^+Y_n$, where Y is a functional marker and n is an integer of 1 or more. Functional markers Y are described herein below, for example.

The preferred signature for identifying that the Treg cells are mucosal tropic is $\alpha4\beta7^+$ or $\alpha4^+\beta7^+$, or in combination with one or more X signatures as defined herein.

The preferred signature for identifying that the Treg cells are small bowel tropic, i.e. homing cells, is $CCR9^+$ or in combination with one or more X signatures as defined herein.

The preferred signature for identifying that the Treg cells are mucosal antigen educated cells (emigrants) includes $CD62L^-$, $\alpha4^+\alpha E^+ \beta7^{high}$, and/or one or more X signatures and/or one or more Y signatures as defined herein.

The preferred signature for identifying that the Treg cells can be retained in mucosal tissue is $\alpha4^+\alpha E^+\beta7^{high}$ or $\alpha4^-\alpha E^+\beta7^+$.

Other signatures are $CD45RA^-/CD45RO^+$, or $CCR7^-$.

Thus, in an aspect of the invention relating to inflammatory or autoimmune diseases of the gastrointestinal tract, notably the small bowel, the method provides Treg cells that are selected from the following populations:

$CD8^+\alpha4\beta7^+CD62L^-$
$CD8^+\alpha4^+\beta7^+CD62L^-$
$CD8^+\alpha4\beta7^+CD62L^-CCR9^+$
$CD8^+\alpha4^+\beta7^+CD62L^-CCR9^+$
$CD8^+\alpha4\beta7^{high}\alpha E^+CD62L^-$
$CD8^+\alpha4^+\beta7^{high}\alpha E^+CD62L^-$
$CD8^+CD62L^-\alpha4\beta7^{high}\alpha E^+CCR9^+$
$CD8^+CD62L^-\alpha4^+\beta7^{high}\alpha E^+CCR9^+$ In all the specific Treg cell populations described herein (such as those mentioned above) it is within the scope of the present invention that whenever
a) $CD8^+$ is mentioned it may be replaced with $CD8^+CD122^+$, b) CD62L⁻ is mentioned this signature may be replaced or supplemented with $\alpha4^+\alpha E^+\beta7^{high}$, and whenever) $\alpha4^+\beta7^{high}\alpha E^+$ is mentioned it may be replaced with $\alpha4^+\beta7^+\alpha E^+$.

As described herein in details the above CD8⁺ Treg cells may comprise one or more further signatures relating to the emigrant and/or immigrant nature of the CD8⁺ Treg cells. Such signatures are denoted "X", where X is the signature indicating that the Tregs can localize, has emigrated from, or is marked for preferential retention in the specific part of the gastrointestinal tract that is diseased. As explained herein examples of signatures X are given in FIG. 16. The CD8⁺ Treg cells may also comprises signatures of functional nature, Y. However, as explained herein signatures relating to emigrant cells from thymus and immigrant cells from the peripheral blood to the lymph nodes should be excluded. In other preferred aspects of such an invention and relating to CD in other parts of the gastrointestinal tract than the small bowel, the Treg cells are selected from the following:

CD8⁺$\alpha4\beta7^+$CD62L⁻X
CD8⁺$\alpha4^+\beta7^+$CD62L⁻X
CD8⁺$\alpha4\beta7^+$CD62L⁻CCR9⁺X
CD8⁺$\alpha4^+\beta7^+$CD62L⁻CCR9⁺X
CD8⁺$\alpha4\beta7^{high}\alpha E^+$CD62L⁻X
CD8⁺$\alpha4^+\beta7^{high}\alpha E^+$CD62L⁻X
CD8⁺CD62L⁻$\alpha4\beta7^{high}\alpha E^+$CCR9⁺X
CD8⁺CD62L⁻$\alpha4^+\beta7^{high}\alpha E^+$CCR9⁺X where X is the signature indicating that the Tregs can localize, has emigrated from, or is marked for preferential retention in the specific part of the gastrointestinal tract that is diseased. X may be X⁺ or X may be X⁻. At least one X may be present.

As mentioned above, the Treg cells may also contain a signature Y. Y is the signature indicating that the CD8⁺ cells possess immunosuppressive regulatory functions, or are restricted for pro-inflammatory activities. Y signature indicates regulatory function, such a signature is required in aspect i) in marking target CD8⁺ Treg identity, and thus, such Treg cells are:

CD8⁺$\alpha4\beta7^+$CD62L⁻Y
CD8⁺$\alpha4^+\beta7^+$CD62L⁻Y
CD8⁺$\alpha4\beta7^+$CD62L⁻CCR9⁺Y
CD8⁺$\alpha4^+\beta7^+$CD62L⁻CCR9⁺Y
CD8⁺$\alpha4\beta7^{high}\alpha E^+$CD62L⁻Y
CD8⁺$\alpha4^+\beta7^{high}\alpha E^+$CD62L⁻Y
CD8⁺CD62L⁻$\alpha4\beta7^{high}\alpha E^+$CCR9⁺Y
CD8⁺CD62L⁻$\alpha4^+\beta7^{high}\alpha E^+$CCR9⁺Y
CD8⁺$\alpha4\beta7^+$CD62L⁻XY
CD8⁺$\alpha4^+\beta7^+$CD62L⁻XY
CD8⁺$\alpha4\beta7^+$CD62L⁻CCR9⁺XY
CD8⁺$\alpha4^+\beta7^+$CD62L⁻CCR9⁺XY
CD8⁺$\alpha4\beta7^{high}\alpha E^+$CD62L⁻XY
CD8⁺$\alpha4^+\beta7^{high}\alpha E^+$CD62L⁻XY
CD8⁺CD62L⁻$\alpha4\beta7^{high}\alpha E^+$CCR9⁺XY
CD8⁺CD62L⁻$\alpha4^+\beta7^{high}\alpha E^+$CCR9⁺XY wherein at least one Y, and/or at least one of X and at least one of Y is present, and X may be X⁺ or X⁻, and Y may be Y⁺ or Y⁻. X and Y are as defined above.

The CD8⁺ Treg cells may also contain the signatures CD38⁺, CD69⁺ and/or CD44⁺ to denote recent activation.

As described in the experimental part herein it was found that $\beta7^{hi}$ cells express higher levels of $\beta7$ owing to the fact that they require additional $\beta7$ to pair with $\alpha E$, suggesting $\beta7^{hi}$ cells express both the $\alpha4\beta7$ and $\alpha E\beta7$ integrin pairs. The significance of this is that $\alpha4\beta7$ is thought to be required for migration into mucosal tissues, while $\alpha E\beta7$ is required for retention. $\alpha E\beta7$ may also in some instances be considered to represent an identifier of recent mucosal emigration.

As mentioned above, the present invention relates to specific Tregs for treating inflammatory disorders of the bowel. To this end it is important to identify important subtypes of Treg cells, enabling their accurate purification from human tissues. This knowledge has been built on unique analyses of specimens from patients with CD, healthy individuals, and in some respects from patients with colorectal cancer.

With regard to marker X in the above claims, relating to markers that denote a signature indicating tissue localisation, emigration or immigration, further analyses reveal markers of particular interest.

Figure 16:
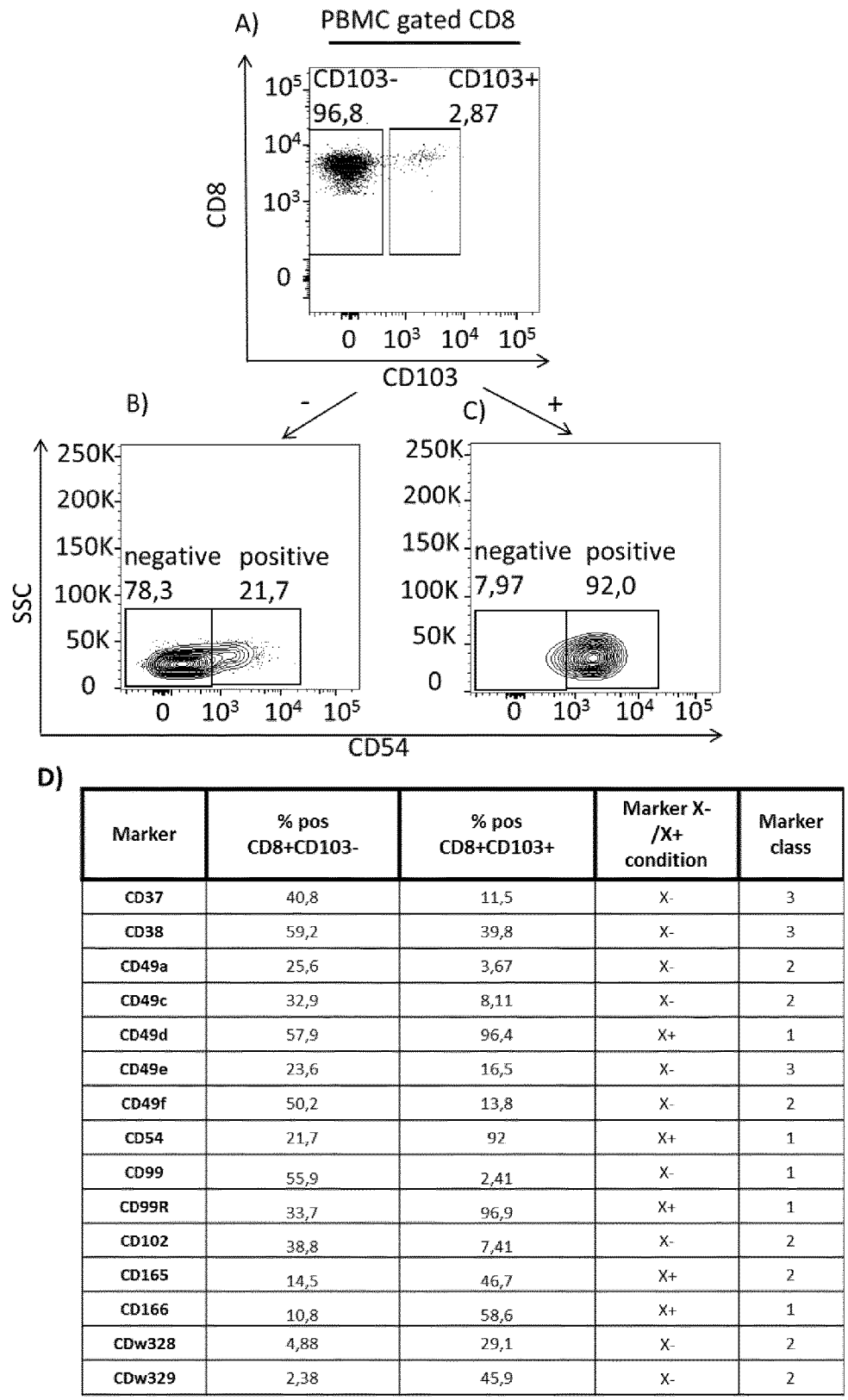

FIG. 16 shows an example of enriched adhesion molecule enrichment in the CD8⁺CD103⁺ population (FIG. 16 *a* to *c*). In this example, CD54 (ICAM-1) is highly enriched in the CD8⁺CD103⁺ population. It is thus anticipated that CD54 may be used as a marker of preferred condition X⁺, with which to select for mucosal emigrant, immigrant and activated CD8⁺ Treg cells. The table presented as FIG. 16*d* summarises other migratory-type markers associated with the CD8⁺CD103⁺ population. The markers negatively correlated are of condition X⁻, where in the preferred aspect they are used as a negative selection marker for the purification of CD8⁺ mucosal emigrant, immigrant and activated CD8⁺ Treg cells. Each marker in this table is also assigned a class, where class 1 represents a strong association with the CD8⁺CD103⁺ population and high functional significance. Class 2 represents a strong association with the CD8⁺CD103⁺ population or high functional significance. Class 3 represents weak association and/or uncertain functional significance.

The aforementioned markers relate to tissue localisation, emigration, immigration and retention. It is anticipated that the identified populations are highly enriched for CD8⁺ T-cells that are regulatory in nature. Further analyses have revealed a strong enrichment of markers on the surface of the identified cell populations that denote regulatory function, and a restriction of markers that generally denote pro-inflammatory functions. Any of these markers, X, can be included in a CD8⁺ Treg cell population according to the invention or used in a method of the invention to select the right signature pattern on the CD8⁺ Treg cells. As shown in FIG. 16, markers of class 1 include: CD49d, CD54, CD99, CD99R and CD166. Markers of class 2 include: CD49a, CD49c, CD49f, CD102, CD165, CDw328, and CDw329. Markers of class 3 include CD37, CD38, and CD49e. One or more of these markers may be included as signatures for the CD8⁺ Tregs relevant for the invention.

Figure 17:
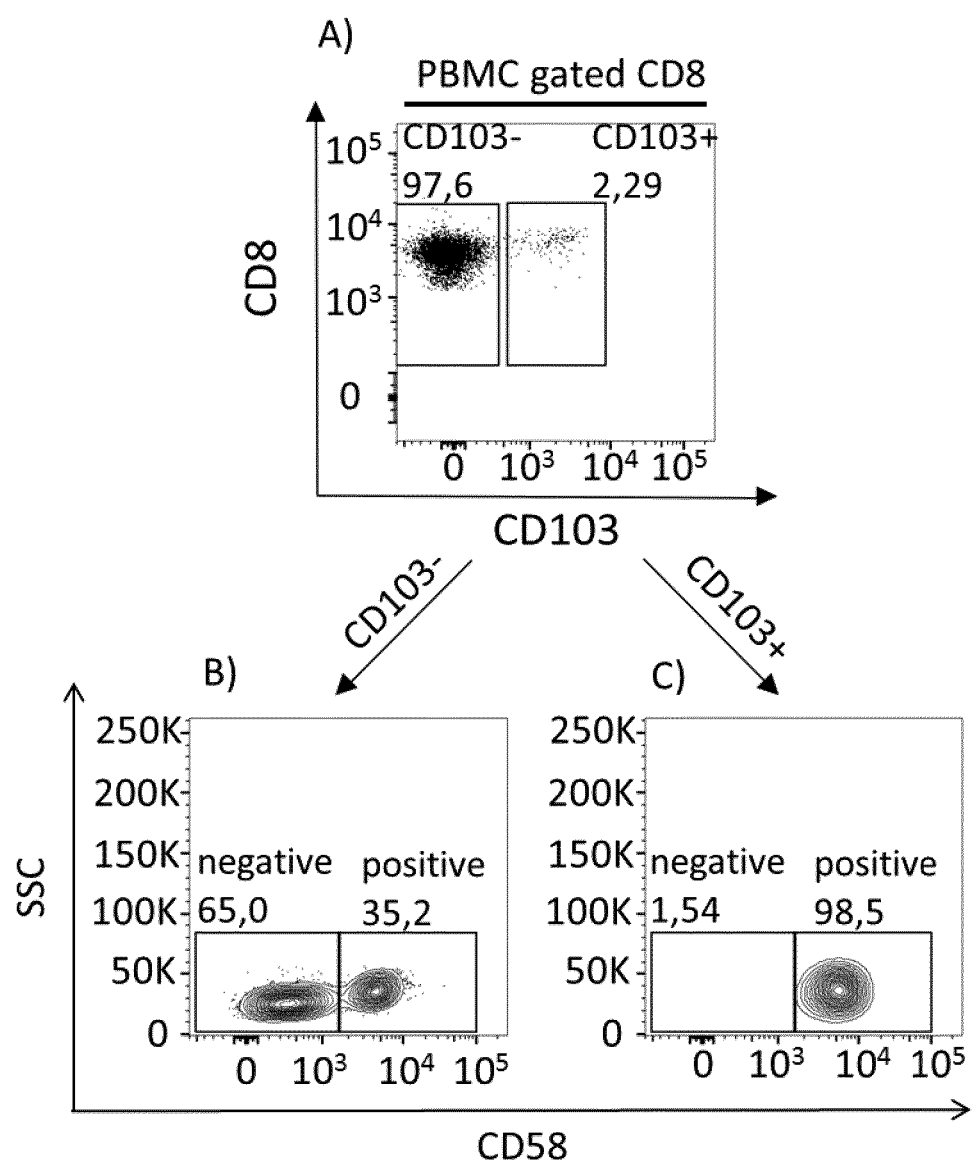

FIG. 17 shows an example of a functional marker, CD58 (LFA-3), which is a putative immunosuppressive element on the surface of T-cells, and which is highly enriched in the CD8⁺CD103⁺ population. It is thus anticipated that CD58 may be used as a marker of preferred condition Y⁺, with which to select for Treg cells within mucosal emigrant, immigrant and activated CD8⁺ T-cell populations. The table presented as FIG. 18 summarises other functional-type markers associated with the CD8⁺CD103⁺ population. The markers positively correlated are of condition Y⁺, and largely represent entities with putative immunosuppressive activities, where in the preferred aspect they are used as a positive selection marker for the purification of Tregs from mucosal emigrant, immigrant and activated CD8⁺ T-cell populations. The markers negatively correlated are of condition Y⁻, and largely represent entities with putative pro-inflammatory activities, where in the preferred aspect they are used as a negative selection marker for the purification of Tregs from mucosal emigrant, immigrant and activated CD8$^+$ T-cell populations. Each marker in this table is also assigned a class, where class 1 represents a strong association with the CD8$^+$CD103$^+$ population and high functional significance. Class 2 represents a strong association with the CD8$^+$CD103$^+$ population or high functional significance. Class 3 represents weak association and/or uncertain functional significance.

Any of these markers, Y, can be included in a CD8$^+$ Treg cell population according to the invention or can be used in a method of the invention to select the right signature pattern on the CD8$^+$ Treg cells. As shown in FIG. 18, class 1 markers include: CD25, CD58, CD73, CD95, CD105, CD107a, CD107b, CD122, CD244, CD268, and CD274. Class 2 markers include: CD31, CD35, CD39, CD41a, CD63, CD85, CD88, CD97, CD108, CD120b, CD127, CD130, CD132, CD151, CD210, CD221, CD226, CD335, CD336, and EGF-R. Class 3 markers include: CD66, CD126, CD150, CD161, CD195, CD200, and CD279.

The CD8$^+$ Treg cells may thus have specific signatures that
i) identify that the cells are regulatory T-cells, typically CD8$^+$CD122$^+$
ii) identify that the regulatory T-cells are tissue type tropic, i.e. they can migrate to the diseased area (i.e. small bowel mucosa), typically α4β7$^+$ or α4$^+$β7$^+$
iii) optionally, identify that the Treg cells are diseased tissue tropic, i.e. they are so-called homing cells that can localize in the diseased tissue, typically CCR9$^+$,
iv) identify that the regulatory T-cells are emigrant cells, i.e. they originate from the target tissue, i.e. the diseased tissue (antigen-experienced cells), typically CD62L$^-$, and
v) optionally identifying that the Treg cells are capable of being retained in the target tissue,
and optionally one or more X-signatures selected from
a) CD49d, CD54, CD99, CD99R, CD166,
b) CD49a, CD49c, CD49f, CD102, CD165, CDw328, CDw329, and/or
c) CD37, CD38, and CD49e,
and optionally one or more Y-signatures selected from
d) CD25, CD58, CD73, CD95, CD105, CD107a, CD107b, CD122, CD244, CD268, CD274,
e) CD31, CD35, CD39, CD41a, CD63, CD85, CD88, CD97, CD108, CD120b, CD127, CD130, CD132, CD151, CD210, CD221, CD226, CD335, CD336, EGF-R, and/or
f) CD66, CD126, CD150, CD161, CD195, CD200, CD279.

Any single Y-signature may be incorporated into the Treg identifier of aspect i) above, or multiple Y-signatures may be incorporated as such. Optionally, further Y-signature marker or markers, may be added to identified Treg subtypes within the target population.

Moreover, it is preferred that the cos+ Treg cells are not recent thymic emigrants or are immigrant cells to the lymph nodes from the peripheral circulation. Therefore, the CD8$^+$ Treg cells may exclude one or more of the following signatures:
h) CD62L$^+$—i.e. to exclude cells that gain access to lymph nodes via HEV (high endothelial venules),
j) CCR9$^+$CD45RA$^+$, CCR9$^+$CCR7$^+$, CCR9$^+$CD62L$^+$, and/or CCR9$^+$CD45RO$^-$ to exclude cells that are recent thymic emigrants, e.g. cells that are CCR9$^+$CD45RA$^+$ or CCR9$^+$CCR7$^+$or CCR9$^+$CD62L$^+$. Any combination of these markers for the denoted+/condition is considered relevant to the exclusion of recent thymic emigrant de novo T-cells, and for the parallel exclusion of resting central memory cells that have not been recently activated against antigen (i.e. should carry the CD45RA$^+$/CD45RO$^-$ character),
k) CCR9$^+$CCR7$^+$CD62L$^+$CD45RA$^+$CD45RO$^-$ to exclude all h) and j) above.

In the following table are given examples of possible combinations of signatures that are within the scope of the present invention. This table does not exclude any possible combination of signatures that can be derived from the specification and appended claims.

| | CD8$^+$α4β7$^+$ CD62L$^-$ | CD8$^+$ α4$^+$ β7$^+$ CD62L$^-$ | CD8$^+$ α4 β7$^+$ CD62L$^-$ CCR9$^+$ | CD8$^+$ α4$^+$ β7$^+$ CD62L$^-$ CCR9$^+$ | CD8$^+$ α4 β7$^{hi}$ αE$^+$ CD62L$^-$ | CD8$^+$ α4$^+$ β7$^{hi}$ αE$^+$ CD62L$^-$ | CD8$^+$ CD62L$^-$ α4 β7$^{high}$ αE$^+$ CCR9$^+$ | CD8$^+$ CD62L$^-$ α4$^+$ β7$^{high}$ αE$^+$ CCR9$^+$ |
|---|---|---|---|---|---|---|---|---|
| x | | | | | | | | |
| CD49d, CD54, CD99, CD99R, CD166, | x | x | x | x | x | x | x | x |
| CD49a, CD49c, CD49f, CD102, CD165, CDw328, CDw329 | x | x | x | x | x | x | x | x |
| CD37, CD38, CD49e | x | x | x | x | x | x | x | x |
| y | | | | | | | | |
| CD25, CD58, CD73, CD95, CD105, CD107a, CD107b, CD122, CD244, CD268, CD274 | x | x | x | x | x | x | x | x |

-continued

| | CD8+α4β7+ CD62L− | CD8+ α4+ β7+ CD62L− | CD8+ α4 β7+ CD62L− CCR9+ | CD8+ α4+ β7+ CD62L− CCR9+ | CD8+ α4 β7$^{hi}$ αE+ CD62L− | CD8+ α4+ β7$^{hi}$ αE+ CD62L− | CD8+ CD62L− α4 β7$^{high}$ αE+ CCR9+ | CD8+ CD62L− α4+ β7$^{high}$ αE+ CCR9+ |
|---|---|---|---|---|---|---|---|---|
| CD31, CD35, CD39, CD41a, CD63, CD85, CD88, CD97, CD108, CD120b, CD127, CD130, CD132, CD151, CD210, CD221, CD226, CD335, CD336, EGF-R | x | x | x | x | x | x | x | x |
| CD66, CD126, CD150, CD161, CD195, CD200, CD279 | x | x | x | x | x | x | x | x |
| X + y | | | | | | | | |
| CD49d, CD54, CD99, CD99R, CD166, CD25, CD58, CD73, CD95, CD105, CD107a, CD107b, CD122, CD244, CD268, CD274 | x | x | x | x | x | x | x | x |
| CD49a, CD49c, CD49f, CD102, CD165, CDw328, CDw329, CD25, CD58, CD73, CD95, CD105, CD107a, CD107b, CD122, CD244, CD268, CD274 | x | x | x | x | x | x | x | x |
| CD37, CD38, CD49e, CD25, CD58, CD73, CD95, CD105, CD107a, CD107b, CD122, CD244, CD268, CD274 | x | x | x | x | x | x | x | x |
| CD49d, CD54, CD99, CD99R, CD166, CD31, CD35, CD39, CD41a, | x | x | x | x | x | x | x | x |

-continued

| | CD8+α4β7+ CD62L− | CD8+ α4+ β7+ CD62L− | CD8+ α4 β7+ CD62L− CCR9+ | CD8+ α4+ β7+ CD62L− CCR9+ | CD8+ α4 β7hi αE+ CD62L− | CD8+ α4+ β7hi αE+ CD62L− | CD8+ CD62L− α4 β7high αE+ CCR9+ | CD8+ CD62L− α4+ β7high αE+ CCR9+ |
|---|---|---|---|---|---|---|---|---|
| CD63, CD85, CD88, CD97, CD108, CD120b, CD127, CD130, CD132, CD151, CD210, CD221, CD226, CD335, CD336, EGF-R | | | | | | | | |
| CD49a, CD49c, CD49f, CD102, CD165, CDw328, CDw329, CD31, CD35, CD39, CD41a, CD63, CD85, CD88, CD97, CD108, CD120b, CD127, CD130, CD132, CD151, CD210, CD221, CD226, CD335, CD336, EGF-R | x | x | x | x | x | x | x | x |
| CD37, CD38, CD49e, CD31, CD35, CD39, CD41a, CD63, CD85, CD88, CD97, CD108, CD120b, CD127, CD130, CD132, CD151, CD210, CD221, CD226, CD335, CD336, EGF-R | x | x | x | x | x | x | x | x |
| CD49d, CD54, CD99, CD99R, CD166, CD66, CD126, CD150, CD161, CD195, CD200, CD279 | x | x | x | x | x | x | x | x |
| CD49a, CD49c, CD49f, CD102, CD165, CDw328, CDw329, | x | x | x | x | x | x | x | x |

-continued

| | CD8+α4β7+ CD62L− | CD8+ α4+ β7+ CD62L− | CD8+ α4 β7+ CD62L− CCR9+ | CD8+ α4+ β7+ CD62L− CCR9+ | CD8+ α4 β7hi αE+ CD62L− | CD8+ α4+ β7hi αE+ CD62L− | CD8+ CD62L− α4 β7high αE+ CCR9+ | CD8+ CD62L− α4+ β7high αE+ CCR9+ |
|---|---|---|---|---|---|---|---|---|
| CD66, CD126, CD150, CD161, CD195, CD200, CD279 | | | | | | | | |
| CD37, CD38, CD49e, CD66, CD126, CD150, CD161, CD195, CD200, CD279 | x | x | x | x | x | x | x | x |

Terminology of Immunology Cell Marker Identification

Through the use of flow cytometry it is possible not only to detect the presence or absence of a protein on a cell surface, but also accurately quantify how much of a protein is on the cell surface. Some plasma membrane markers are either expressed or not on a particular cell, while others have expression that can be quite graded across various cell types. For example, CD4 is either expressed or not, so cells are annotated simply as CD4− or CD4+, respectively. On the other hand, a graded expression of the CD25 protein is common, so CD25 expression is sometimes noted as $CD25^{lo}$, $CD25^{int}$, $CD25^{hi}$ (or $CD25^{high}$), for low, intermediate or high expression, respectively. It should be noted that measurement of fluorescence intensity in flow cytometric applications is generally visualised in a log scale. In addition, multi-fluorochrome analyses generally require computational compensation of data to correct for spectral overlap of the different fluorochromes. Therefore, depending on the content and style of analysis, marker resolution can be differently represented, even when the same antibody/fluorochrome reagent is used for analysis of the marker in question. In practical terms, this means that the resolution of $X^{hi}$ from $X^{int}$ populations is not always achievable, especially in more complex multivariable analyses. In such instances, it is common to refer to the $X^{+/-}$ annotations, where the $X^+$ condition is inclusive of known $X^{int}$ and $X^{hi}$ populations. Thus $X^+$ may be used in the analytical or physical definition of $X^{hi}$, for example, so long as $X^{int}/X^{hi}$ differentiator is not representative of a critical and otherwise unqualified descriptor of population identity.

Tregs and Treg Subtypes

T-cells or T-lymphocytes belong to a group of white blood cells known as lymphocytes and play a central role in cell-mediated immunity. They can be distinguished from other lymphocyte types, such as B cells, by the presence of a specific receptor on their cell surface, the so-called T-cell receptors (TCR). T-cells represent a massively diverse set of small cells that embody the modulatory workhorse of the immune system.

Several different subsets of T-cells have been discovered, each with a distinct function T helper cells ($T_H$ cells) including effector T-cells (Teff) and regulatory T cells (Treg); memory T-cells ($T_M$ cells), natural killer T-cells (NKT cells) etc.

Effector T-cells are responsible for promoting "pro-inflammatory" responses, while regulatory T-cells are their antithesis in promoting "anti-inflammatory" responses. Thus the outcome of any specific immune response of switching inflammation on and off can be considered as a balance between Teff and Treg activities.

T-cells can express one of either CD4 or CD8 receptors (CD denotes cluster of differentiation). These closely related receptors are components of TCR, and responsible for the specific docking to MHC complexes. MHC is a complex of multiple proteins expressed on the surface of cells, and can be divided into two types. MHC class I (MHC I) is expressed on all cell types, while MHC class II (MHC II) is largely related to dendritic cells (DC) and antigen-presenting cells (APC). These protein complexes are those responsible for presenting antigens to cells of the adaptive immune system, specifically to T-cells. MHC I is responsible for presenting antigens of that are obtained from within the cell ("self" antigens), whereas MHC II is responsible for representing antigens that are obtained from outside the cell ("non-self" antigens). CD4 is responsible for docking to MCH II, while CD8 is responsible for docking to MHC I. Thus, CD4 will recognize antigens derived from outside the cell, whereas CD8 will recognize those from within the cell.

Treg cells are subdivided into "natural Tregs" (nTregs) and "induced Tregs" (iTregs). nTregs arise naturally in the thymus, and are selected on the basis of being able to react with "self" antigens. This means that they are the general mediators of so called "self-tolerance". That is, they stop the immune system from attacking the body's own tissues. On the other hand, iTregs are those cells selected from nave T-cells in peripheral tissues for antigens from both self and extrinsic factors. Therefore, iTregs can be considered to mediate "adaptive tolerance", or tolerance towards mainly nonharmful entities like antigens from our food, commensal bacteria in our intestines, or tissue-specific self-constituents that are not selected against in the thymic selection process. Peripherally induced self-reactive CD8+ iTregs may play a major role in mucosal immune tolerance. This concept of local clonal selection is something that can be referred to as antigen "education", and involves many co-stimuli.

T-Cell Migration

Integrin proteins are proteins that generally form dimeric complexes on the cell surface of two different integrin forms. These dimeric forms represent an adhesive unit that adheres to specific receptors presented on the walls of blood vessels and other structures. This means, cells that express a specific integrin pair can bind to a specific receptor, which itself can be expressed on the blood vessels in a specific tissue. In effect, the expression of specific integrin pairs on a cell can essentially barcode a cell to stick to the blood vessel walls of a specific tissue. The integrin pair responsible for sticking cells to the blood vessels of mucosal tissue is the α4β7-integrin dimer, for example.

However, to transmigrate across the cell wall into a target tissue, the cell needs to also receive a second signal, effectively serving as a further refinement of exactly what part of the selected tissue the cell should access by matching activators produced by specific tissue compartments to cognate receptors expressed by specific cells. In the case of the small bowel mucosa a small protein called CCL25, which is a "chemokine", is produced. This can trigger cells to transmigrate into the small bowel by binding to the CCR9 receptor on migrating cell surfaces. CCL25 binding to the CCR9 receptor induces the active state of the α4β7-integrin dimer, allowing tight binding and endothelial transmigration. In this example a cell must possess both α4β7-integrin and CCR9 on their cell surface to move into the small bowel mucosa.

There exist other distinct types of adhesion molecules and chemoattractants involved in directed cell migration, than the integrin and chemokine examples above.

Therapeutic Use—Immunotherapy

Immunotherapy is broadly used to describe any clinical treatment that aims to modulate immune function. With respect to cellular immunotherapy, the two major fields of cellular immunotherapy focus on cell-based vaccine (mainly DC) immunotherapy and T-cell immunotherapy. In traditional vaccination, antigen preparations are injected directly to the subject to raise immune responses against antigens specific for disease pathogen. DC immunotherapy is thought to be more effective as antigens are pre-loaded onto DC cells, and they can more effectively enhance antigen cross-presentation to T-cells and B-cells in vivo. T-cell immunotherapies can be divided into immunostimulatory and immunosuppressive classes. Adoptive transfer of CD4$^+$ T-effector cells, or cytotoxic CD8 T-cells in the case of cancer, is seen as immunostimulatory in provoking immune responses against tumours. Treg immunotherapies by contrast aim to provide immunosuppressive capacity in treatment of inflammatory and autoimmune conditions.

The markers identified in the case study described herein may be used to define Treg populations that may be harvested from patient blood, purified ex vivo, expanded, re-patterned, if necessary, and then infused back to the patient. The method of autologous Treg adoptive immunotherapy is thus defined at the level of cell identification by the presented markers, as a means of purification by flow cytometric (or affinity) approaches.

The Tregs as identified herein can be used in the treatment of IBD including Crohn's disease and ulcerative colitis as well as other inflammatory diseases of the small and large bowel such as indeterminate colitis, pseudomembranous colitis, microcytic colitis (including lymphocytic colitis and collagenous colitis), bowel symptoms in systemic lupus erythematous (SLE), bowel symptoms in systemic sclerosis, primary (progressive) sclerosing cholangitis and bowel-associate graft-versus-host disease manifestations in organ, tissue and haematological transplantation.

The Tregs as identified herein can be used in the treatment of IBD, i.e. ulcerative colitis and Crohn's disease.

Aspects relating to treatment of Crohn's disease affecting the small bowel are described herein. However, as explained herein before CD may affect the whole gastrointestinal tract and, accordingly, the aspects of the invention may be broadened to treatment of CD affecting other parts of the gastrointestinal tract. Furthermore, inflammatory diseases (also outside the gastrointestinal tract) may be treated with Tregulatory cells using the same approach. As mentioned above the signatures are expected to be of similar nature. Elements of marker signatures relating to small bowel tropism and emigration, which in case e.g. of CD of the colon or perianal area should be changed to colon tropism and anal canal tropism etc, when targeting disease in these areas. That is to say, when treating other inflammatory diseases, the identity of Treg cells may be similar whereas the homing functions will be related to the tissue type and location of inflammation. However, it may be anticipated that functional makers of Tregs of a specific tissue type or anatomical location may be particular to this tissue type or location, in as much that functional makers may serve to further define Treg origin is that of the tissue of interest.

As described above, signatures of a CD8$^+$ Treg cell population suitable for use in cellular immunotherapy of CD are identified and, accordingly, a starting material can be obtained e.g. from the subject suffering from the inflammatory or autoimmune disease of the gastrointestinal tract.

Such starting material can be obtained by the following method comprising i) subjecting peripheral blood from a patient suffering from an inflammatory or an autoimmune disease of the gastrointestinal tract to single-cell analysis, to obtain CD8$^+$ Treg cells having the selection of signatures described herein.

The method includes means to sort CD8$^+$ Treg cells that are emigrant/immigrant populations from/to the diseased tissue and that they can localise in the diseased tissue.

The CD8$^+$ Treg cells may also contain the signatures CD38$^+$, CD69$^+$ and/or CD44$^+$ to denote recent activation.

The method typically apply analytical filters to i) exclude cells that gain access to lymph nodes via HEV, and ii) exclude cells that are recent thymic emigrants.

The cells that gain access to lymph nodes via HEV may be CD62L+ cells; and recent thymic emigrants may be CCR9$^+$CD45RA$^+$, CCR9$^+$CCR7$^+$, CCR9$^+$CD62L$^+$, or CCR9$^+$CD45RO$^-$ cells.

Thus, in the CD8$^+$ Treg cells to be excluded are CCR9$^+$CCR7$^+$CD62L$^+$CD45RA$^+$CD45RO$^-$ cells.

The invention also relates to a method for obtaining Treg cells as defined herein, the method comprising essentially the steps described above, but Treg cells are provided lacking one or more signatures, notably X, Y, α4β7$^+$ or α4$^+$β7$^+$CCR9$^+$ or α4$^+$β7$^+$, where X is the signature indicating that the Tregs can localize, has emigrated from, or is marked for preferential retention in the specific part of the gastrointestinal tract that is diseased. X may be X$^+$ or X may be X. Y is a functional marker and Y may be Y$^-$ or Y$^+$.

The signature(s) may be introduced or re-introduced to the Treg cell by stimulation of cells with a combination of ATRA, TGFbeta and IL10. In the case that the repatterning relates to the signature α4$^+$β7$^+$X, the repatterning stimulation is the same as mentioned above, but includes additional rapamycin supplementation.

Thus, Treg cells may be provided as described herein before.

Irrespective of the gastrointestinal location of the inflammation, any of the signatures may also comprise CD38$^+$.

The Treg cells obtained may then be expanded (cultured) and, optionally re-patterned as described herein. The thus obtained/expanded/re-patterned CD8$^+$ Treg cells may then be administered to the patient suffering from the inflammatory or autoimmune disease of the gastrointestinal tract.

In a separate aspect, the invention relates to a composition for cellular immunotherapy, the composition comprising a CD8$^+$ Treg cell population identified and/or obtainable as described herein.

Treg cells may be dispersed in a suitable medium before administration to the patient. A suitable medium may be an aqueous medium e.g. containing substances that ensures viability of the cells. It may also contain osmotically active substances, pH regulating substances or other physiologically acceptable substances. To this end, the present invention also relates to a pharmaceutical composition comprising the Treg cells specified herein together with an aqueous medium. The pH and osmotic pressure of the composition are adjusted to physiologically acceptable values, i.e. pH in a range of from 3 to 8 including 7.4, and the osmotic pressure in a range of from 250 350 mOsm/l including 285-300 mOsm/l. A specific example of a suitable medium is a 0.9% w/w sodium chloride solution comprising up to 3% w/w human serum albumin such as up to 2% w/w serum albumin or up to 1% w/w serum albumin. Another suitable medium is an aqueous medium comprising albumin such as 2% w/w albumin. They may also be suspended in saline-based solutions of physiological pH, and with appropriate biological and non-biological additive to promote cell survival and stability.

The Treg cells may also be admixed with a blood sample preferably from the patient's own blood or at least from blood compatible with the patient's own blood.

The Treg cells are normally administered parenterally to the patient such as intraveneous, intraarterial, intrathecal or intraperitoneal administration.

The number of cells to be administered depends on the disease and the severity of the disease to be treated, as well as the weight and age of the patient. It is contemplated that the number of cells is in a range of from $1\times10^5$ to about $10\times10^9$.

The Treg cells are administered by the parenteral route, preferably via injection into the circulatory system.

Aspects relating to treatment of Crohn's disease affecting the small bowel are described herein. However, as explained herein before CD may affect the whole gastrointestinal tract and, accordingly, the aspects of the invention may be broadened to treatment of CD affecting other parts of the gastrointestinal tract. As mentioned above the signatures are expected to be essentially the same apart from the signature relating to small bowel tropism, which in case e.g. of CD of the colon or anal canal and perianal area should be changed to colon or anal canal tropism etc.

The invention also relates to a method for treating a patient suffering from an inflammatory disease of the gastrointestinal tract, the method comprises
a) isolating Treg cells defined herein from a tissue sample obtained from a patient suffering from an inflammatory disease in the gastrointestinal tract,
b) expanding the Treg cells in vitro,
c) optionally re-patterning the expanded Treg cells to obtain Tregs that have signatures
ii) and iv) and optionally iii) and/or v); or the T-cells have the signatures ii), iv) and v) and optionally iii), or the T-cells have the signatures ii), iv) and v) and optionally iii). wherein the signatures is for
    ii) identifying that the Treg cells are tissue type tropic, i.e. they can migrate to mucosal tissue,
    iii) optionally, identifying that the Treg cells are diseased tissue tropic, i.e. homing cells that can localize in the diseased tissue region,
    iv) identifying that the Treg cells are emigrant cells, i.e. they originate from the target tissue, and
    v) optionally, identifying that the Treg cells are retained in the target tissue,
d) administering the Treg cells obtained from b) or c) to the patient.

In a specific aspect, the invention relates to a method for treating a patient suffering from Crohn's disease affecting small bowel, the method comprises
a) obtaining Treg cells defined herein from a tissue sample obtained from a patient suffering from an inflammatory disease in the gastrointestinal tract, for example the small bowel such as, e.g., Crohn's disease,
b) expanding the Treg cells in vitro,
c) optionally re-patterning the expanded Treg cells to obtain Tregs that have have signatures for
    ii) identifying that the Treg cells are tissue type, in this case mucosal tropic, i.e. they can migrate to mucosal tissue,
    iii) optionally, identifying that the Treg cells are diseased tissue tropic, i.e. homing cells that can localize in the diseased tissue of the small bowel,
    iv) identifying that the Treg cells are emigrant cells, i.e. they originate from the target tissue of the gastrointestinal tract, and
    v) optionally, identifying that the Treg cells are retained in the target tissue of the gastrointestinal tract,
d) administering the Treg cells obtained from b) or c) to the patient.

The expanded and optionally repatterned Treg cells from step b) or c) should have features as defined herein.

As explained herein before the method of the invention is not limited to treatment of a patient suffering from Crohn's disease in the small bowel or suffering from an inflammation of the small bowel, but the method is also applicable to treatment of a patient suffering from Crohn's disease in other parts of the gastrointestinal tract. In such case the above-mentioned method must be adjusted in such a manner that Tregs are obtained that are suitable for use in the treatment of Crohn's disease in the diseased part of the gastrointestinal tract, see e.g. under the description of Tregs.

The Tregs are suitably obtained from a tissue sample from a patient. The sample may be from a lymph node such as a mesenteric lymph node draining inflamed bowel, or it may be from bowel mucosa, from lamina propria or it may be from a blood sample. Most conveniently, the sample is a peripheral blood sample.

The present invention also relates to a method for obtaining Treg cells as defined herein, the method comprises
a) obtaining Treg cells defined herein from a tissue sample obtained from a patient suffering from an inflammatory disease in the small bowel,
b) expanding the Treg cells in vitro,
c) optionally re-patterning the expanded Treg cells to obtain Tregs that have signatures ii) and iv) and optionally iii) and/or v); or the T-cells have the signatures ii), iv) and v) and optionally iii), or the T-cells have the signatures ii), iv) and v) and optionally iii), wherein the signatures is for
    ii) identifying that the Treg cells are tissue type tropic, i.e. they can migrate to mucosal tissue, iii) optionally, identifying that the Treg cells are diseased tissue tropic, i.e. homing cells that can localize in the diseased tissue region, iv) identifying that the Treg cells are emigrant cells, i.e. they originate from the target tissue, and v) optionally, identifying that the Treg cells are retained in the target tissue.

The expanded and optionally repatterned Treg cells from step b) or c) should have features as defined herein.

Sorting of T-Cells

The isolation of cells as referred to in step a) refers to first the recovery of mononuclear cells from patient tissue specimens, and labelling said pool of mononuclear cells with antibodies specific for appropriate markers. The cells can be retrieved from mucosa through microdissection of lamina propria and preparation of the tissue e.g. using enzyme collagenase and other substances and/or mechanical disaggregation. The cells may also be prepared from lymph nodes starting with microdissective trimming of the tissue followed by careful mechanical degradation before using collagenase and substances mentioned above. The cells may also be prepared from peripheral blood.

Typically, the desired $CD8^+$ Treg cells are sorted from the peripheral blood using antibodies against the desired signatures.

Accordingly, in an aspect of the invention, the invention relates to a kit of antibodies, wherein the kit contains antibodies against i) $CD8^+$, and/or $CD122^+$, ii) $\alpha4$, $\alpha4^+$ and/or $\beta7^+$ iii) optionally, $CCR9^+$ iv) $CD62L^-$ v) optionally, $\alpha4^+\alpha E^+\beta7^{hi}$ Furthermore, the kit may contain one or more antibodies against one or more X signatures such as X signatures selected from a) CD49d, CD54, CD99, CD99R, CD166, b) CD49a, CD49c, CD49f, CD102, CD165, CDw328, CDw329, and/or c) CD37, CD38, and CD49e.

The kit may contain one or more antibodies against a functional character such as one or more Y signatures selected from d) CD25, CD58, CD73, CD95, CD105, CD107a, CD107b, CD122, CD244, CD268, CD274, e) CD31, CD35, CD39, CD41a, CD63, CD85, CD88, CD97, CD108, CD120b, CD127, CD130, CD132, CD151, CD210, CD221, CD226, CD335, CD336, EGF-R, and/or f) CD66, CD126, CD150, CD161, CD195, CD200, CD279.

The kit may also contain antibodies against CD38, CD69, CD44, CD45, CCR7, or CD45RO.

Once labelled, cells are purified by immunoaffinity and/or flow cytometric sorting techniques to yield highly enriched or purified Treg populations of desired characteristics. In vitro expansion of isolated Treg populations as referred to in step b) is achieved by way of recombinant T-cell stimulation in the form of anti-CD3/anti-CD28 activating antibodies in combination with IL2, or alternatively the outgrowth of Treg populations on transgenic feeder cell populations, artificial antigen presenting cells or autologous/allogeneic peripheral monocytes or monocyte-derived antigen presenting cells, in addition to IL2 supplementation and/or cytokines and growth factors well known to promote specific T-cell growth and survival. Repatterning of the correct homing receptor expression post-expansion as referred to in c) entails the recombinant reactivation of expanded T-cell populations with anti-CD3/anti-CD28 activating antibodies and subsequent introduction of stimuli in precise combination Stimuli include all-trans retinoic acid, Interleukin-10 and transforming growth factor-beta.

In the case where the Treg cells lack the signature $\alpha4^+\beta7^+CCR9^+$, the signature may be introduced or re-introduced to the Treg cell by stimulation of cells with a combination of ATRA, TGFbeta and IL10. In the case that the repatterning relates to the signature $\alpha4^+\beta7^+X/Y/Z$, the repatterning stimulation is the same as mentioned above, but includes additional rapamycin supplementation.

In case, the Treg cells lack the signature $\alpha4^+\beta7^+$, which can be introduced or reintroduced to the Treg cell by stimulation of cells with a combination of ATRA, TGFbeta and IL10.

Identification, Purification and Expansion of Tregs

The Tregs are identified and purified as described herein. Thus, the identification and purification typically involve the use of specific antibodies and techniques well known to a person skilled in the art.

One set of methods central to manipulating cells from the human body are those that identify a given cell type, and allow their purification as viable cells. In the following is described the key principals of cell identification and purification by direct and indirect means. There are many additional parameters by which cells can be identified, but are destructive in nature, so bare no use in purification and cloning of living cells.

Direct Antibody Detection of Plasma Membrane Markers by Flow Cytometry

The most important method in cellular immunology is the specific detection of surface proteins by way of specific antibodies. Considering cells of different types inevitably express different proteins on their cells surface, identifying specific protein signatures on their surface is the simplest direct means of identifying a given cell type. For instance, CD4 and CD8 form the basis of identifying T-cells in most applications.

Antibodies can be created in controlled conditions against specific proteins, or peptide fragments of proteins. This is simply achieved by injecting a laboratory animal, usually a mouse or rabbit, with a quantity of protein or peptide antigen. In biochemical applications it is often sufficient to use a preparation of the animal's blood to recover large amounts of antibodies, and are termed polyclonal antibodies, since multiple different antibody clones populate these preparations. In contrast, monoclonal antibody production utilizes cloning and characterisation of B-cells from the antigen-challenged animals. The basis for cellular and molecular cloning of antibodies will be discussed further in later sections, but for now we can see that specific single antibodies can be generated for any protein.

It is simply not enough to bind specific antibodies to a cell surface; there must also be a means of detecting each individual antibody. This is most commonly achieved by labelling each antibody with a specific fluorescent dye. Fluorescence simply describes the spectral properties of a molecule that can be excited with light of a specific colour, and will then emit light of a different colour. By labelling each antibody with a different colour, many different antibodies can be used to bind specific proteins on a cell surface, and each be quantitatively detected by the amount of fluorescent signal of each colour emitted by the cell when appropriately excited.

Excitation of different fluorescent dyes in the platforms that we will discuss is achieved by means of different coloured lasers. That is to say lasers emitting light of differing wavelengths. The instrument that often is used to detect multi-parameter fluorescence of cells is called a "flow cytometer". These instruments take cells suspended in solution and flow them, one-by-one, past an array of lasers and photodetectors. We are thus able to measure extremely accurately and rapidly the expression of specific proteins on the surface of individual cells. This technique forms the basis of the vast majority of cellular immunology analysis in both experimental and clinical settings.

Direct Cell Purification by FACS

The use of flow cytometry to purify cells is called fluorescence-activated cell sorting (FACS). FACS instruments represent the same basic principle as analytical flow cytometers, though after the detection of cell fluorescence are able to physically sort cells. FACS instruments can sort cells in two basic manners. First, cells can be identified and sorted into up to four separate pools of cells. Second, single cells can be identified and deposited into single tubes. The single cell deposition is a powerful means of cell identity-based cloning, where individual cells represent clones that may be propagated, characterised and manipulated. A traditional method of single cell cloning is by 'limiting dilution'. This means you have a starting pool of cells, and you dilute these cells so there is on average less than one cell per given volume. The volume of cell suspension is then aliquoted such that you achieve single-cell distribution.

Direct Cell Purification by MACS

Magnetic-activated cells sorting (MACS) technology is another method that can be used. The premise is basically that instead of a fluorescent label, specific antibodies are linked to magnetised microbeads. This in effect means that one is able to effectively magnetise specific cells based antibody binding. The largest drawback of this approach is the obvious limitation to the number of antibodies one can use, since a single antibody bound to a cell surface will magnetise the cell. It is most common to purify cells by a process of negative selection, that is, to magnetise all of the cells that you do not want to purify, and deplete these from your sample. The sophistication of the cell identities that can be purified is relatively low compared to FACS, and inevitably of much lower purity.

Treg Receptor Re-Patterning

It has been observed that the Tregs after manipulation may be devoid of one or more of the signatures. Especially, it has been observed that the MACS-enriched Treg cultures after expansion were almost devoid of small-bowel tropic homing receptor. Therefore, we developed a method to establish the signatures of the Tregs after having been expanded. The method involves a combination of low dose all-trans retinoic acid, TGF and ID 0 to reintroduce the signatures $\alpha 4^+\beta 7^+CCR9^+$, for example.

LEGENDS TO FIGURES

FIG. 1. $CD8^+\alpha 4^+\beta 7^{high}$ T-cells in the peripheral blood are enriched for CD103 and CCR9 expression. PBMC recovered from healthy donor blood over ficoll were immediately labelled with indicated antibodies and analysed by flow cytometry. A) Total CD8 lymphocytes expressed as beta7– vs alpha4– integrin dot plots. Each gate defining alpha4+beta7++, alpha4+beta7+, alpha4-beta7- and alpha4+beta7– are redisplayed as CD103 vs CCR9 contour plots in B), C), D) and E), respectively.

Figure 2:
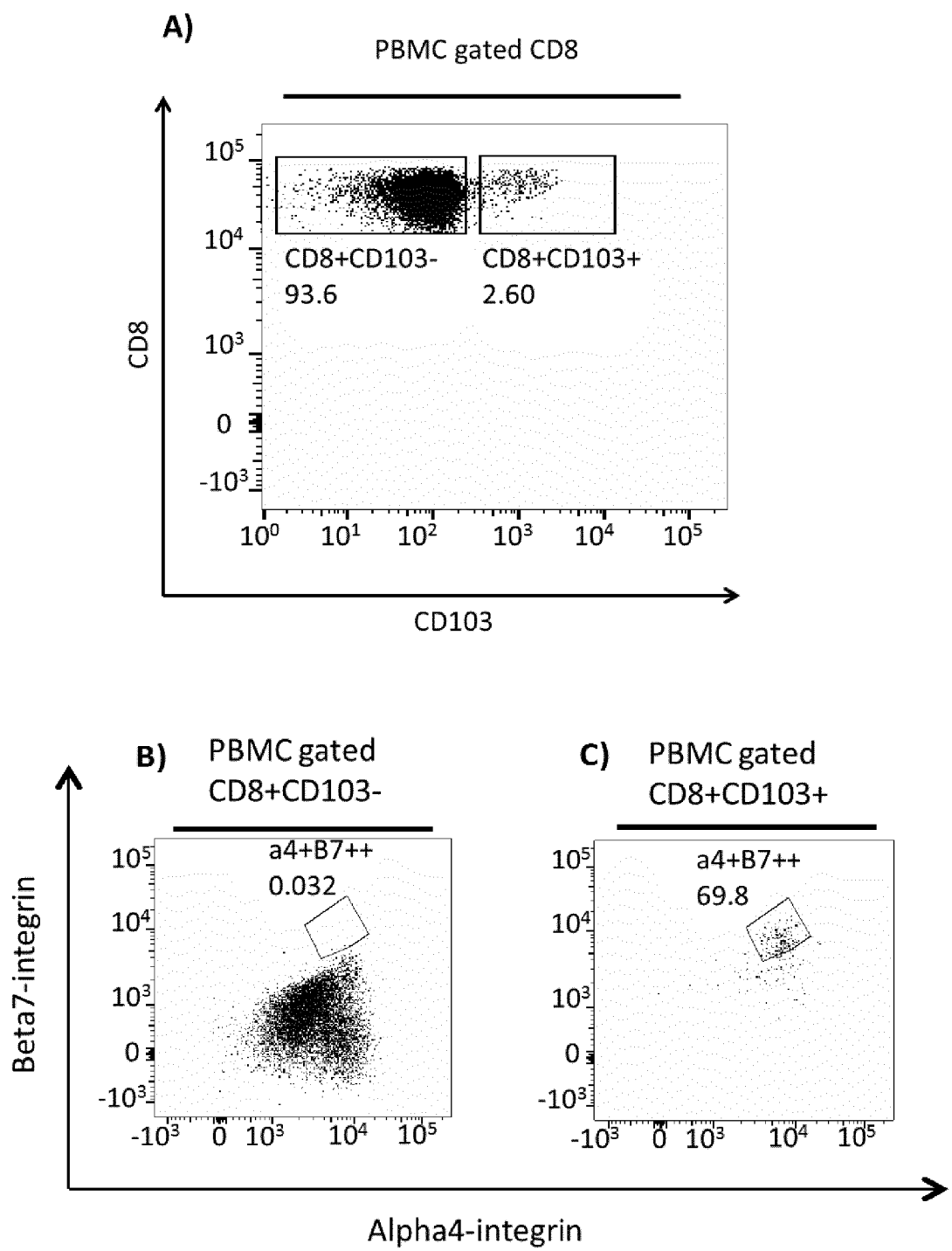

FIG. 2. $CD8^+CD103^+$ T-cells in peripheral circulation are highly enriched for $\alpha 4^+\beta 7^{high}$ expressing T-cells. PBMC recovered from healthy donor blood over ficoll were immediately labelled with indicated antibodies and analysed by flow cytometry. A) Total CD8 lymphocytes expressed as CD8 vs CD103 dot plots. Each gate defining CD8+CD103- and CD8+CD103+ are redisplayed as beta7– vs alpha4– integrin dotplots in B) and C), respectively.

Figure 3:
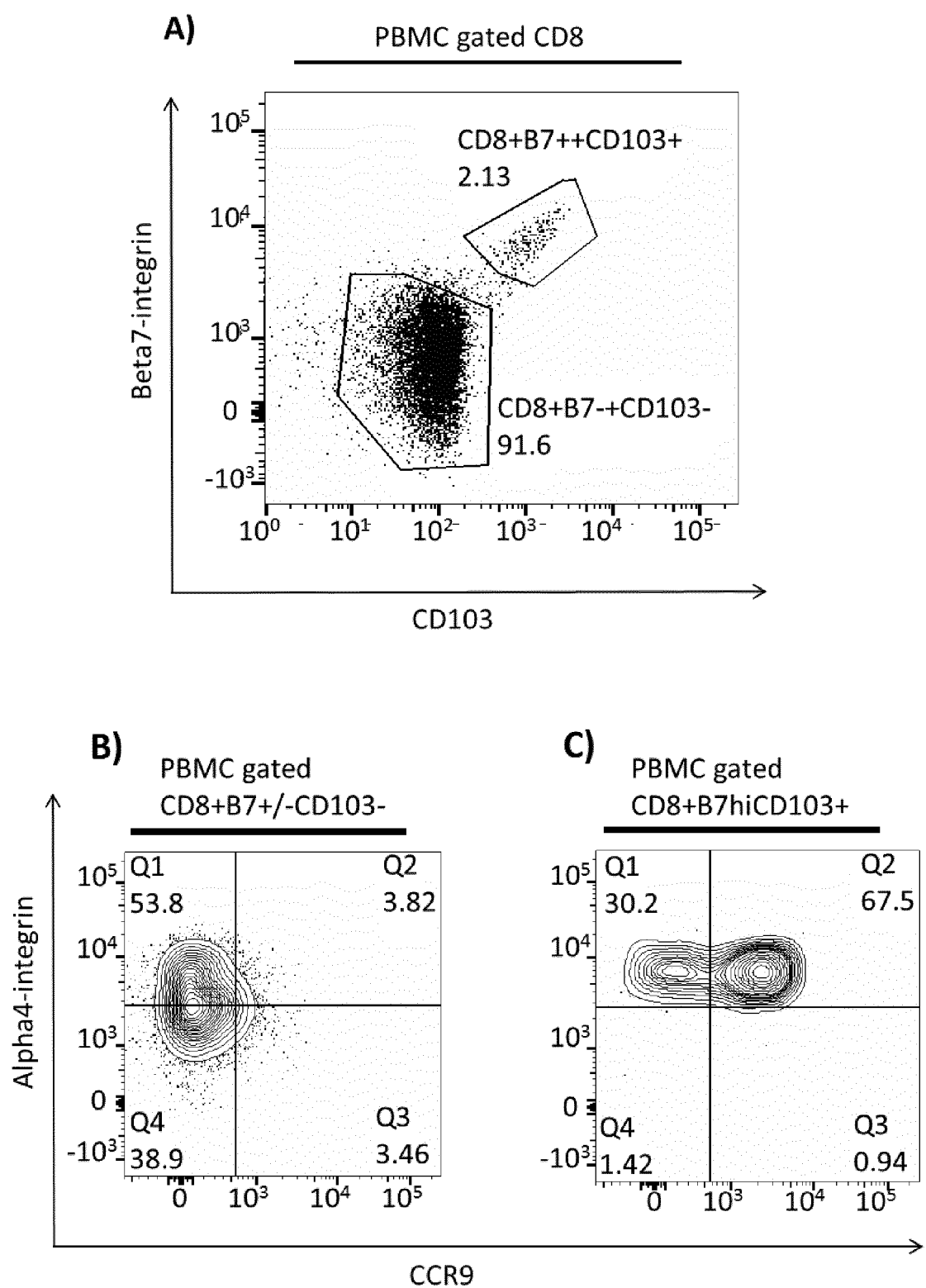

FIG. 3. $CD8^+\beta 7^{high}CD103^+$ T-cells in peripheral circulation are enriched for $\alpha 4^+CCR9^+$ expressing T-cells. PBMC recovered from healthy donor blood over ficoll were immediately labelled with indicated antibodies and analysed by flow cytometry. A) Total CD8 lymphocytes expressed as beta7– integrin vs CD103 dot plots. Each gate defining beta7+CD103– and beta7+CD103+ are redisplayed as alpha4– integrin vs CCR9 contour plots in B) and C), respectively.

FIG. 4. Distinct subsets of $CD8^+\beta 7^{high}CD103^+$ and $CD8^+\beta 7^+CD103^+$ T-cells in peripheral circulation do not express cytotoxic markers. PBMC recovered from healthy donor blood over ficoll were immediately labelled with indicated antibodies and analysed by flow cytometry. A) Total CD8 lymphocytes expressed as beta7-integrin vs CD103 pseudo-colour plot or B) perforin vs Granzyme B dotplots. C) to F) display Perforin vs Granzyme B dotplots of gated populations from from A) as indicated.

FIG. 5. $CD8^+\beta 7^{high}CD103^+$ T-cells but not $CD8^+\beta 7^+CD103^+$ T-cells in peripheral circulation are highly enriched for CCR9 expression but neither express cytotoxic markers. PBMC recovered from healthy donor blood over ficoll were immediately labelled with indicated antibodies and analysed by flow cytometry. A) Total CD8 lymphocytes expressed as beta7-integrin vs CD103 pseudocolour plot or B) CCR9 vs Granzyme B dotplots. C) to F) display CCR9 vs Granzyme B dotplots of gated populations from from A) as indicated.

Figure 6:
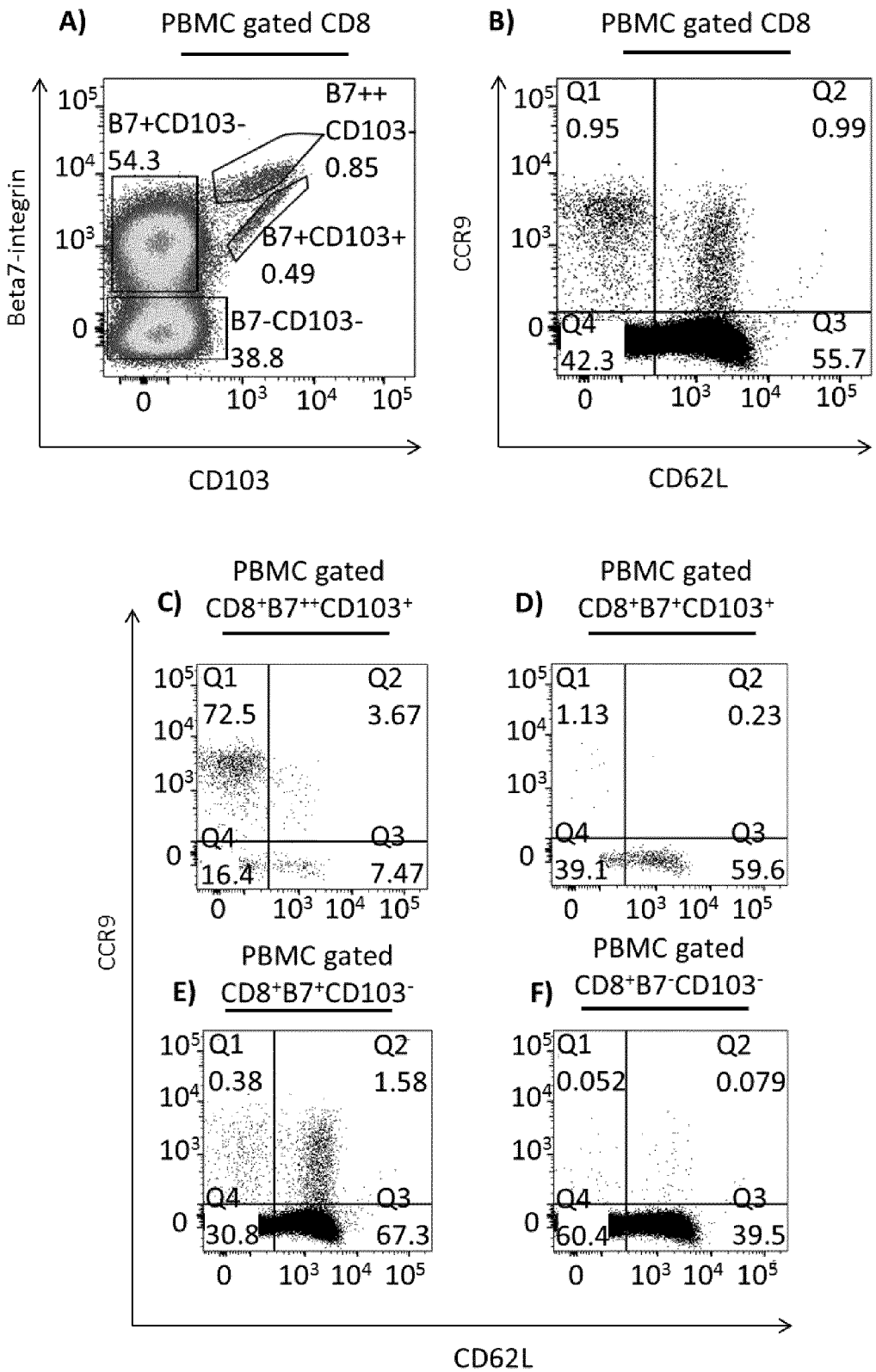

FIG. 6. $CD8^+\beta 7^{high}CD103^+CCR9^+$ T-cells do not express CD62L but $CD8^+\beta 7^+CD103^-CCR9^+$ T-cells are enriched for CD62L expression. PBMC recovered from healthy donor blood over ficoll were immediately labelled with indicated antibodies and analysed by flow cytometry. A) Total CD8 lymphocytes expressed as beta7-integrin vs CD103 pseudocolour plot or B) CCR9 vs CD62L dotplots. C) to F) display CCR9 vs CD62L dotplots of gated populations from from A) as indicated.

Figure 7:
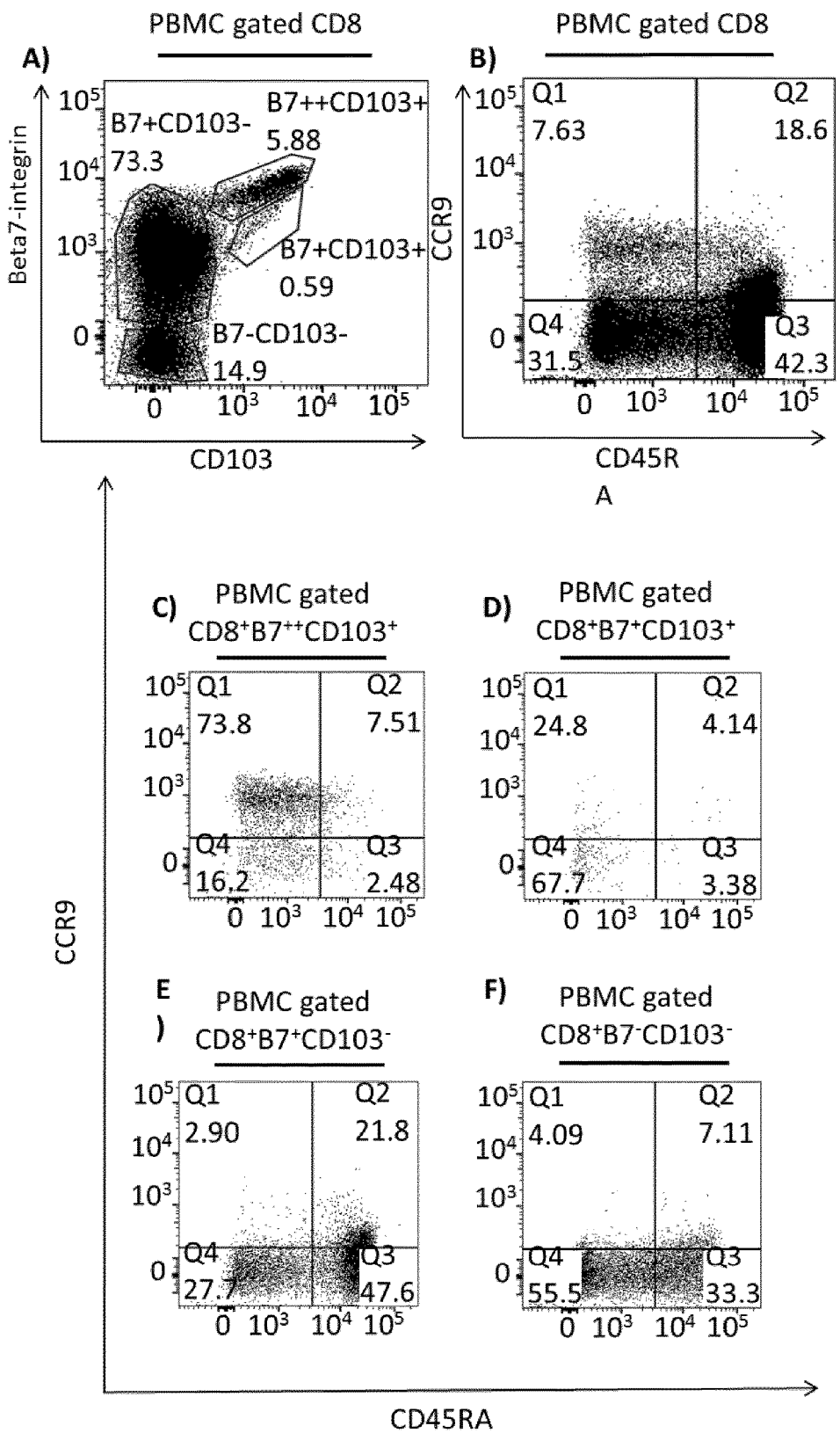

FIG. 7. $CD8^+\beta 7^{high}CD103^+CCR9^+$ T-cells do not express CD45RA but $CD8^+\beta 7^+CD103^-CCR9^+$ T-cells are enriched for CD45RA expression. PBMC recovered from healthy donor blood over ficoll were immediately labelled with indicated antibodies and analysed by flow cytometry. A) Total CD8 lymphocytes expressed as beta7-integrin vs CD103 pseudocolour plot or B) CCR9 vs CD45RA dotplots. C) to F) display CCR9 vs CD45RA dotplots of gated populations from from A) as indicated.

Figure 8:
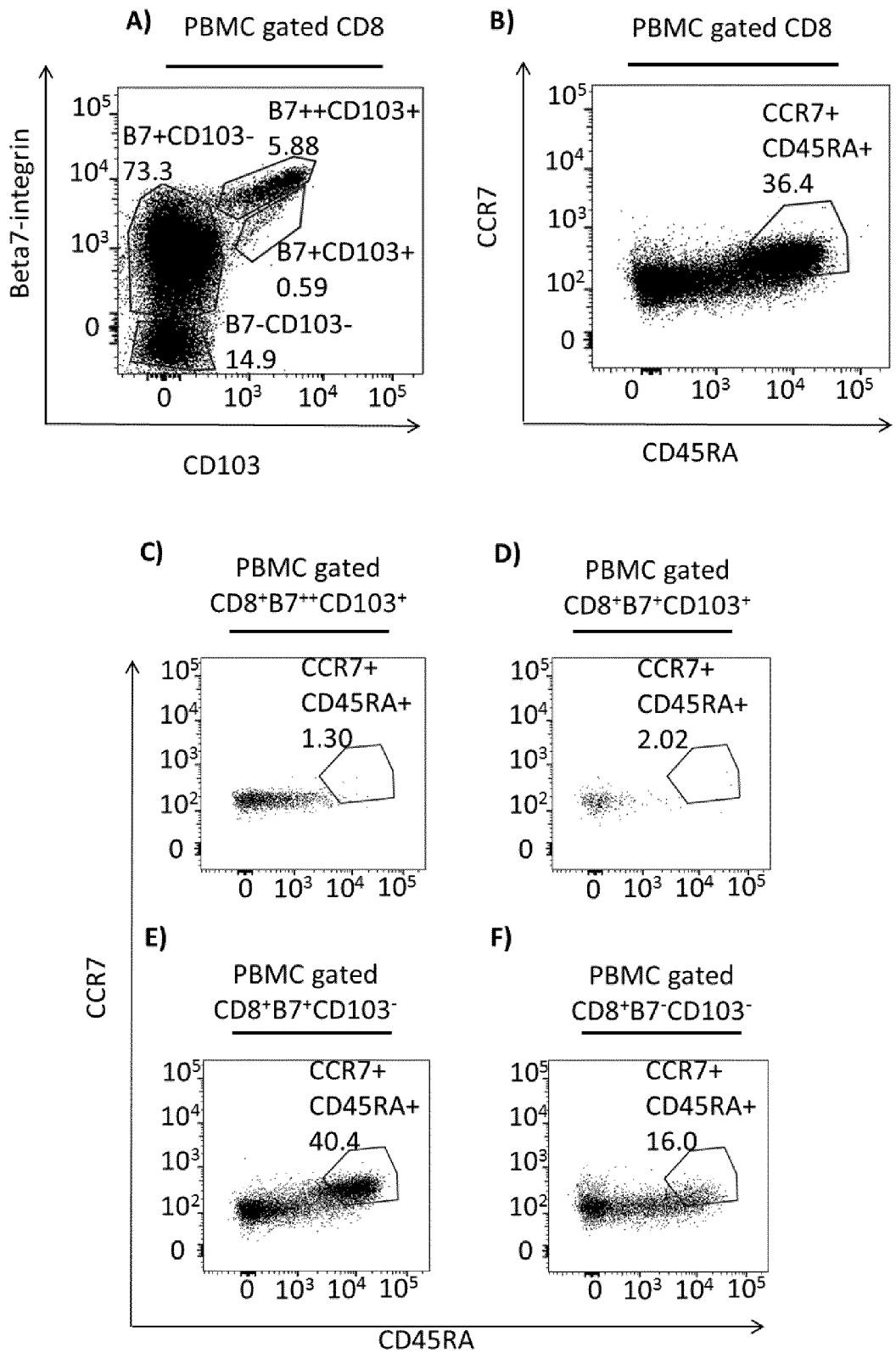

FIG. 8. $CD8^+\beta 7^{high}CD103^+$ and $CD8^+\beta 7^+CD103^+$ T-cells do not contain CD45RA/CCR7 double positives but $CD8^+\beta 7^+CD103^-$ T-cells are enriched for CD45R/CCR7 double positive nave population. PBMC recovered from healthy donor blood over ficoll were immediately labelled with indicated antibodies and analysed by flow cytometry. A) Total CD8 lymphocytes expressed as beta7-integrin vs CD103 pseudocolour plot or B) CCR7 vs CD45RA dotplots. C) to F) display CCR7 vs CD45RA dotplots of gated populations from from A) as indicated.

Figure 9:
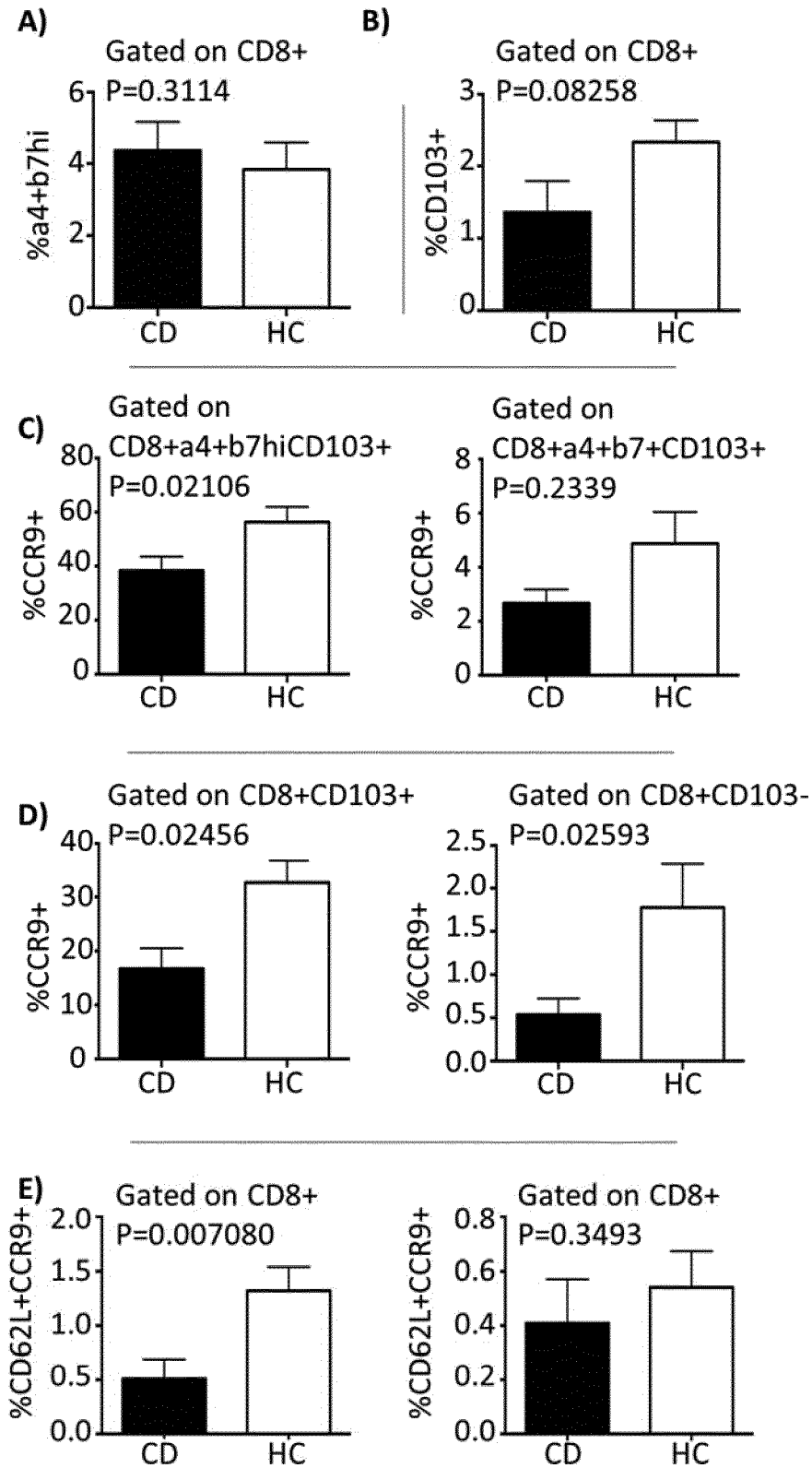

FIG. 9. Reduced relative numbers of peripheral CD8+CCR9+ T-cell populations in CD patients when compared to healthy controls. PBMCs prepared from healthy controls (HC) and CD patients were stained for CD8, CD103, β7, α4 CD62L and CCR9 then analysed by flow cytometry. A) Observed percentage of $\alpha 4^+\beta 7^{hi}$ cells among all $CD8^+$ lymphocytes. B) Observed percentage of $CD103^+$ cells among all $CD8^+$ lymphocytes. C) Observed percentage of $CCR9^+$ cells among $CD8^+\alpha 4^+\beta 7^{hi}CD103^+$ lymphocytes (left panel) and CD8$^+\alpha$4$^+\beta$7$^+$CD103$^+$ lymphocytes (right panel). D) Observed percentage of CCR9$^+$ cells among CD8$^+$CD103$^+$ lymphocytes (left panel) and CD8$^+$CD103$^-$ lymphocytes (right panel). E) Observed percentage of CD8$^+$CD62L$^-$CCR9$^+$ cells among all CD8$^+$ lymphocytes (left panel) and CD8$^+$CD62L$^+$CCR9$^+$ cells among all CD8$^+$ lymphocytes (right panel).

Figure 10:
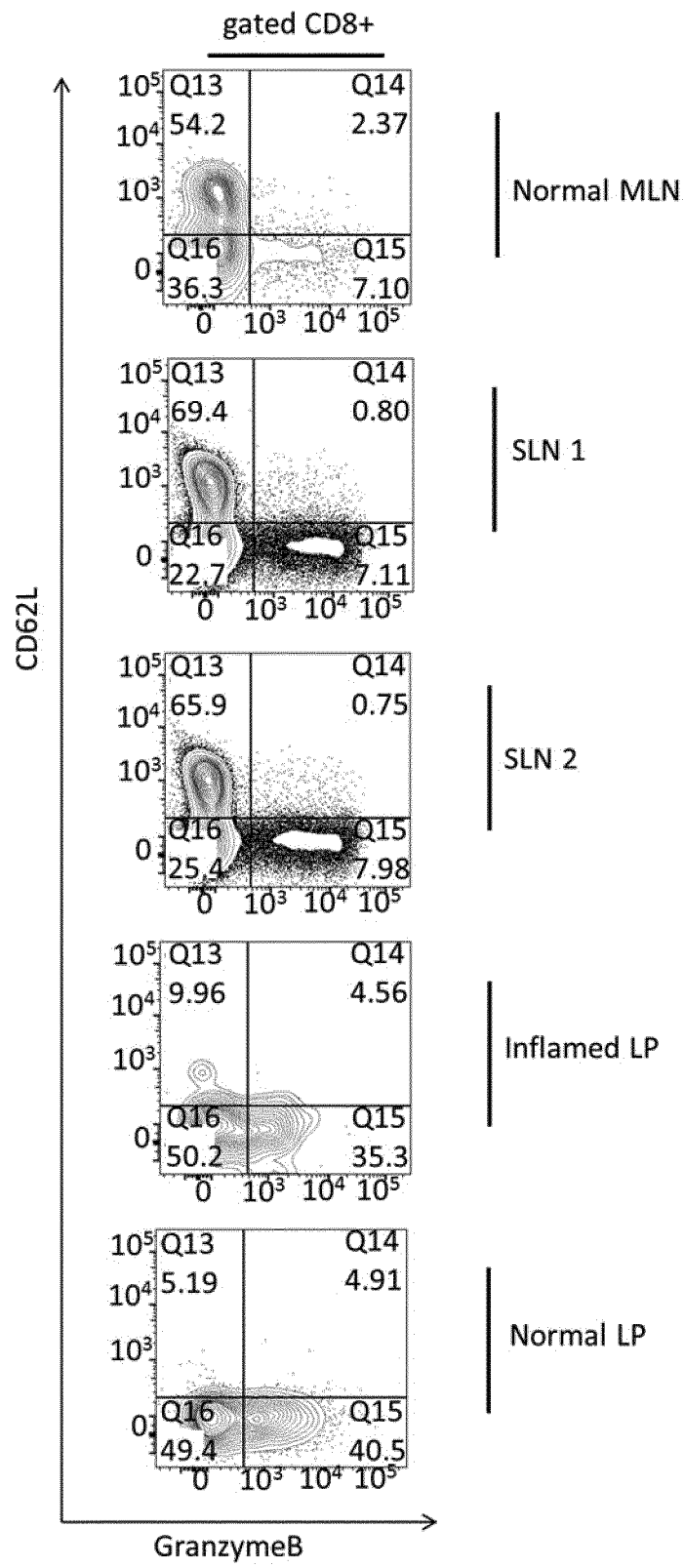

FIG. 10. CD8$^+$ GranzymeB$^+$ T-cells are largely local CD62L$^-$ character in intestinal tissues and do not change in relative abundance in inflamed tissues of CD patients. Single cell suspensions prepared from indicated resected tissues of a representative CD patient with ileocaecal disease and were immediately stained with the indicated antibodies. All plots display CD62L vs Granzyme B contour plots of CD8$^+$ gated cells.

Figure 11:
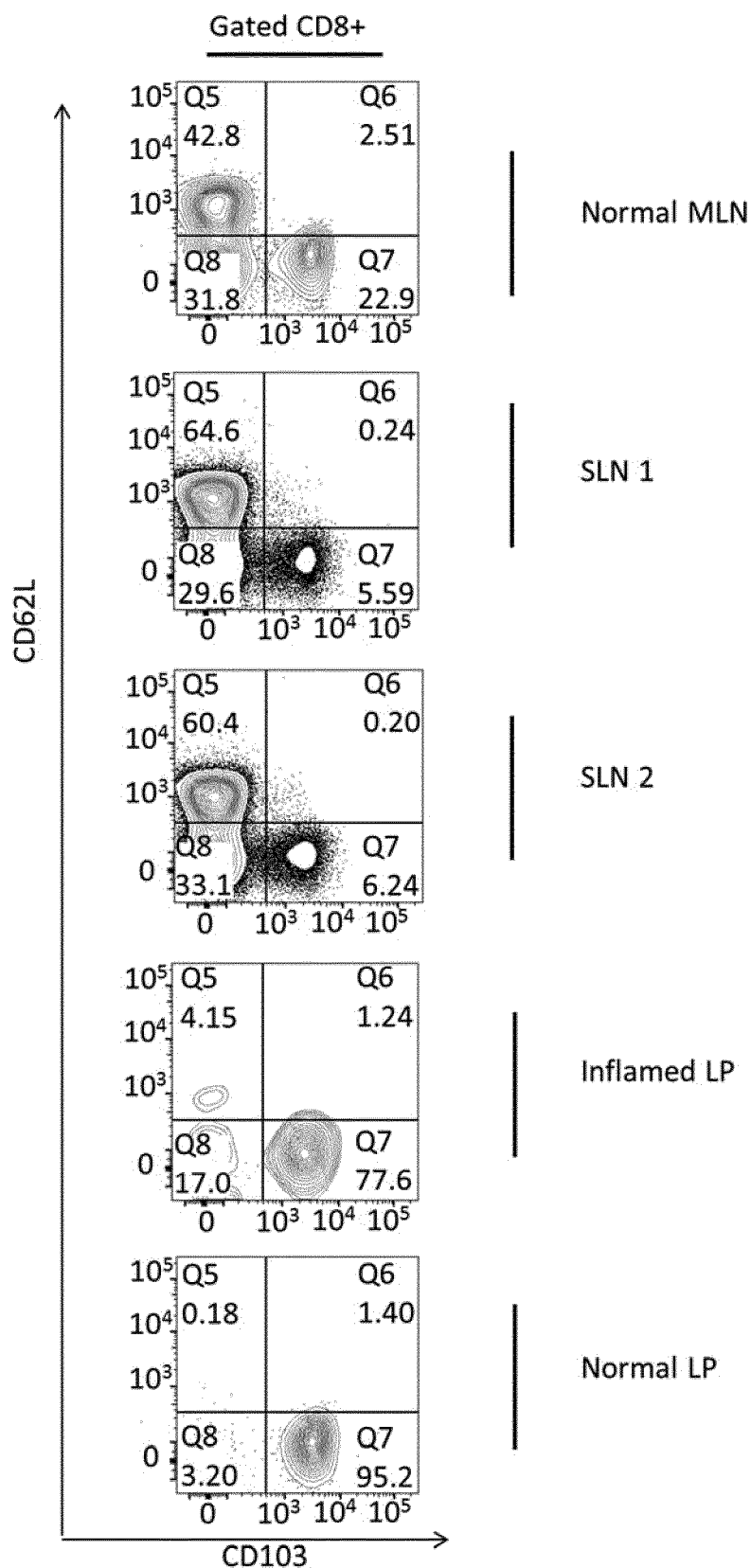

FIG. 11. CD8$^+$CD103$^+$ T-cells are largely local CD62L$^-$ character in intestinal tissues and are acutely diminished in relative abundance in the inflamed tissues of CD patients. Single cell suspensions prepared from indicated resected tissues of a representative CD patient with ileocaecal disease and were immediately stained with the indicated antibodies. All plots display CD62L vs CD103 contour plots of CD8$^+$ gated cells.

Figure 12:
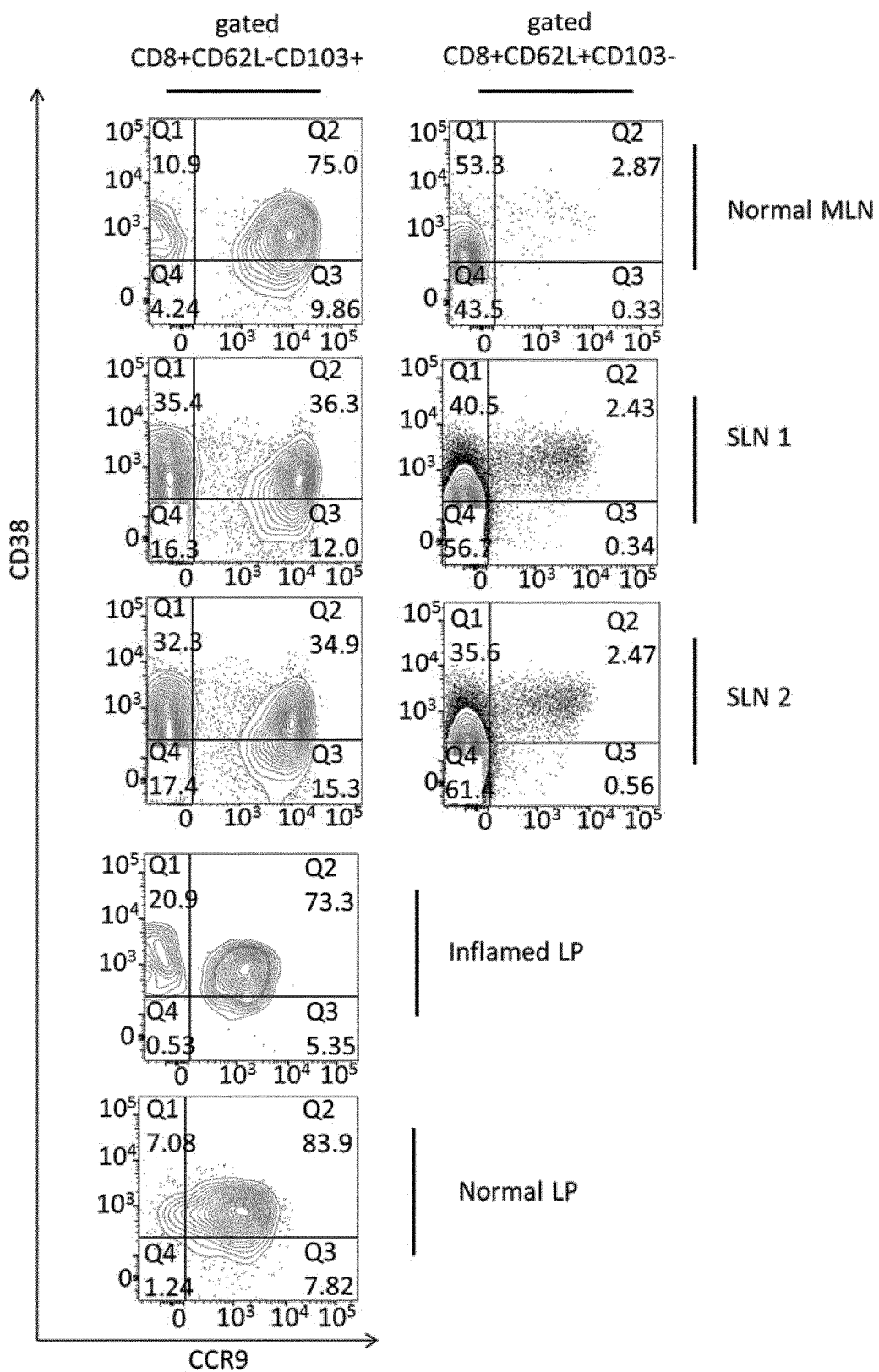

FIG. 12. CD8$^+$CD62L$^-$CD103$^+$ T-cells are highly enriched for CD38 and CCR9 expression in intestinal tissues of CD patient where CCR9 expression is acutely diminished in inflamed tissues. Single cell suspensions prepared from indicated resected tissues of a representative CD patient with ileocaecal disease and were immediately stained with the indicated antibodies. All plots display CD38 vs CCR9 of CD8$^+$CD62L$^-$CD103$^+$ cells (left panels) CD8$^+$CD62L$^+$CD103$^-$ (right panels).

Figure 13:
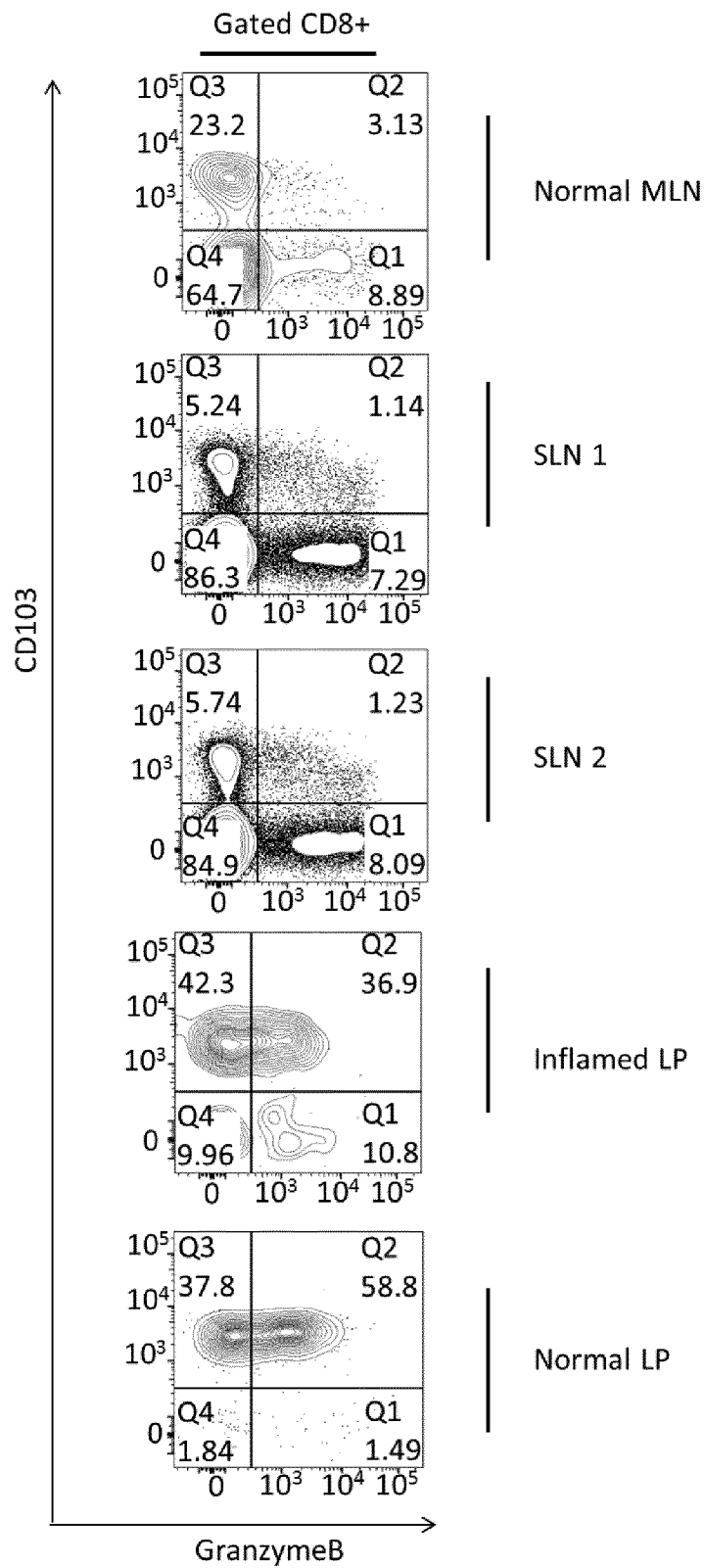

FIG. 13. CD8$^+$GranzymeB$^+$ T-cells generally do not express CD103 in MLN of patients but may express CD103$^+$ in LP. Single cell suspensions prepared from indicated resected tissues of a representative CD patient with ileocaecal disease and were immediately stained with the indicated antibodies. All plots display CD103 vs GranzymeB contour plots of CD8$^+$ gated cells.

Figure 14:
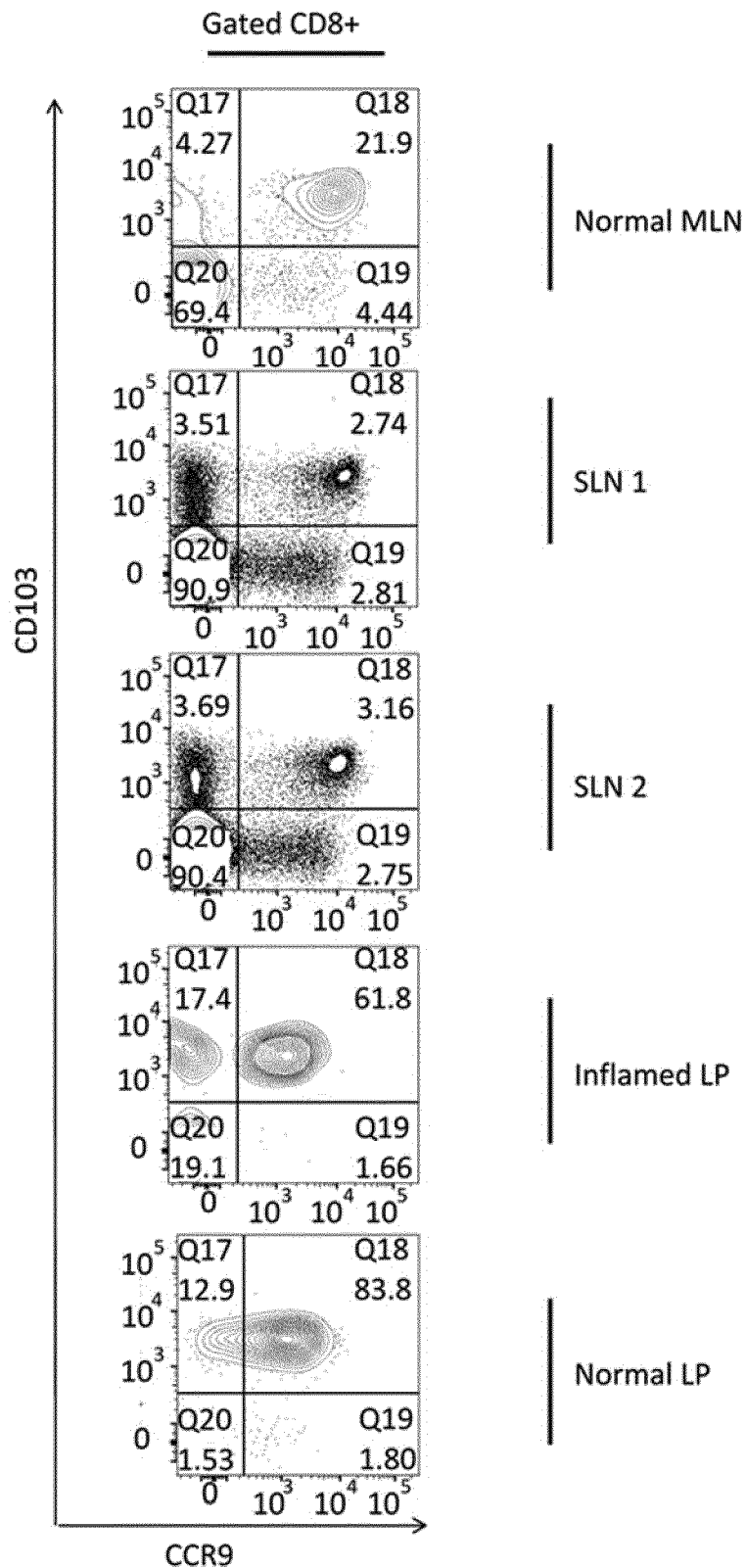

FIG. 14. Relative abundance of CD8$^+$CD103$^+$CCR9$^+$ T-cells is acutely diminished in the inflamed tissues of CD patients. Single cell suspensions prepared from indicated resected tissues of a representative CD patient with ileocaecal disease and were immediately stained with the indicated antibodies. All plots display CD103 vs CCR9 contour plots of CD8$^+$ gated cells.

Figure 15:
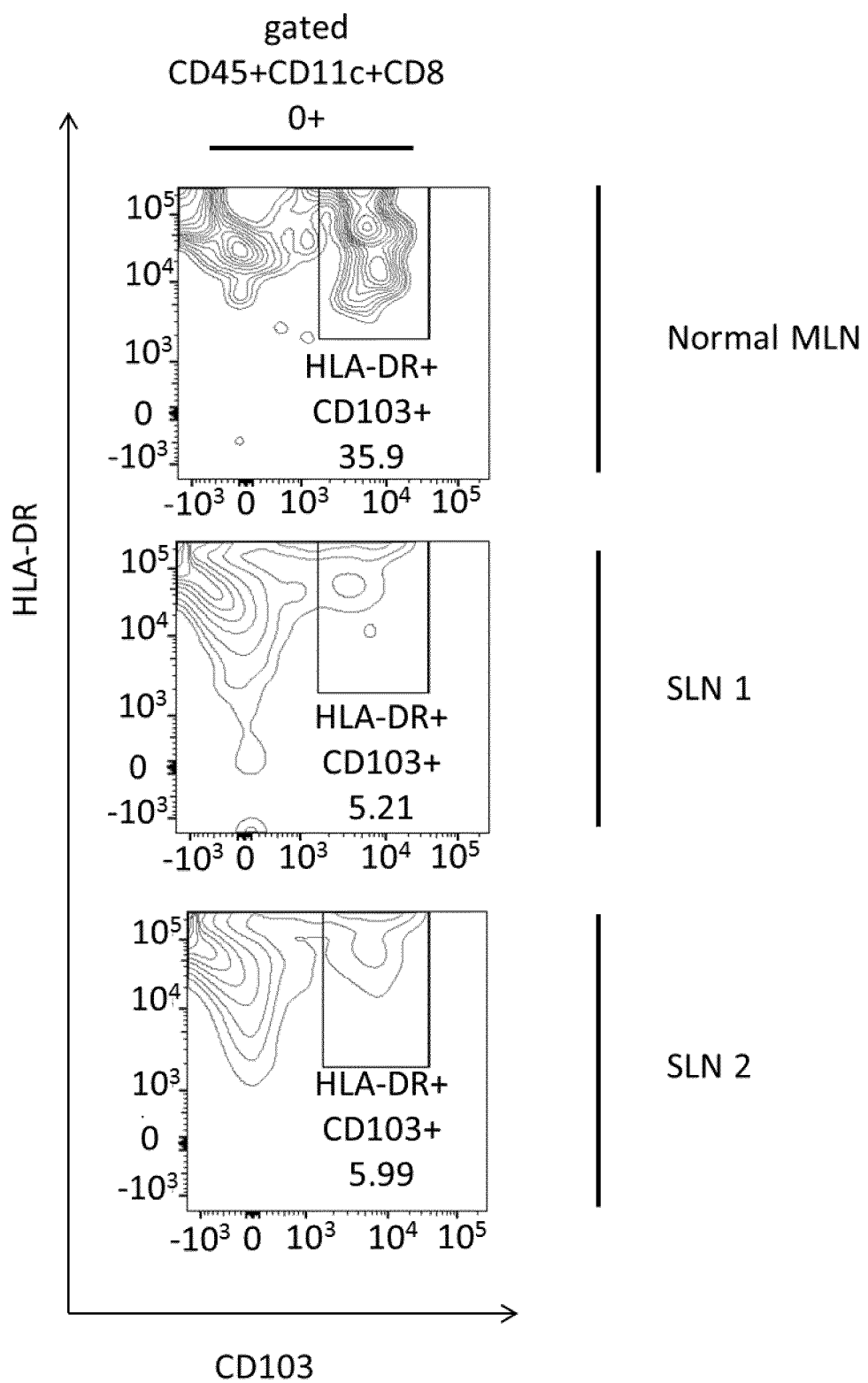

FIG. 15. Diminished representation of CD45$^+$CD11c$^{hi}$CD80$^+$HLA-DR$^{hi}$CD103$^+$ DCs in inflamed MLN of CD patients. Single cell suspensions prepared from indicated resected tissues of a representative CD patient with ileocaecal disease and were immediately stained with the indicated antibodies. All plots display HLA-DR vs CD103 of CD45$^+$CD11c$^{hi}$CD80$^+$ cells.

FIG. 16. T-cell Migratory-type surface markers correlated with CD8$^+$CD103$^+$ mucosal T-cells. PBMC recovered from healthy donor blood over ficoll were immediately labelled with indicated antibodies and analysed by flow cytometry in a high throughput screen. A) Total CD8 lymphocytes expressed as CD8 vs CD103 dotplot. B) CD8$^+$CD103$^-$ cells expressed as SSC vs CD54 contour plot. C) CD8$^+$CD103$^+$ cells expressed as SSC vs CD54 contour plot. D) Summary of ranked preferable migratory markers of X$^+$/X$^-$ condition for identification of regulatory T-cells.

FIG. 17. Example of T-cell Functional-type surface markers correlated with CD8$^+$CD103$^+$ mucosal T-cells. PBMC recovered from healthy donor blood over ficoll were immediately labelled with indicated antibodies and analysed by flow cytometry in a high throughput screen. A) Total CD8 lymphocytes expressed as CD8 vs CD103 dotplot. B) CD8$^+$CD103$^-$ cells expressed as SSC vs CD58 contour plot. C) CD8$^+$CD103$^+$ cells expressed as SSC vs CD58 contour plot.

FIG. 18. Summary of T-cell Functional-type surface markers correlated with CD8$^+$CD103$^+$ mucosal T-cells. PBMC recovered from healthy donor blood over ficoll were immediately labelled with indicated antibodies and analysed by flow cytometry in a high throughput screen as in FIG. 17. Table summarises ranked preferable functional markers of Y$^+$/Y$^-$ condition for identification of regulatory T-cells. Markers noted with 'hi' in parenthesis indicate that the population with high expression of the indicated marker is of interest, indicating that both low and negative expression populations may also exist.

Figure 19:
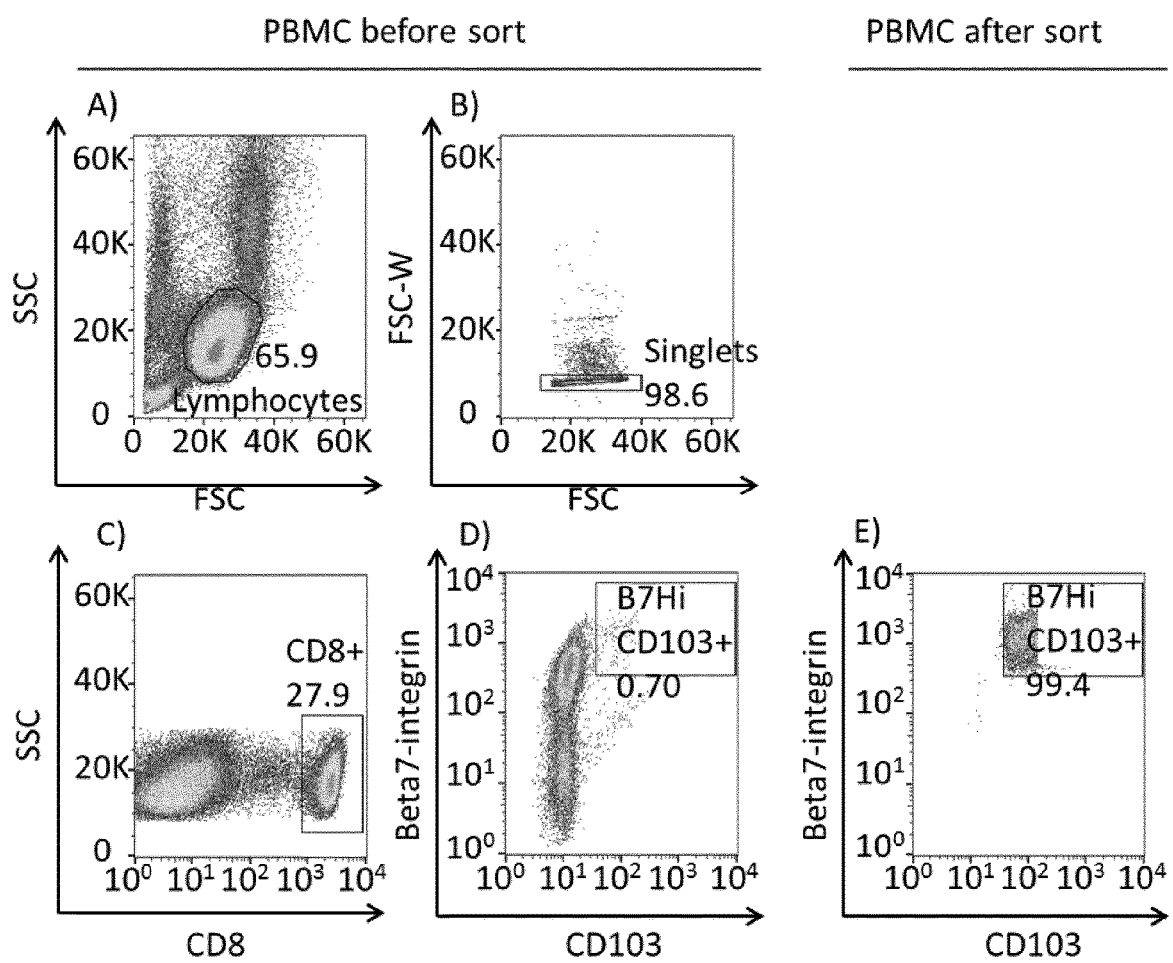

FIG. 19. Purification of CD8$^+\beta$7$^{high}$CD103$^+$ cells from peripheral blood. PBMC recovered from healthy donor blood over ficoll were immediately labelled with indicated antibodies and purified by fluorescent-activated cell sorting (FACS). Pseudocolor plots from A) to C) show lymphocytes gated from total PBMC in A) and subsequent subgates for single cells in B) and CD8+ cells in C). Plot D) redisplays total CD8+ lymphocytes as Beta7-integrin vs CD103 and defines a gate around the rare sub-population Beta7-integrin$^{Hi}$ CD103k. Plot E) shows the enrichment of the rare Beta7-integrin$^{Hi}$ CD103$^+$ sub-population of CD8 cells sorted according to the gating strategy outlined in plots A) to E) and re-analyzed by flow cytometry for the degree of sort purity.

Figure 20:
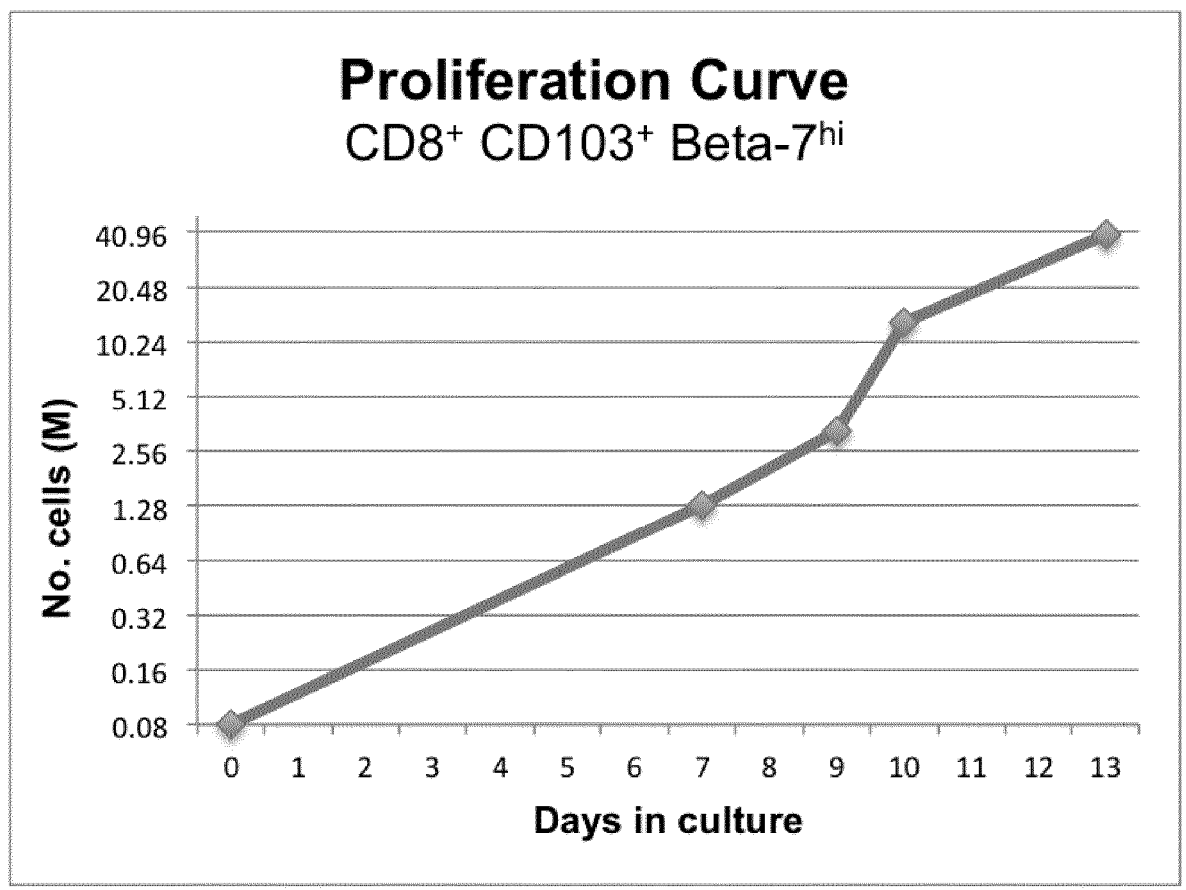

FIG. 20. In vitro Expansion of CD8$^+\beta$7$^{high}$CD103$^+$ T-cells. The subset of CD8$^+\beta$7$^{high}$CD103$^+$ enriched for Tregs was highly purified by FACS (FIG. 19), and was cultured over several days. The proliferation curve displays the expansion of a starting pool of 80,000 sorted cells reaching almost 40 millions cells over 13 days of culture.

Figure 21:
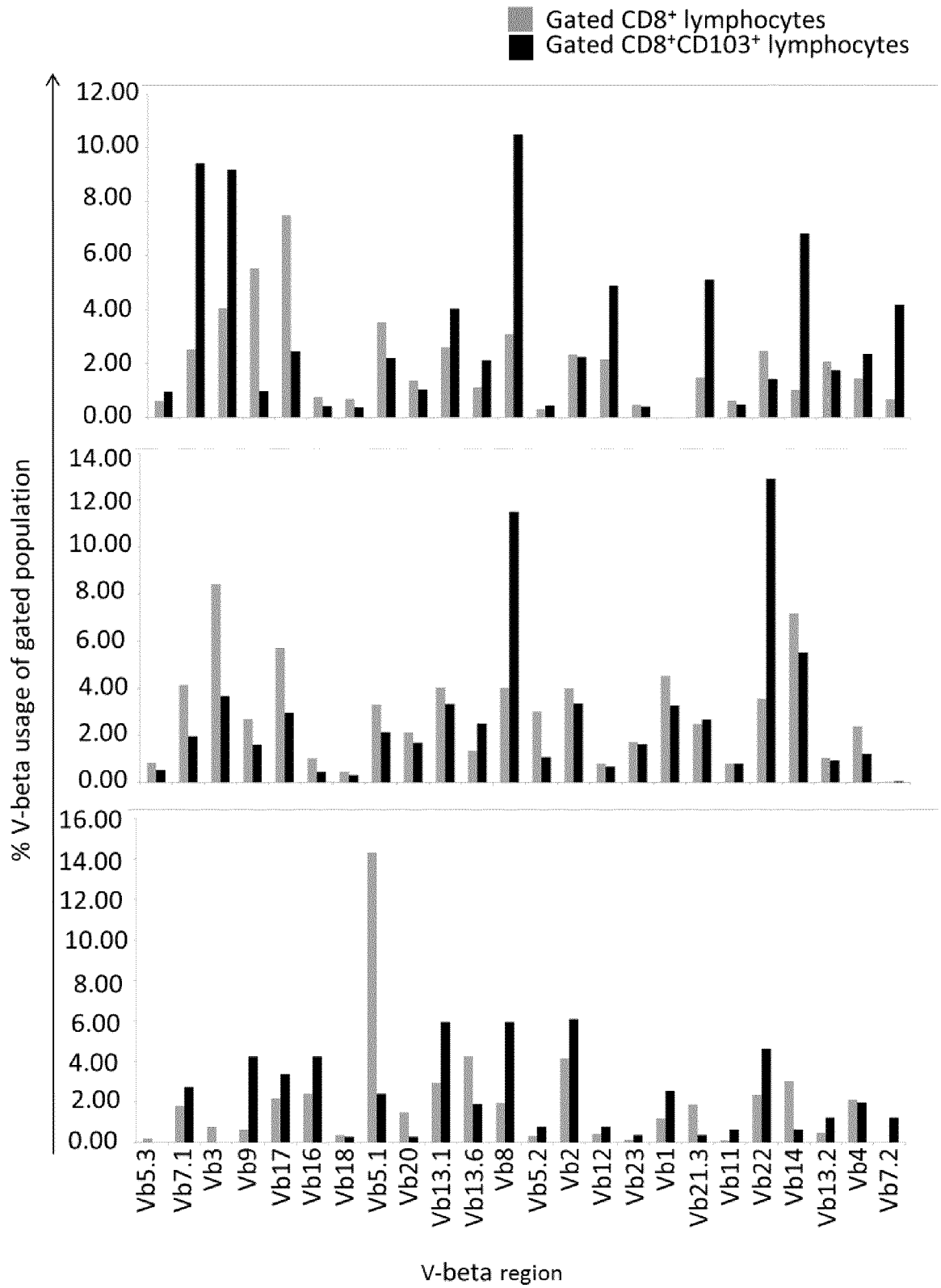

FIG. 21. Peripheral CD8$^+$CD103$^+$ T-cells have skewed Vβ usage compared to total CD8 cells. PBMC recovered from blood of three healthy donors over ficoll were immediately labelled with CD45, CD8 and CD103 antibodies in addition panels of Vβ-specific antibodies and analysed by flow cytometry. Coverage of donor C11 (top panel) was CD8$^+$48.56% and CD8$^+$CD103$^+$ 73.48%. Coverage of donor C26 (middle panel) was CD8$^+$69.46% and CD8$^+$CD103$^+$ 66.57%. Coverage of donor C34 (bottom panel) was CD8$^+$ 49.43% and CD8$^+$CD103$^+$ 52.42%.

Based on experiments, the inventors have made the following observations: CD8 Tregs in the human peripheral blood may be identified and analytically and/or physically enriched through small-bowel tropic cell surface marker sets, and these putative CD8 Treg cells are strongly diminished in numbers within the inflamed tissues of CD patients. In additional the mechanistic basis of this immunological defect in CD patients is proposed to embody a numerical deficiency in CD103$^+$ DC in inflamed tissues of CD patients. Mucosal emigrant and mucosal tropic Tregs as defined by the presented marker sets are considered as therapeutic candidates for the management of CD and other IBDs. Cells of the various identified compositions can be non-invasively recovered from peripheral blood preparations an expanded in vitro. These cells may optionally be repatterned to express correct homing receptors with addition of specific recombinant protein and chemical stimuli in vitro. Preparing targeted Treg subpopulations in this manner is proposed to restrict TCR clonal diversity to clonotypes specific for tissue-associated antigens. This supported by a skewed Vβ usage within the mucosal CD8+ populations observed in peripheral circulation, when compared to non-mucosal populations.

The general fundamental difference between CD4 and CD8 cells is that CD4 cells primarily engage with MHCII-antigen complexes, while CD8 engage MHCI-antigen complexes. In this sense, CD4 cells can be considered to engage antigens derived extrinsically to the cell, while CD8 engage antigens derived intrinsically.

CD8 T-cells are primarily considered to be cytotoxic effectors that eliminate virally infected and tumour host cells, for instance. While CD8 cells have been recognised to contain regulatory immunosuppressive subsets, there are few if any surface markers that reliably identify CD8 Treg cells. There have been several markers proposed to partly define CD8 Tregs, or at least subsets of CD8 Tregs. These include FOXP3, similar to that of CD4 Tregs, CD28 and CD103. What was of significant interest to was the proposition that CD8 Tregs were positive for CD103. We considered it likely that this is simply coincidental to the fact a that a large proportion of CD8 Tregs have a propensity to dominantly recirculate to the small intestine as part of oral tolerance mechanisms. Indeed, it stands to reason that a large proportion of CD8 Tregs are involved with the small intestinal mucosa, being by far the largest site of direct interaction between potential pathogens and the immune system. The possibility that small-intestinal homing and retention phenotype is indicative of CD8 Treg characteristics in the peripheral blood of humans was thus investigated.

FIG. 1 presents an analysis of blood from a healthy donor where CD8 cells are gated and displayed as $\beta7$ vs $\alpha4$ dotplots. Our expectation is that CD4 cells with a $\alpha4^+\beta7^{hi}$ phenotype will be highly enriched for CD103, and naturally CCR9 as a strongly co-expressed marker (note, figures designate $\beta7^{hi}$ as B7++). Cells within gates presented FIG. 1a are displayed as CD103 vs CCR9 contour plots in FIG. 1b to FIG. 1e. As anticipated, the $\alpha4^+\beta7^{hi}$ population is highly enriched for CD103, with some 97% of all cells expressing CD103. This population is also highly enriched for CCR9 expression (FIG. 1b).

To confirm and expand the relationship between CD103 expression and the expression of $\alpha4$ and $\beta7-$ integrins, one can treat the same data in a differing manner. FIG. 2a simply shows gated CD8 cells as a CD8 vs CD103 dotplot. From here, total gated CD103− and CD103+ cells are displayed a $\beta7$ vs $\alpha4$ dotplots in FIGS. 2b and 2c respectively. The negative population appears as a standard pool of CD8 T-cells with regard to $\beta7$ and $\alpha4$ expression, although strikingly lack the expression of a $\alpha4^+\beta7^{hi}$ population (FIG. 2b). In contrast the CD103+ population is highly enriched for the $\alpha4^+\beta7^{hi}$ (FIG. 2b and 2c, and compare FIG. 1a). We can also observe the enrichment of cells of another rare population, those that carry $\beta7$ expression, but lack $\alpha4$. The tissue origin of these cells that likely express the $\alpha E\beta7$ pair in the absence of $\alpha4\beta7$, is unclear.

This data can be used to visualise the quite clear expression of CD103 on the $\beta7^{hi}$ population (FIG. 3a). This CD8$^+\beta7^{hi}$CD103$^+$ population is highly enriched for $\alpha4^+$CCR9$^+$ cells (FIGS. 3b and 3c).

To investigate whether the identified cells of CD8$^+\alpha4^+\beta7^{high}\alpha E^+$CCR9$^+$ are of a Treg nature, CD8 cytotoxic markers granzyme B and perforin were analysed within the various populations presented above. This was conducted on the background of higher $\alpha E\beta7$ resolution where two distinct subsets CD103+ cells can be distinguished based on their $\beta7$ expression (FIG. 4a). Of all CD8 T-cells in circulation, some 30% are positive for either GranzymeB or Perforin and GranzymeB cytotoxic markers (FIG. 4b) However, almost no cytotoxic marker expression is observed in the CD8$^+\beta7^{high}$CD103$^+$ or CD8$^+\beta7^+$CD103$^+$ (FIGS. 4c and d). These data are consistent with a Treg character of CD8$^+\alpha4^+\beta7^{high}\alpha E^+$CCR9$^+$ cells.

To further expand the observations from FIGS. 1 to 4, the CCR9-Granzyme relationships of CD8 cells were investigated (FIG. 5). As expected, CD8$^+\beta7^{high}$CD103$^+$ are highly enriched for CCR9 expression and do not express GranzymeB (FIG. 5c). Further to this, inside this CD8$^+$ $\beta7^{high}$CD103$^+$ population, CCR9$^-$ cells have around triple the relative abundance of GranzymeB$^+$ cells. Interestingly, the bulk of remaining CCR9+ cells in the peripheral CD8 pool are of CD8$^+\beta7^+$CD103$^-$ character (FIG. 5e), while almost no CCR9 expression is observed on CD8$^+\beta7^+$CD103$^+$ (FIG. 5d). This latter CD8$^+\beta7^+$CD103$^+$ population do not ubiquitously express $\alpha4$ integrin, suggesting a distinct tissue origin of these cells (not shown). In general, CCR9+ CD8 cells do not express significant levels of cytotoxic Tcell markers.

It is hypothesised that CD8$^+\beta7^+$CD103$^-$ cells with CCR9 expression could represent recent thymic emigrants. To address this, CCR9 and CD62L relationships were investigated in the CD8$^+\beta7^{-/+/high}$CD103$^{-/+}$ populations (FIG. 6). First we may observe the fact that in total CD8 T-cells CD62L negativity correlates with a CCR9$^{high}$ phenotype, while CD62L positivity correlates with a CCR9$^+$ phenotype (FIG. 6b). Consistent with CD8$^+\beta7^+$CD103$^-$CCR9$^+$ cells representing recent thymic emigrants, these cells are enriched for CD62L positivity (FIG. 6e). Conversely, CD8$^+$ $\beta7^{high}$CD103$^+$ do not express significant levels of CD62L, suggesting that they could be enriched for a mucoscal emigrant population considering their high expression of $\alpha4$, $\beta7$, CD103 and CCR9 (FIG. 6c).

To further confirm both thymic emigrant nature of CD8$^+$ $\beta7^+$CD103$^-$ cells, and indeed the expected antigen-experienced nature of CD8$^+\beta7^{hi}$CD103$^+$ cells, the expression of CCR7 and CD45RA was analysed on these subpopulations. Firstly, nearly all CCR9$^+$CD45RA$^-$ cells in peripheral circulation were contained within the CD8$^+\beta7^{hi}$CD103$^+$ population (FIGS. 7 b and c), confirming their activated nature and supporting that this is a population of activated/proliferating mucosal emigrants. Conversely, the CD8$^+\beta7^+$CD103$^-$ cells that express also CCR9 are almost exclusively express CD45RA (FIG. 7e), supporting the expectation that these cells represent nave recent thymic emigrants. In addition it is observed that CD8$^+\beta7^+$CD103$^+$ cells, which do not generally express CCR9 are of an activated CD45RA− nature (FIG. 7d). This suggests that these cells could be activated emigrants from distinct mucosal, or nonmucosal tissues. The recent thymic emigrant nature of CD8$^+\beta7^+$CD103$^-$ cells was further confirmed by the high enrichment of CCR7 expression within this population (FIG. 8e).

Considering the observations above, it was considered that CD patients with active disease might show a distortion of mucosal emigrant CD8 populations in peripheral circulation. These various populations of CD8$^+$ were investigated in the peripheral blood of a cohort of 10 CD patients with active disease and 10 healthy controls by flow cytometry (FIG. 9). No difference was observed in the percentage of $\alpha4^+\beta7^{high}$ cells among all CD8$^+$ lymphocytes (FIG. 9a), nor a difference in total CD103$^+$ cells among all CD8+ lymphocytes (FIG. 9b) between CD patients and healthy controls. However, the percentage of cells expressing CCR9 was significantly diminished in CD patients in both CD8$^+\alpha4^+$ $\beta7^{hi}$CD103$^+$ and CD8$^+\alpha4^+\beta7^+$CD103$^+$ peripheral cell populations (FIG. 9c). This is underscored by reduced percentage of CCR9+ cells among all CD8$^+$CD103$^+$ and CD8$^+$CD103$^-$ cells alike (FIG. 9d). Among total CD8+ cells, a reduced percentage of cells carried CD62L$^-$CCR9$^+$ marking, while the percentage of CD62L$^+$CCR9$^+$ cells was unchanged (FIG. 9e). Taken together, these results suggest sufficient export CD8$^+$α4$^+$β7$^{hi}$(CD103$^+$) cells from mucosa in CD patients, but an acute defect in the CCR9 expression in these cells. Conversely, the total percentage of CD62L$^+$CCR9$^+$ recent thymic emigrants remains unchanged.

To further investigate the possibility that CD8 cells derived from the intestinal mucosa with migratory behaviours, CD8 cells within normal and inflamed tissues of the small bowel from CD patients were analysed. First it was confirmed that GranzymeB$^+$ CD8 Tcells are largely of a local character in intestinal tissues, since GranzymeB and CD62L expression are mutually exclusive in MLN (FIG. 10). Importantly, one does not observe CD62L expression in LP tissues shw. Interestingly, the CD8$^+$GranzymeB$^+$ population is of the same relative abundance in inflamed and normal tissues of CD patients (FIG. 10). This suggests that the inflammation in these tissues is not directly driven by an expansion of CD8 cytotoxic T-cells.

Similar to the cytotoxic CD8 T-cells present in the MLN and LP, CD103$^+$CD8 are largely of a local character in these intestinal tissues, since CD103 and CD62L expression are mutually exclusive (FIG. 11). In contrast, while GranzymeB$^+$ cells are present with the same relative abundance in normal and inflamed tissues, the CD103$^+$ CD8 T-cell population is significantly diminished in both SLN and inflamed LP (FIG. 11).

To further characterise the nature of CD103$^+$ CD8 cells in MLN and LP, expression of CD38 and CCR9 was investigated (FIG. 12). CD8$^+$CD62L$^-$CD103$^+$ T-cells are highly enriched in normal MLN for CD38 and CCR9 expression. This is in contrast to the low expression of both CD38 and CCR9 in CD8$^+$CD62L$^+$CD103$^-$ T-cells, which supports the locally-experienced and migratory nature of the CD8$^+$CD62L$^-$CD103$^+$ subset. Strikingly, the expression of both CCR9 is strongly diminished on CD8$^+$CD62L$^-$CD103$^+$ cells of the SLN when compared to normal MLN (FIG. 12). CD8$^+$CD62L$^-$CD103$^+$ cells in the normal LP are almost exclusively CD38$^+$CCR9+ in nature, in further support of the local education and migratory nature of CD8$^+$CD62L$^-$CD103$^+$ cells. Similar SLN, inflamed LP shows are reduction in CCR9 expression, but in this tissue maintain CD38 expression.

In analogy to the blood analyses presented in FIGS. 4 to 6, the CD103 expressing CD8 cells in the MLN and SLN largely do not express GranzymeB (FIG. 13). In contrast, however, GranzymeB cells in both inflamed and normal LP strongly express CD103, however there is notable reduction in the CD103 expression on both GranzymeB positive and negative cells in the inflamed LP. Collectively, these observations suggest that resident cells of the LP, regardless of functional phenotype, are capable of expressing CD103. However, cells migrating extrinsically, or raised environments other than the LP but endowed with LP homing properties, are largely of noncytotoxic nature. Additional cues not investigated could be responsible for cytotoxic T-cell retention in the LP, or migrating cytotoxic cells are culled in non-mucosal environments. Overall these results points towards a defect in patterning of non-cytotoxic T-cell migratory cues.

To directly visualise a hypothesised defect in migratory behaviour of CD8 cells, CD103 and CCR9 double positivity was investigated in the small bowel tissues of CD patients (FIG. 14). In normal MLN CD8$^+$CD103$^+$CCR9$^+$ cells account for roughly 22% of all CD8 cells, while this acutely diminished to ~3% in SLN. Similarly, a vast majority of cells in normal LP are double positive for CD103 and CCR9, while both expression of CCR9 or CCR9/CD103 is reduced in inflamed LP.

Overall these results are suggestive of a defect in patterning of non-cytotoxic T-cell migratory cues. The DC subset that is responsible for patterning this receptor expression on T-cells are known to be a CD103$^+$ DC subset. The possibility of a numerical deficiency in this CD103$^+$ DC population was tested as a possible cause of CCR9 and CD103 deficiency. FIG. 15 shows analysis of CD45$^+$CD11c$^{hi}$CD80$^+$HLA-DR$^{hi}$CD103$^+$ DC in the healthy MLN and disease-draining SLN of a CD patient. Strikingly, there is huge numerical deficiency in the CD103$^+$ subset of HLA-DR$^{hi}$ DC cells in the SLN. Sufficient cell numbers could not be recovered for a reliable analysis of inflamed and normal LP from this patient. However, limited analyses show a similar trend (not shown).

To further identify migratory markers on peripheral mucosal emigrant CD8$^+$ cells high throughput screening was conducted on the basis of CD103$^+$ expression. FIG. 16 a to c shows an example of an identified marker, CD54, that is highly enriched in CD8$^+$ CD103$^+$. FIG. 16d summarises all key markers identified in this screen, and classifies them from high relevance (1) to lower relevance (3).

Similarly, a high throughput screen was conducted to identify surface markers associated with proinflammatory or regulatory function on peripheral mucosal emigrant CD8$^+$ Tcells on the basis of CD103$^+$ expression. FIG. 17 shows an example of one identified marker, CD58 that is highly enriched in CD8$^+$ CD103$^+$. FIG. 18 summarises all key markers identified in this screen, and classifies them from high relevance (1) to lower relevance (3). In general, positively correlated markers are associated with regulatory functions, while negatively correlated markers are associated with proinflammatory functions.

In order to assess the feasibility of recovering CD8$^+$β7$^{hi}$CD103$^+$ T-cells from peripheral blood at high purity, PBMCs from healthy donors were labelled and sorted on the basis of these defined markers (FIG. 19). FIG. 19 a to d show the basic gating strategy of FACS-based purification of these cells, and FIG. 19e displays achieved purity of greater than 99%.

As proof of concept that CD8$^+$β7$^{hi}$CD103$^+$ purified from peripheral blood of could be expanded as a therapeutic population, cells purified by FACS as described in FIG. 19 were expanded with recombinant stimuli in vitro. FIG. 20 displays a representative growth curve of such an expansion.

Finally, to test the hypothesis that mucosal emigrant CD8+ cells in peripheral circulation are in some way clonally restricted due to their activated, emigrant and recirculating nature, a assessment of Vβ usage among CD8$^+$CD103$^+$ in peripheral circulation was conducted (FIG. 21). Across three healthy donors, the usage of Vβ segments was markedly different between CD8$^+$CD103$^+$ and the total pool of CD8$^+$ lymphocytes. This indirectly supports the proposal that CD8$^+$CD103$^+$ mucosal emigrant Tregs are activated against a restricted set of antigens in the mucosa, and exported for recirculation in order to support regional and/or systemic tolerance.

Experimental Material and Methods
Material

Fluorochrome-conjugated antibodies were obtained from BD Biosciences or BioLegend; CD4-FITC, CD4-PE/Cy7 (OKT4), CD25-APC (2A3, M-A251), CD25-PE/Cy7 (BC960, M-A251), CD38-BV421 (HIRT2), CD38-PE (HIT2), CD45RO-PerCP/Cy5.5 (UCHL1) CD49d-PE/Cy7 (9F10), CD62L-PE/Cy7 (DREG-56), CD127-PerCP/Cy5.5, CD127-PE (A019D5, HIL-7R-M21), FOXP3-PE (259D/C7), FOXP3-AlexaFluor647 (206D), integrinβ7-PerCP/Cy5.5, integrinβ7-FITC (F1B27) CD62L BV421 (DREG-55), CD4 BV510 (SK3), CD25 BV605 (2A3), CD1c PE (L161), CD3 FITC (HIT3a), CD3 PE-CF594 (UCHT1), CD3 APC-H7 (SK7), CD4 BV605 (RPA-T4), CD4 PerCP (SK3), CD4 APC (RPA-T4), CD4 APC-H7 (RPA-T4), CD8 BV510 (RPA-T8), CD8 BV605 (SK1), CD8 BV786 (RPA-T8), CD8 Alexa 488 (RPA-T8), CD8 PerCP-Cy5.5 (RPA-T8), CD8 PE (RPA-T8), CD8 PE-Cy7 (RPA-T8), CD8 APC-H7 (SK1), CD11a PE (HI111), CD11 b BV510 (ICRF44), CD11b PE-Cy7 (ICRF44), CD11c BV421 (B-Iy6), CD11c BV605 (B-Iy6), CD11c PE (B-Iy6), CD14 BV510 (MφP9), CD14 BV711 (MφP9), CD14 APC (M5E2), CD16 PerCP-Cy5.5 (3G8), CD16 PE (B73.1), CD18 BV421 (6,7), CD19 BV510 (SJ25C1), CD19 BV711 (SJ25C1), CD19 PE-Cy7 (SJ25C1), CD25 BV510 (M-A251), CD25 BV786 (M-A251), CD25 PerCP-Cy5.5 (M-A251), CD25 PE-Cy7 (M-A251), CD28 BV421 (CD28.2), CD28 BV605 (CD28.2), CD28 BV711 (CD28.2), CD28 FITC (CD28.2), CD28 PerCP-Cy5.5 (CD28.2), CD28 APC-H7 (CD28.2), CD29 BV510 (MAR4), CD29 PE (MAR4), CD29 APC (MAR4), CD31 BV605 (WM59), CD38 FITC (HIT2CD38), PE-CF594 (HIT2CD38), PE-Cy7 (HIT2CD38), Alexa700 (HIT2), CD38 APC-H7 (HB7), CD39 BV711 (T066), CD39 FITC (T066), CD45 BV605 (HI30), CD45 BV786 (HI30), CD45 FITC (HI30), CD45 PE (HI30), CD45 PE-Cy7 (HI30), CD45RA BV421 (HI100), CD45RA BV605 (HI100), CD45RA BV711 (HI100), CD45RA PerCP-Cy5.5 (HI100), CD45RA PE (HI100), CD45RO BV605 (UCHL1), CD45RO BV711 (UCHL1), CD45RO APC (UCHL1), CD49a PE (SR84), CD49b PE (12F1), CD49c PE (C3 II.1), CD49d BV510 (9F10), CD49d BV711 (9F10), CD49d PerCP-Cy5.5 (9F10), CD49d PE (9F10), CD49d PE-CF594 (9F10), CD49e PE (IIA1), CD49f PE (GoH3), CD56 BV510 (NCAM16.2), CD56 BV711 (NCAM16.2), CD62L BV510 (DREG-56), CD62L BV605 (DREG-56), CD69 BV605 (FN50), CD69 BV711 (FN50), CD69 PerCP-Cy5.5 (FN50), CD69 PE-Cy7 (FN50), CD73 BV605 (AD2), CD79a BV421 (HM47), CD79a PE (HM47), CD79a APC (HM47), CD79b PE (3A2-2E7), CD79b PE-Cy5 (CB3-1), CD80 BV605 (L307.4), CD80 PE (L307.4), CD80 PE-Cy7 (L307.4), CD80 APC (2D10), CD83 PerCP-Cy5.5 (HB15e), CD83 APC (HB15e), CD86 BV421 (2331), CD86 PerCP-Cy5.5 82331), CD86 APC (2331), CD103 BV711 (Ber-ACT8), CD103 FITC (Ber-ACT8), CD103 PE (Ber-ACT8), CD127 BV421 (HIL-7R-M21), CD127 BV605 (HIL-7R-M21), CD127 BV650 (HIL-7R-M21), CD127 BV711 (HIL-7R-M21), CD127 FITC (HIL-7R-M21), CD141 BV510 (1A4), CD141 PE (1A4), CD152 BV421 (BN13), CD152 BV786 (BN13), CD163 PerCP-Cy5.5 (GHI/61), CD192 BV421 (K036C2), CD196 BV421 (11A9), CD197 FITC (3D12), CD197 PerCP-Cy5.5 (150503), CD199 Alexa 488 (112509), CD199 FITC (112509), CD199 PE (112509), CD199 PE (L053E8), CD199 PE (248621), CD199 PE-Cy7 (L053E8), CD199 Alexa 647 (112509), CD199 Alexa 647 (L053E8), CD199 Alexa 647 (BUCCR9), CD199 APC (112509), CD303 BV421 (201A), CD357 APC (62), Annexin V APC, β7 integrin BV421 (F1B504), β7 integrin BV605 (F1B504), β7 integrin PE (F1B504), β7 integrin APC (F1B504), CX3CR1 PerCP-Cy5.5 (2A9-1), FoxP3 Alexa 488 (259D/C7), Granzyme B BV421 (GB11), Granzyme B FITC (GB11), Granzyme B PE-CF594 (GB11), Helios PE (22F6), HLA-A2 PE-Cy7 (BB7.2), HLA-A,B,C PE-Cy5 (G46-2.6), HLA-E PE (3D12), HLA-G PE (87G), HLA-DM PE (MaP.DM1), HLA-DR PerCP-Cy5.5 (G46-6), HLA-DR PE-Cy7 (G46-6), HLA-DR APC (G46-6), HLA-DRB1, HLA-DR, DP, DQ FITC (T039), HLA-DR, DP, DQ Alexa 647 (Tü39), HLA-DQ FITC (Tu169), IFN-g Alexa 647 (4S.63), IL-1b PE (AS10), IL-2 FITC (MQ1-17H12), IL-2 FITC (MQ1-17H12), IL-4 FITC (MP4-25D2), IL-10 APC (JES3-19F1), IL-12 FITC (C11.5), IL-17A PE (SCPL1362), IL-35 PE (6032F6), Ig κ light chain PE (G20-193), Light chain A PE (JDC-12), IgM BV605 (G20-127), IgM FITC (G20-127), IgM FITC IgM PE-Cy5 (G20-127), Lineage cocktail FITC, Perforin BV421 (5G9), Perforin Alexa 488 (δG9), Syk FITC (4D10), Syk PY352 PE (17A/P-ZAP70), Syk PY352 PE-Cy7 (17A/P-ZAP70), Syk PY352 Alexa 647 (17A/P-ZAP70), TCR αβ BV510 (T10B9.1A-31), TCR αβBV786 (T10139.1A-31), TCR γδ FITC (61), TCR γδ-1 FITC (11F2), TCR γδ PE-CF594 (61), TGF-b1 BV421 (TW4-9E7), TNF-a APC (MAb11), and unlabelled antibodies were obtained from BD Biosciecnes; CD1a (HI149), CD28 (L293), CD51/61 (23C6), CD1b (M-T101), CD29 (HUTS-21), CD53 (H129), CD1d (CD1d42), CD30 (BerH8), CD54 (LB-2), CD2 (RPA-2.10), CD31 (WM59), CD55 (IA10), CD3 (HIT 3a), CD32 (FL18.26), CD56 (6159), CD4 (RPA-T4), CD33 (HIM3-4), CD57 (NK-1), CD4v4 (L120), CD34 (581), CD58 (1C3), CD5 (L17F12), CD35 (E11), CD59 (p282, H19), CD6 (M-T605), CD36 (C638, NL07), CD61 (VI-PL2), CD7 (M-T701), CD37 (M-6371), CD62E (68-5H11), CD8a (SK1), CD38 (HIT 2), CD62L (Dreg 56), CD8b (2ST 8.5H7), CD39 (TU66), CD62P (AK-4), CD9 (M-L13), CD40 (5C3), CD63 (H5C6), CD10 (H110a), CD41a (HIP8), CD64 (10.1), CD11a (G43-25B), CD41b (HIP2), CD66 (a,c,d,e) (61.1/CD66), CD11 b (D12), CD42a (ALMA.16), CD66b (G10F5), CD11c (B-Iy 6), CD42b (HIP1), CD66f (IID10), CD13 (WM15), CD43 (1G10), CD69 (FN50), CD14 (M5E2), CD44 (G44-26), CD70 (Ki-24), CD15 (H198), CD45 (H130), CD71 (M-A712), CD15s (CSLEX1), CD45RA (HI100), CD72 (J4-117), CD16 (3G8), CD45R6 (MT4), CD73 (AD2), CD18 (6.7), CD45RO (UCHL1), CD74 (M-B741), CD19 (H1619), CD46 (E4.3), CD75 (LN1), CD20 (2H7), CD47 (66H12), CD77 (5B5), CD21 (B-Iy 4), CD48 (T U145), CD79b (C63-1), CD22 (H1622 CD49a SR84 CD80 L307.4 CD23 EBVCS-5 CD49b AK-7 CD81 JS-81), CD24 (ML5), CD49c (C3 II.1), CD83 (H615e), CD25 (M-A251), CD49d (9F10), CD84 (2G7), CD26 (M-A261), CD49e (VC5), CD85 (GHI/75), CD27 (M-T271), CD50 (TU41), CD86 (2331, FUN-1), CD123 (9F5), CD172b (B4B6), CD87 (VIM5), CD124 (hIL4R-M57), CD177 (MEM-166), CD88 (D53-1473), CD126 (M5), CD178 (NOK-1), CD89 (A59), CD127 (hIL-7R-M21), CD180 (G28-8), CD90 (5E10), CD128b (6C6), CD181 (5A12), CD91 (A2MR-alpha 2), CD130 (AM64), CD183 (1C6/CXCR3), CDw93 (R139), CD134 (ACT35), CD184 (12G5), CD94 (HP-3D9), CD135 (4G8), CD193 (5E8), CD95 (DX2), CD137 (4134-1), CD195 (2D7/CCR5), CD97 (VIM3b), CD137 (Ligand C65-485), CD196 (11A9), CD98 (UM7F8), CD138 (Mil 5), CD197 (2H4), CD99 (TU12), CD140a (alpha R1), CD200 (MRC OX-104), CD99R (HIT 4), CD140b (28D4), CD205 (MG38), CD100 (A8), CD141 (1A4), CD206 (19.2), CD102 (C6R-1C2/2.1), CD142 (HTF-1), CD209 (DCN46), CD103 (Ber-ACT8), CD144 (55-7H1), CD220 (3B6/IR), CD105 (266), CD146 (P1H12), CD221 (3B7), CD106 (51-10C9), CD147 (HIM6), CD226 (DX11), CD107a (H4A3), CD150 (A12), CD227 (HMPV), CD107b (H464), CD151 (14A2.H1), CD229 (HLy9.1.25), CD108 (KS-2), CD152 (BN13), CD231 (M3-3D9, SN1a), CD109 (TEA 2/16), CD153 (D2-1173), CD235a (GA-R2, HIR2), CD112 (R2.525), CD154

(TRAP1), CD243 (17F9), CD114 (LMM741), CD158a (HP-3E4), CD244 (2-69), CD116 (M5D12), CD158b (CH-L), CD255 (CARL-1), CD117 (Y B5.B8), CD161 (DX12), CD268 (1101), CD118 (12D3), CD162 (KPL-1), CD271 (C40-1457), CD119 (GIR-208), CD163 (GHI/61), CD273 (MIH18), CD120a (MABTNFR1-A1), CD164 (N666), CD274 (MIH1), CD121a (HIL1R-M1), CD165 (SN2), CD275 (2D3/B7-H2), CD121b (MNC2), CD166 (3A6), CD278 (DX29), CD122 (Mik-beta 3), CD171 (5G3), CD279 (MIH4), fMLP receptor (5F1), Ms IgG2a IC (G155-178), CD282 (11G7), γδTCR (61), Ms IgG2b IC (27-35), CD305 (DX26), HPC (13139), Ms IgG3 IC (J606), CD309 (89106), HLA-A,B,C (G46-2.6), CD49f (GoH3), CD314 (1D11), HLA-A2 (13137.2), CD104 (439-9B), CD321 (M.AB.F11), HLA-DQ (TU169), CD120b (hTNFR-M1), CDw327 (E20-1232), HLA-DR (G46-6, L243), CD132 (TUGh4), CDw328 (F023-420), HLA-DR, DP, DQ (TU39), CD201 (RCR-252), CDw329 (E10-286), Invariant NK T (61311), CD210 (3F9), CD335 (9E2/NKp46), Disialoganglioside GD2 (14.G2a), CD212 (266/12beta 2), CD336 (P44-8.1), MIC A/B (6D4), CD267 (1A1-K21-M22), CD337 (P30-15), NKB1 (DX9), CD294 (BM16), CD338 (5D3), SSEA-1 (MC480), SSEA-3 (MC631), CD304 (Neu24.7), SSEA-4 (MC813-70), CLA (HECA-452), αβT CR (T10139.1A-31), TRA-1-60 (TRA-1-60), Integrin β7 (F16504), β2-microglobulin (TU99), TRA-1-81 (TRA-1-81), Rt IgM IC (R4-22), BLTR-1 (203/14F11), Vβ 23 (AHUT 7), Rt IgG1 IC (R3-34), CLIP (CerCLIP), Vβ 8 (JR2), Rt IgG2a IC (R35-95), CMRF-44 (CMRF44), CD326 (EBA-1), Rt IgG2b IC (A95-1), CMRF-56 (CMRF56), Ms IgM IC (G155-228), EGF Receptor (EGFR1), Ms IgG1 IC (MOPC-21) and Zombie NIR™ Fixable Viability Kit or BD Biosciences; CD4-PacificBlue (RPA-T4); collagenaseIV, DNaseI, DTT, EDTA and sodium azide from SigmaAldrich; FicollPaquePlus from GEHealthcare, RPMI media, BSA and FCS from Life Technologies; 10Test Beta Mark TCR V Kit from Beckman Coulter.

Patients and Tissue Preparation

All subjects gave their written informed consent under the Helsinki guidelines and local ethics committee. CD patients undergoing ileoceacal resection were recruited to the study. We collected small bowel (ileum) and large bowel (ceacum/ascending colon), including MLN draining these regions. Control samples were from colorectal cancer patients undergoing right-sided hemicolectomy. Intestinal lamina propria from the small and large bowel was separated via microdissection. The dissected lamina propria was minced into 1-2 mm pieces and single cell suspensions were prepared in RPMI 1640 containing 5% FBS, 50 μg/mlgentamycin and 50 μg/ml Penicillin/Streptomycin using the Medimachine with a 50 μm Medicon (BD Biosciences). The cell suspension was filtered through a 70-μm nylon mesh (BD Biosciences), centrifuged and the pellet resuspended in FACS buffer (PBS containing 2% FBS) for subsequent antibody staining. Lymphocytes from MLN were isolated by mechanical disruption of lymph nodes after surrounding fat tissue was removed by dissection. The cell suspension was filtered through a 40-μm nylon mesh (BD Biosciences), centrifuged and the pellet resuspended in FACS buffer for subsequent antibody staining.

Patients and Blood Preparation

All subjects gave their written informed consent under the Helsinki guidelines and local ethics committee. Healthy donors were recruited to the blood cohorts. Blood drawn into EDTA tubes was diluted 1:2 in PBS with 2 mM EDTA and PBMCs collected over a FicollPaquePlus density gradient by centrifugation. PBMCs were washed 3 times in wash buffer (PBS, 0.2% BSA, 5 mM EDTA) before immediate flow cytometry.

Direct Cell Purification by FACS

Extracellular antigens were stained in FACS buffer (PBS, 2% BSA) using appropriate combinations of fluorophore-conjugated antibodies (BioLegend and BD Biosciences). Specific cell populations were purified by fluorescence-activated cell sorting (FACS) using a BD Influx cell sorter with BD FACS Software (BD Biosciences) to acquire data. Final analyses utilized FlowJo software (Tree Star Inc.).

Expansion of Sorted Cell Populations

The sorted cell populations were expanded in OpTmizer media with 2 mM Glutamax (both Life Technologies) and either autologous or commercial human serum (Sigma) using MACS GMP ExpAct Treg Kit (Miltenyi Biotec) and in the presence of recombinant human IL-2 (Miltenyi Biotec).

Row Cytometry

Zombie NIR Fixable Viability Kit (Biolegend) was used as a dead cell marker. Surface antigens were stained in FACS buffer (PBS containing 2% FBS) and intracellular FoxP3 was stained after fixation and permeabilization using the human FoxP3 buffer set (BD Biosciences). Cells were acquired using a LSRFortessa flow cytometer with Diva 8 software (BD Biosciences). Final analysis was performed using FlowJo 10 software (Tree Star Inc.).

Statistics

All data was expressed as mean±SEM. Pair wise comparisons were two-tailed MannWhitney U-tests. Significance testing of multiple parameters was calculated with Kruskal-Wallis one-way ANOVA and Dunn's post-test of selected columns. A p value <0.05 was considered significant.

Items—Specific Issues

1. Treg cells for use in the treatment of an inflammatory disease of the gastrointestinal tract, the Treg cells have signatures for
i) identifying that the T-cells are regulatory Tcells,
ii) identifying that the Treg cells are tissue type tropic, i.e they can migrate to the diseased tissue,
iii) identifying that the Treg cells are tropic with respect to the diseased tissue of the gastrointestinal tract, i.e. they are homing cells,
iv) identifying that the Treg cells are emigrant cells, i.e. they originate from the target tissue of gastrointestinal tract, and/or
v) identifying that the Treg cells are retained in the target tissue of the gastrointestinal tract,
wherein the Treg cells have the signatures i), ii) and iii) and optionally iv) and/or v), or the Treg cells have the signatures i), ii) and v) and optionally iii) and/or iv), or the Treg cells have the signatures i), iii) and optionally ii) and/or v).

2. Tregs for use according to item 1, wherein the inflammatory disease is Crohn's disease or ulcerative colitis.

3. Tregs for use according to item 2, wherein the disease is Crohn's disease which is located in the small bowel.

4. Treg cells for use according to any of the preceding items for the treatment of an inflammatory disease of the small bowel, the Treg cells have signatures for
i) identifying that the T-cells are regulatory Tcells,
ii) identifying that the Treg cells are mucosal tropic,
iii) identifying that the Treg cells are small bowel tropic, and optionally the Treg cells have signatures for
iv) identifying that the Treg cells are emigrant cells, i.e. they originate from the small bowel, and/or v) identifying that the Treg cells are retained in the small bowel.

5. Treg cells for use according to item 4 having signatures for
iv) identifying that the Treg cells are emigrant cells, i.e. they originate from the small bowel.

6. Treg cells for use according to any of items 3-5 having signatures for
v) identifying that the Treg cells are retained in the small bowel.

7. Treg cells for use according to any of the preceding items, wherein the signatures for identifying that the T-cells are regulatory T-cells are CD8$^+$, or CD8$^+$CD28$^+$.

8. Treg cells for use according to any of the preceding items, wherein the signature for identifying that the Treg cells can migrate to the diseased tissue such as the mucosal tissue is α4β7$^+$ or α4$^+$β7$^+$.

9. Treg cells for use according to any of the preceding items, wherein the signature for identifying that the Treg cells can be retained in the diseased tissue such as the mucosal tissue is is α4β7$^{high}$αE$^+$ or α4$^+$β$^{high}$αE$^+$.

10. Treg cells for use according to any of the items 3-9, wherein the signatures for identifying that the Treg cells are small bowel tropic is CCR9$^+$.

11. Treg cells for use according to any of the preceding items, wherein the signatures for identifying that the Treg cells are educated cells (emigrants) is CD62L$^-$CD38$^+$.

12. Treg cells for use according to any of the preceding items, wherein the Treg cells comprise a signature selected from the following signatures:
CD8$^+$α4$^+$β7$^+$CCR9$^+$
CD8$^+$α4$^+$β7$^{high}$αE$^+$CCR9$^+$
CD8$^+$CD28$^+$α4$^+$β7$^+$CCR9$^+$,
CD8$^+$CD28$^+$α4$^+$β7$^{high}$αE$^+$CCR9$^+$
CD8$^+$α4$^+$β7$^+$X$^+$
CD8$^+$α4$^+$β7$^{high}$αE$^+$X$^+$
CD8$^+$CD28$^+$α4$^+$β7$^+$X$^+$
CD8$^+$CD28$^+$α4$^+$β7$^{high}$αE$^+$X$^+$
CD8$^+$α4$^+$β7$^+$
CD8$^+$α4$^+$β7$^{high}$αE$^+$
CD8$^+$CD28$^+$α4$^+$β7$^+$
CD8$^+$CD28$^+$α4$^+$β7$^{high}$αE$^+$
wherein X is the signature relating to tropism of the diseased part of the gastrointestinal part and may be X$^+$ or X$^-$, wherein α4$^+$ may be substituted with α4.
and any of the signatures may also comprise CD62L$^-$CD38$^+$ 13. Treg cells for use according to any of items 3-12, wherein the small bowel disease is Crohn's disease.

14. A method for treating a patient suffering from an inflammatory disease of the gastrointestinal tract, the method comprises
a) isolating Treg cells defined in any one of items 1-13 from a tissue sample obtained from a patient suffering from the inflammatory disease of the gastrointestinal tract,
b) expanding the Treg cells in vitro,
c) optionally re-patterning the expanded Treg cells to obtain Tregs that have signatures ii) and iii) and optionally iv) and/or v), or signatures for iii) and v) and optionally ii) and/or iv) or signatures for ii) and optionally iii), iv) and/or v), wherein the signatures is for
ii) identifying that the Treg cells are tissue type tropic,
iii) identifying that the Treg cells are diseased tissue tropic,
iv) identifying that the Treg cells are emigrant cells, i.e. they originate from the target tissue, and/or
v) identifying that the Treg cells are retained in the target tissue,
d) administering the Treg cells obtained from b) or c) to the patient.

15. A method according to item 14, wherein the expanded Treg cells from step b) or c) have features as defined in any one of items 1-13.

16. A method according to item 14 or 15, wherein the tissue sample is from peripheral blood of the patient.

17. A method according to any of items 12-15, wherein the inflammatory disease of the gastrointestinal tract is Crohn's disease.

18. A method for obtaining Treg cells as defined in any one of items 1-13, the method comprises
a) isolating Treg cells defined in any one of items 1-13 from a tissue sample obtained from a patient suffering from an inflammatory disease of the gastrointestinal tract,
b) expanding the Treg cells in vitro,
c) optionally re-patterning the expanded Treg cells to obtain Tregs that have signatures signatures ii) and iii) and optionally iv) and/or v), or signatures for iii) and v) and optionally ii) and/or iv) or signatures for ii) and optionally iii), iv) and/or v), wherein the signatures is for
ii) identifying that the Treg cells are tissue type tropic,
iii) identifying that the Treg cells are diseased tissue tropic relating to the diseased part of the gastrointestinal tract,
iv) identifying that the Treg cells are emigrant cells, i.e. the originates from the target tissue of the gastrointestinal tract, and/or
v) identifying that the Treg cells are retained in the target tissue of the gastrointestinal tract.

19. A method according to item 18, wherein the inflammatory disease of the gastrointestinal tract is Crohn's disease such as Crohn's disease located in the small bowel.

20. A method according to item 18 or 19, wherein step a) comprises the recovery of mononuclear cells from patient tissue specimens, and labelling said pool of mononuclear cells with antibodies specific for appropriate markers; once labelled, cells are purified by immunoaffinity and/or flow cytometric sorting techniques to yield highly enriched or purified Treg populations of desired characteristics.

21. A method according to any of items 18-20 wherein step b) comprises recombinant T-cell stimulation in the form of anti-CD3/anti-CD28 activating antibodies in combination with IL2, or alternatively the outgrowth of Treg populations on transgenic feeder cell populations, or irradiated autologous peripheral monocytes with IL2 supplementation.

22. A method according to any of items 18-21, wherein step c) comprises the recombinant reactivation of expanded T-cell populations with anti-CD3/anti-CD28 activating antibodies and subsequent introduction of stimuli in precise combination. Stimuli include all-trans retinoic acid, Interleukin-10 and transforming growth factor-beta.

23. A method for obtaining Treg cells as defined in any one of items 1-13, the method comprising
a) providing Treg cells comprising a signature selected from CD8$^+$,
CD8$^+$δ7$^{high}$αE$^+$,
CD8$^+$CD28$^+$,
CD8$^+$CD28$^+$β$^{high}$αE$^+$,
and the above-mentioned signatures may further comprise the signature CD62L$^-$ CD38$^+$,
and
b) re-patterning the Treg cells to further comprise the signature α4β7$^+$, α4$^+$β7$^+$, α4$^+$β7$^+$X or α4$^+$β7$^+$CCR9$^+$, wherein X is as defined herein before.

24. A method according to item 23, wherein step b) comprises the recombinant reactivation of expanded T-cell populations with anti-CD3/anti-CD28 activating antibodies and subsequent introduction of stimuli including all-trans retinoic acid, Interleukin-10 and transforming growth factor-beta 25. A method for obtaining Treg cells as defined in any one of items 1-13, the method comprising
a) providing Treg cells comprising a signature selected from
CD8$^+$CCR9$^+$,
CD8$^+$β7$^{high}$αE$^+$CCR9$^+$,
CD8$^+$CD28$^+$CCR9$^+$,
CD8$^+$CD28$^+$β7$^{high}$αE$^+$±CCR9$^+$,
and the above-mentioned signatures may further comprise the signature CD62L$^-$ CD38$^+$,
and
b) re-patterning the Treg cells to further comprise the signature α4β7$^+$ or α4$^+$β7$^+$.

26. A method according to item 24, wherein step b) comprises the recombinant reactivation of expanded T-cell populations with anti-CD3/anti-CD28 activating antibodies and subsequent introduction of stimuli including all-trans retinoic acid, Interleukin-10 and transforming growth factor-beta.

27. A pharmaceutical composition comprising Treg cells as defined in any of items 1-13 dispersed in an aqueous medium.

28. Treg cells as defined in any of items 1-13.

The invention claimed is:

1. A method of treating an inflammatory or autoimmune disease of the gastrointestinal tract, comprising administering to a subject in need thereof a pharmaceutical composition consisting essentially of an isolated CD8$^+$ Treg cell population, wherein the administered cells consist of CD8$^+$ Treg cells having the following signatures:
   (i) a signature that identifies that the Treg cells are CD8$^+$ regulatory T cells selected from CD8$^+$, CD8$^+$CD122$^+$, CD8$^+$Y, or CD8$^+$CD122$^+$Y$_n$, wherein n indicates that one or more Y signatures is present,
   (ii) a signature that identifies that the Treg cells are mucosal tissue type tropic that can migrate to diseased mucosal tissue of the gastrointestinal tract, selected from α4β7$^+$, α4β7$^+$, α4β7$^+$X$_n$, or α4β7$^+$X$_n$, wherein n indicates that one or more X signatures is present,
   (iii) optionally, a signature CCR9$^+$ that identifies that the Treg cells are homing cells tropic with respect to diseased mucosal tissue of the gastrointestinal tract,
   (iv) a signature that identifies that the Treg cells are antigen-experienced emigrant cells that originate from target mucosal tissue of the gastrointestinal tract, selected from CD62L$^-$, X$_n$, Y$_p$, X$_n$Y$_p$, CD62L$^-$X$_n$, CD62L$^-$Y$_p$, and CD62L$^-$X$_n$Y$_p$, wherein n and p indicate that one or more X signatures and/or one or more Y signatures, respectively, is present, and
   (v) optionally, a signature α4$^+$αE$^+$β7$^{Hi}$ that identifies that the Treg cells are capable of being retained in the target mucosal tissue of the gastrointestinal tract,
   wherein an X signature indicates that the Treg cells can localize, have emigrated from, or are marked for preferential retention in the specific part of the gastrointestinal tract that is diseased, and is one or more selected from CD49d$^+$, CD54$^+$, CD99$^-$, CD99R$^+$, CD166$^+$, CD49a$^-$, CD49c$^-$, CD49f$^-$, CD102$^-$, CD165$^+$, CDw328$^-$, CDw329$^-$, CD37$^-$, CD38$^-$, and CD49e$^-$; and
   a Y signature indicates immunosuppressive regulatory function, and is one or more selected from CD25$^+$, CD58$^+$, CD73$^+$, CD95$^+$, CD105$^+$, CD107a$^+$, CD107b$^+$, CD122$^+$, CD244$^+$, CD268$^+$, CD274$^+$, CD31$^-$, CD35$^-$, CD39$^+$, CD41a$^+$, CD63$^+$, CD85$^-$, CD88$^+$, CD97$^+$, CD108$^+$, CD120b$^+$, CD127$^+$, CD130$^-$, CD132$^+$, CD151$^+$, CD210$^+$, CD221$^-$, CD226$^+$, CD335$^-$, CD336$^-$, EGF-R$^-$, CD66$^-$, CD126$^-$, CD150$^+$, CD161$^+$, CD195$^+$, CD200$^-$, and CD279$^+$;
   wherein the isolated CD8$^+$ Treg cell population has T-cell receptor clonal diversity restricted to clonotypes specific for antigens present in the mucosal tissue types to which the selected signatures relate.

2. The method of claim 1, wherein the inflammatory or autoimmune disease is selected from Crohn's disease and ulcerative colitis.

3. The method of claim 1, wherein the inflammatory or autoimmune disease is selected from primary sclerosing cholangitis and acute celiac disease.

4. The method according to claim 1, wherein the diseased tissue originates from inflamed tissue or tissue subject to an autoimmune disease.

5. The method according to claim 1, wherein the CD8$^+$ Treg cell population includes CD8$^+$ Treg cells having at least one of the following signatures:
CD8$^+$α4β7$^+$CD62L$^-$
CD8$^+$α4$^+$β7$^+$CD62L$^-$
CD8$^+$α4β7$^+$CD62L$^-$CCR9$^+$
CD8$^+$α4$^+$β7$^+$CD62L$^-$CCR9$^+$
CD8$^+$α4β7$^{hi}$αE$^+$CD62L$^-$
CD8$^+$α4$^+$β7$^{hi}$αE$^+$CD62L$^-$
CD8$^+$CD62L$^-$α4β7$^{high}$αE$^+$CCR9$^+$ and
CD8$^+$CD62L$^-$α4$^+$β7$^{high}$αE$^+$CCR9$^+$.

6. The method according to claim 1, wherein the CD8$^+$ Treg cell population includes CD8$^+$ Treg cells having at least one of the following signatures:
CD8$^+$α4β7$^+$CD62L$^-$X/Y
CD8$^+$α4$^+$β7$^+$CD62L$^-$X/Y
CD8$^+$α4β7$^+$CD62L$^-$CCR9$^+$X/Y
CD8$^+$α4$^+$β7$^+$CD62L$^{-CCR9+}$X/Y
CD8$^+$α4β7$^{hi}$αE$^+$CD62L$^-$X/Y
CD8$^+$α4$^+$β7$^{hi}$αE$^+$CD62L$^-$X/Y
CD8$^+$CD62L$^-$α4β7$^{high}$αE$^+$CCR9$^+$X/Y and
CD8$^+$CD62L$^-$α4$^+$β7$^{high}$αE$^+$CCR9$^+$X/Y,
   wherein X/Y means that at least one X, at least one Y, and/or at least one X and at least one Y signature is present, wherein X may be X$^+$ or X$^-$, and Y may be Y$^+$ or Y$^-$.

7. The method according to claim 1, wherein the CD8+ Treg cell population includes CD8+Treg cells having at least one of the following signatures:
CD8$^+$α4β7$^+$CD62L$^-$X
CD8$^+$α4$^+$β7$^+$CD62L$^-$X
CD8$^+$α4β7$^+$CD62L$^-$CCR9$^+$X
CD8$^+$α4$^+$β7$^+$CD62L$^-$CCR9$^+$X
CD8$^+$α4β7$^{high}$αE$^+$CD62L$^-$X
CD8$^+$α4$^+$β7$^{high}$αE$^+$CD62L$^-$X
CD8$^+$CD62L$^-$α4β7$^{high}$αE$^+$CCR9$^+$X
CD8$^+$CD62L$^-$α4$^+$β7$^{high}$αE$^+$CCR9$^+$X
CD8$^+$α4β7$^+$CD62L$^-$Y
CD8$^+$α4$^+$β7$^+$CD62L$^-$Y
CD8$^+$α4β7$^+$CD62L$^-$CCR9$^+$Y
CD8$^+$α4$^+$β7$^+$CD62L$^-$CCR9$^+$Y
CD8$^+$α4β7$^{high}$αE$^+$CD62L$^-$Y
CD8$^+$α4$^+$β7$^{high}$αE$^+$CD62L$^-$Y
CD8$^+$CD62L$^-$α4β7$^{high}$αE$^+$CCR9$^+$Y
CD8$^+$CD62L$^-$α4$^+$β7$^{high}$αE$^+$CCR9$^+$Y
CD8$^+$α4β7$^+$CD62L$^-$XY
CD8$^+$α4$^+$β7$^+$CD62L$^-$XY
CD8$^+$α4β7$^+$CD62L$^-$CCR9$^+$XY
CD8$^+$α4$^+$β7$^+$CD62L$^-$CCR9$^+$XY
CD8$^+$α4β7$^{high}$αE$^+$CD62L$^-$XY CD8$^+$α4$^+$β7$^{high}$αE$^+$CD62L$^-$XY
CD8$^+$CD62L$^-$α4β7$^{high}$αE$^+$CCR9$^+$XY
CD8$^+$CD62L$^-$α4$^+$β7$^{high}$αE$^+$CCR9$^+$XY
wherein X may be X$^+$ or X$^-$, and Y may be Y$^+$ or Y$^-$.

8. The method according to claim 1, wherein the population of CD8$^+$ Treg cells does not contain recent thymic emigrant CD8$^+$ Treg cells having one or more of the following signatures: CD62L$^+$, CCR9$^+$CD45RA$^+$, CCR9$^+$CCR7$^+$, CCD9$^+$CD62L$^+$, CCR9$^+$CD45RO$^-$, and CCR9$^+$CCR7$^+$CD62L$^+$CD45RA$^+$CD45RO$^-$.

9. The method according to claim 1, wherein the CD8$^+$ Treg cells are CD38$^+$, CD69$^+$ and/or CD44$^+$ to denote recent activation.

10. A method of treating an inflammatory or autoimmune disease of the gastrointestinal tract, comprising administering to a subject in need thereof a pharmaceutical composition consisting essentially of an isolated CD8$^+$ Treg cell population, wherein the administered cells consist of CD8$^+$ Treg cells selected from CD8$^+$ Treg cells having the following signatures:

CD8$^+$α4β7$^+$CD62L$^-$
CD8$^+$α4$^+$β7$^+$CD62L$^-$
CD8$^+$α4β7$^+$CD62L$^-$CCR9$^+$
CD8$^+$α4$^+$β7$^+$CD62L$^-$CCR9$^+$
CD8$^+$α4β7$^{hi}$αE$^+$CD62L$^-$
CD8$^+$α4$^+$β7$^{hi}$αE$^+$CD62L$^-$
CD8$^+$CD62L$^-$α4β7$^{high}$αE$^+$CCR9$^+$ and
CD8$^+$CD62L$^-$α4$^+$β7$^{high}$αE$^+$CCR9$^+$,
CD8$^+$α4β7$^+$CD62L$^-$X/Y
CD8$^+$α4$^+$β7$^+$CD62L$^-$X/Y
CD8$^+$α4β7$^+$CD62L$^-$CCR9$^+$X/Y
CD8$^+$α4$^+$β7$^+$CD62L$^{-CCR}$9$^+$X/Y
CD8$^+$α4β7$^{hi}$αE$^+$CD62L$^-$X/Y
CD8$^+$α4$^+$β7$^{hi}$αE$^+$CD62L$^-$X/Y
CD8$^+$CD62L$^-$α4β7$^{high}$αE$^+$CCR9$^+$X/Y and
CD8$^+$CD62L$^-$α4$^+$β7$^{high}$αE$^+$CCR9$^+$X/Y,
CD8$^+$α4β7$^+$CD62L$^-$X
CD8$^+$α4$^+$β7$^+$CD62L$^-$X
CD8$^+$α4β7$^+$CD62L$^-$CCR9$^+$X
CD8$^+$α4$^+$β7$^+$CD62L$^-$CCR9$^+$X
CD8$^+$α4β7$^{high}$αE$^+$CD62L$^-$X
CD8$^+$α4$^+$β7$^{high}$αE$^+$CD62L$^-$X
CD8$^+$CD62L$^-$α4β7$^{high}$αE$^+$CCR9$^+$X
CD8$^+$CD62L$^-$α4$^+$β7$^{high}$αE$^+$CCR9$^+$X
CD8$^+$α4β7$^+$CD62L$^-$Y
CD8$^+$α4$^+$β7$^+$CD62L$^-$Y
CD8$^+$α4β7$^+$CD62L$^-$CCR9$^+$Y
CD8$^+$α4$^+$β7$^+$CD62L$^-$CCR9$^+$Y
CD8$^+$α4β7$^{high}$αE$^+$CD62L$^-$Y
CD8$^+$α4$^+$β7$^{high}$αE$^+$CD62L$^-$Y
CD8$^+$CD62L$^-$α4β7$^{high}$αE$^+$CCR9$^+$Y
CD8$^+$CD62L$^-$α4$^+$β7$^{high}$αE$^+$CCR9$^+$Y
CD8$^+$α4β7$^+$CD62L$^-$XY
CD8$^+$α4$^+$β7$^+$CD62L$^-$XY
CD8$^+$α4β7$^+$CD62L$^-$CCR9$^+$XY
CD8$^+$α4$^+$β7$^+$CD62L$^-$CCR9$^+$XY
CD8$^+$α4β7$^{high}$αE$^+$CD62L$^-$XY
CD8$^+$α4$^+$β7$^{high}$αE$^+$CD62L$^-$XY
CD8$^+$CD62L$^-$α4β7$^{high}$αE$^+$CCR9$^+$XY
CD8$^+$CD62L$^-$α4$^+$β7$^{high}$αE$^+$CCR9$^+$XY wherein:

an X signature indicates that the Treg cells can localize, have emigrated from, or are marked for preferential retention in the specific part of the gastrointestinal tract that is diseased, and is one or more selected from CD49d$^+$, CD54$^+$, CD99$^-$, CD99R$^+$, CD166$^+$, CD49a$^-$, CD49c$^-$, CD49f$^-$, CD102$^-$, CD165$^+$, CDw328$^-$, CDw329$^-$, CD37$^-$, CD38$^-$, and CD49e$^-$;

a Y signature indicates immunosuppressive regulatory function, and is one or more selected from CD25$^+$, CD58$^+$, CD73$^+$, CD95$^+$, CD105$^+$, CD107a$^+$, CD107b$^+$, CD122$^+$, CD244$^+$, CD268$^+$, CD274$^+$, CD31$^-$, CD35$^+$, CD39$^+$, CD41a$^+$, CD63$^+$, CD85$^-$, CD88$^+$, CD97$^+$, CD108$^+$, CD120b$^+$, CD127$^+$, CD130$^-$, CD132$^+$, CD151$^+$, CD210$^+$, CD221$^-$, CD226$^+$, CD335$^-$, CD336$^-$, EGF-R$^-$, CD66$^-$, CD126$^-$, CD150$^+$, CD161$^+$, CD195$^+$, CD200$^-$, and CD279$^+$; and X/Y means that at least one X, at least one Y, and/or at least one X and at least one Y signature is present, wherein X may be X$^+$ or X$^-$, and Y may be Y$^+$ or Y$^-$.

* * * * *